(12) United States Patent
Forrest et al.

(10) Patent No.: US 8,592,472 B2
(45) Date of Patent: Nov. 26, 2013

(54) CO-CRYSTALS

(75) Inventors: James Owen Forrest, Bracknell (GB); Neil George, Bracknell (GB); Rebecca Claire Burton, Bracknell (GB); Manish Maheshbhai Parmar, Bracknell (GB); Matthew David Tandy, Cambridge (GB); Suzanne Marie Buttar, Cambridge (GB); Christopher Stephen Frampton, Cambridge (GB); Adrian St Clair Brown, Cambridge (GB); Alan Patrick Chorlton, Cambridge (GB)

(73) Assignee: Syngenta Limited, Guildford, Surrey (GB)

( * ) Notice: Subject to any disclaimer, the term of this patent is extended or adjusted under 35 U.S.C. 154(b) by 119 days.

(21) Appl. No.: 13/120,897

(22) PCT Filed: Sep. 22, 2009

(86) PCT No.: PCT/GB2009/002244
§ 371 (c)(1),
(2), (4) Date: Jun. 13, 2011

(87) PCT Pub. No.: WO2010/034976
PCT Pub. Date: Apr. 1, 2010

(65) Prior Publication Data
US 2011/0245306 A1 Oct. 6, 2011

(30) Foreign Application Priority Data

Sep. 24, 2008 (GB) .................................. 0817513.5

(51) Int. Cl.
*A01N 43/653* (2006.01)
*A01P 3/00* (2006.01)
*B02C 23/00* (2006.01)

(52) U.S. Cl.
USPC ........................................... 514/383; 241/23

(58) Field of Classification Search
None
See application file for complete search history.

(56) References Cited

U.S. PATENT DOCUMENTS 4,414,210 A * 11/1983 Miller et al. .................. 514/184

FOREIGN PATENT DOCUMENTS

| GB | 1 522 657 | * | 8/1978 | ........... C07D 249/08 |
|----|-----------|---|--------|------------------------|
| WO | 2008/096005 | | 8/2008 | |
| WO | WO 2008/096005 | * | 8/2008 | ............ A01N 25/00 |
| WO | 2008/117037 | | 10/2008 | |
| WO | 2009/027624 | | 3/2009 | |

OTHER PUBLICATIONS

The Pesticide Manual, Propiconazole, Jan. 1, 1994; Pesticide Manual, World Compendium; [Pesticide Manual], Farnham, BCPC, GB, pp. 855-857.*
Morissette et al. in Drug Delivery Reviews, 56 (2004) 275-300.*
Tomlin, Clive (Editor), Worthing C R et al: "The Pesticide Manual, Propiconazole", Jan. 1, 1994; Pesticide Manual, World Compendium; [Pesticide Manual], Farnham, BCPC, GB, pp. 855-857.
Childs S L Et al.: "The Salt-Cocrystal Continuum: The Influence of Crystal Structure on Ionization State", Molecular Pharmaceutics, American Chemical Society, US, vol. 4, No. 3, Jan. 1, 2007, pp. 323-338, DOI: 10.1021/MP0601345 [retrieved on Apr. 27, 2007].

* cited by examiner

*Primary Examiner* — Dennis Heyer
(74) *Attorney, Agent, or Firm* — R. Kody Jones

(57) ABSTRACT

The present invention relates to co-crystals of propiconazole and a co-crystal forming compound.

19 Claims, 41 Drawing Sheets

US 8,592,472 B2

CO-CRYSTALS

This application is a 371 of International Application No. PCT/GB2009/002244 filed Sep. 22, 2009, which claims priority to GB 0817513.5 filed Sep. 21, 2008, the contents of which are incorporated herein by reference.

FIELD OF TECHNOLOGY

The present invention relates to novel co-crystals of propiconazole and their use in fungicidal compositions, in particular agrochemical compositions.

BACKGROUND

Propiconazole is a fungicide from the triazole group and is a steroid demethylation (ergosterol biosynthesis) inhibitor. It is a systemic foliar fungicide with protective and curative action, with translocation acropetally in the xylem. At labelled application rates, propiconazole controls numerous diseases caused by, for example, *Cochliobolus sativus, Erysiphe graminis, Leptosphaeria nodorum, Puccinia* spp., *Pyrenophora teres, Pyrenophora tritici-repentis, Rhynchosporium secalis* and *Septoria* spp. on cereals; *Mycosphaerella musicola* and *Mycosphaerella fijiensis* var. *difformis* in bananas; *Sclerotinia homoeocarpa, Rhizoctonia solani, Puccinia* spp., *Erysiphe graminis* in turf; *Rhizoctonia solani, Helminthosporium oryzae* and dirty panicle complex in rice; *Hemileia vastatrix* in coffee; *Cercospora* spp. in peanuts; *Monilinia* spp., *Podosphaera* spp., *Sphaerotheca* spp. and *Tranzschelia* spp. in stone fruit; and *Helminthosporium* spp. in maize. Propiconazole is described in "The Pesticide Manual" [The Pesticide Manual—A World Compendium; Thirteenth Edition; Editor: C. D. S. Tomlin; The British Crop Protection Council] under entry number (675).

Depending on isomeric composition propiconazole is typically a yellowish, odourless, viscous liquid between −10 and 60° C. It is known to crystallise at room temperature over long periods of time. In addition, due to substantial fluctuations in temperature that may occur during processing and storage of agrochemical formulations, propiconazole may go through cycles of melting and recrystallisation leading to the generation of large and undesirable particles. These particles could, for example, block spray nozzles during application of the product. In addition, such melting and recrystallisation events mean that it is difficult to maintain the product as a homogeneous formulation and this may lead to issues during transfer to dilution tanks and in ensuring the correct concentration on dilution. There is thus a need for new forms of propiconazole that will overcome these problems whilst still retaining its advantageous fungicidal properties.

SUMMARY OF EXEMPLARY EMBODIMENTS

Accordingly, the present invention provides novel co-crystalline forms of propiconazole with a higher melting point than the commercially available versions of propiconazole. Suitably, the melting point of the co-crystal, measured as a single melting exotherm by differential scanning calorimetry (DSC), is above 45° C. and preferably above 50° C. More suitably, the melting point is between 50 and 350° C. and preferably between 50 and 200° C. Most suitably, the melting point is between 80 and 150° C.

BRIEF DESCRIPTION OF THE FIGURES

FIG. 41 shows a DSC trace of propiconazole-D-ribose co-crystal obtained using the technique described in Example 1a.

FIG. 42 shows a DSC trace of propiconazole-2,5-dimethyl-2,5-hexanediol co-crystal obtained using the technique described in Example 1a (Batch 1).

FIG. 43 shows a DSC trace of propiconazole-2,5-dimethyl-2,5-hexanediol co-crystal obtained using the technique described in Example 1a (Batch 2).

FIG. 44 shows a DSC trace of propiconazole-trimesic acid co-crystal obtained using the technique described in Example 1a.

FIG. 45 shows a DSC trace of propiconazole-terephthalic acid co-crystal obtained using the technique described in Example 1b.

FIG. 46 shows a DSC trace of propiconazole-maleic acid co-crystal obtained using the technique described in Example 1b.

FIG. 47 shows a DSC and TGA trace of propiconazole-maleic acid co-crystal obtained using the technique described in Example 1b.

FIG. 48 shows a DSC trace of propiconazole-oxalic acid co-crystal obtained using the technique described in Example 1a.

FIG. 49 shows a DSC trace of propiconazole-oxalic acid co-crystal obtained using the technique described in Example 1b.

FIG. 50 shows a DSC trace of propiconazole-tartaric acid co-crystal obtained using the technique described in Example 1a.

FIG. 51 shows a DSC trace of propiconazole-tartaric acid co-crystal obtained using the technique described in Example 1b.

FIG. 52 shows a DSC trace of propiconazole-sucrose co-crystal obtained using the technique described in Example 1a.

FIG. 53 shows a DSC trace of propiconazole-trehalose co-crystal obtained using the technique described in Example 1a (Batch 1).

FIG. 54 shows a DSC trace of propiconazole-trehalose co-crystal obtained using the technique described in Example 1a (Batch 2).

DETAILED DESCRIPTION OF EXEMPLARY EMBODIMENTS

In particular, the invention provides a co-crystal of propiconazole with a co-crystal forming compound which has at least one functional group selected from hydroxyl (including alcohol and phenol), ketone, carboxylic acid, amide, primary amine, secondary amine, tertiary amine, sp2 amine, diazo, N-heterocyclic ring, pyrimidine or pyridine.

Suitable co-crystal forming compounds containing at least one hydroxyl functional group include, but are not limited to, 2,2'-dihydroxy-1,1'-dinaphthalene and D-ribose. Preferred co-crystal forming compounds which have hydroxyl groups include 2,2'-dihydroxy-1,1'-dinaphthalene.

Suitable co-crystal forming compounds containing at least one carboxylic acid functional group include, but are not limited to, maleic acid, oxalic acid, tartaric acid, terephthalic acid and trimesic acid. Preferred co-crystal forming compounds having carboxylic acid groups include terephthalic acid and trimesic acid.

In one embodiment, the co-crystal forming compound is selected from the group consisting of 2,2'-dihydroxy-1,1'-dinaphthalene, D-ribose, maleic acid, oxalic acid, tartaric acid, terephthalic acid and trimesic acid.

In a further embodiment, the co-crystal forming compound is selected from the group consisting of terephthalic acid, oxalic acid and tartaric acid.

The co-crystalline form of propiconazole and the co-crystal forming compound may be characterised by a crystal morphology (described in terms of the unit cell) or by selected peaks of the powder X-ray diffraction pattern expressed in terms of 2 theta (2θ) angles.

Figure 1:
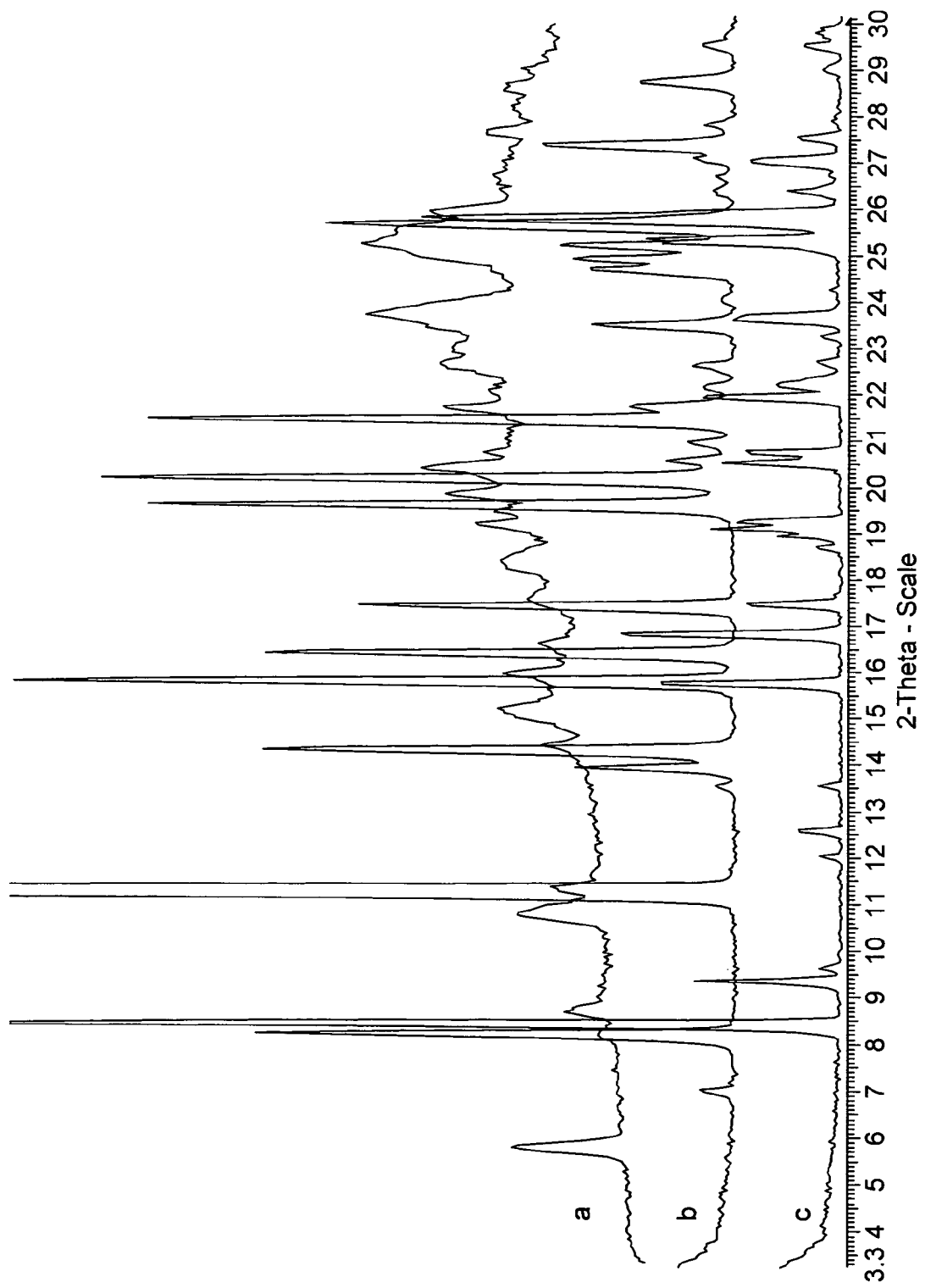
FIG. 1 shows the powder X-Ray diffraction patterns of (a) propiconazole-2,2'-dihydroxy-1,1'-dinaphthalene co-crystal obtained using the technique described in Example 1b, (b) 2,2'-dihydroxy-1,1'-dinaphthalene and (c) propiconazole.

In one embodiment of the invention, there is provided a co-crystal form of propiconazole and 2,2'-dihydroxy-1,1'-dinaphthalene. In a further embodiment, the co-crystal form of propiconazole and 2,2'-dihydroxy-1,1'-dinaphthalene is characterised by a powder X-ray diffraction pattern expressed in terms of 2θ angles, wherein the powder X-ray diffraction pattern comprises at least three 2θ angle values selected from the group comprising (a) 5.9±0.2, 10.2±0.2, 15.2±0.2 and 18.4±0.2 or (b) 5.8±0.2, 8.7±0.2, 10.7±0.2, 15.1±0.2 and 18.1±0.2. More preferably, the powder X-ray diffraction pattern comprises all of these 2θ angle values (a) or (b). These 2θ angle values are derived from those peaks of the powder X-ray diffraction pattern ascribable purely to the co-crystal; Table 1 comprises these 2θ values as well as values of further peaks which appear in the powder X-ray diffraction pattern of propiconazole and/or 2,2'-dihydroxy-1,1'-dinaphthalene as well as the co-crystal. In one embodiment, the co-crystal form of propiconazole and 2,2'-dihydroxy-1,1'-dinaphthalene is characterised by a powder X-ray diffraction pattern expressed in terms of 2θ angles, wherein the powder X-ray diffraction pattern comprises all the 2θ angle values listed in Table 1, that is, the powder X-ray diffraction pattern comprises 2θ angle values (a) 5.9±0.2, 8.8±0.2, 10.6±0.2, 11.4±0.2, 14.4±0.2, 15.2±0.2, 16.0±0.2, 18.4±0.2, 19.3±0.2, 19.9±0.2, 20.4±0.2, 21.7±0.2, 23.6±0.2, 25.1±0.2 and 25.9±0.2 or (b) 5.8±0.2, 8.7±0.2, 10.7±0.2, 11.3±0.2, 15.1±0.2, 18.1±0.2, 19.1±0.2, 19.4±0.2, 20.3±0.2, 21.2±0.2, 21.5±0.2, 22.5±0.2, 23.4±0.2, 24.3±0.2 and 25.1±0.2. All of the peaks are derived from the powder X-ray diffraction pattern of two propiconazole-2,2'-dihydroxy-1,1'-dinaphthalene co-crystals obtained using the methods of Examples 1b (Table 1(a)) and 1c (Table 1(b)). Table 1 also lists the intensity of these peaks (strong (S), medium (M) or weak (W)). The diffractograms from which all of these peak positions are derived are shown in FIGS. 1 (Table 1a) and 2 (Table 1b).

TABLE 1

| Peak | 2θ (a) | Intensity (a) | 2θ (b) | Intensity (b) |
|---|---|---|---|---|
| 1 | 5.9 | M | 5.8 | M |
| 2 | 8.8 | W | 8.7 | W |
| 3 | 10.6 | M | 10.7 | M |
| 4 | 11.4 | W | 11.3 | M |
| 5 | 14.4 | W | 15.1 | M |
| 6 | 15.2 | M | 18.1 | M |
| 7 | 16.0 | M | 19.1 | M |
| 8 | 18.4 | W | 19.4 | W |
| 9 | 19.3 | W | 20.3 | W |
| 10 | 19.9 | M | 21.2 | M |
| 11 | 20.4 | M | 21.5 | M |
| 12 | 21.7 | M | 22.5 | S |
| 13 | 23.6 | M | 23.4 | M |
| 14 | 25.1 | M | 24.3 | W |
| 15 | 25.9 | W | 25.1 | S |

Figure 3:
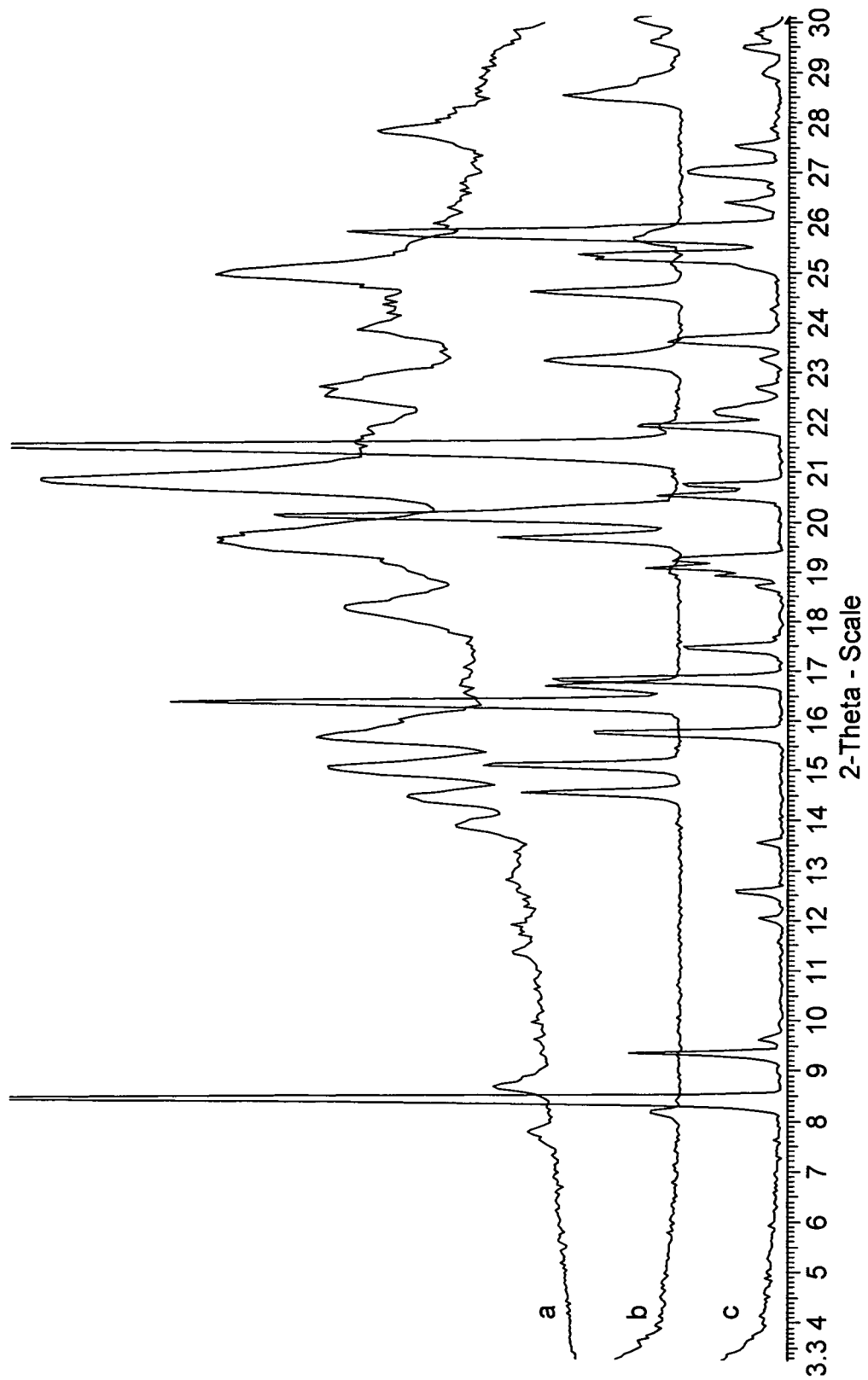
FIG. 3 shows the powder X-Ray diffraction patterns of (a) propiconazole-D-ribose co-crystal obtained using the technique described in Example 1a, (b) D-ribose and (c) propiconazole.

In one embodiment of the invention, there is provided a co-crystal form of propiconazole and D-ribose. In a further embodiment, the co-crystal form of propiconazole and D-ribose is characterised by a powder X-ray diffraction pattern expressed in terms of 2θ angles, wherein the powder X-ray diffraction pattern comprises at least three 2θ angle values selected from the group comprising (a) 7.7±0.2, 8.6±0.2, 13.9±0.2, 18.2±0.2 and 25.0±0.2 or all of the 2θ angles (b) 21.6±0.2, 24.0±0.2 and 26.1±0.2 or (c) 11.3±0.2. More preferably, the powder X-ray diffraction pattern comprises all of these 2θ angle values (a), (b) or (c). These 2θ angle values are derived from those peaks of the powder X-ray diffraction pattern ascribable purely to the co-crystal; Table 2 comprises these 2θ values as well as values of further peaks which appear in the powder X-ray diffraction pattern of propiconazole and/or D-ribose as well as the co-crystal. In one embodiment, the co-crystal form of propiconazole and D-ribose is characterised by a powder X-ray diffraction pattern expressed in terms of 2θ angles, wherein the powder X-ray diffraction pattern comprises all the 2θ angle values listed in Table 2, that is, the powder X-ray diffraction pattern comprises 2θ angle values (a) 7.7±0.2, 8.6±0.2, 13.9±0.2, 14.5±0.2, 15.0±0.2, 15.7±0.2, 18.2±0.2, 19.5±0.2, 20.8±0.2, 22.5±0.2, 22.6±0.2, 23.8±0.2, 25.0±0.2 and 27.8±0.2, (b) 9.4±0.2, 13.6±0.2, 14.7±0.2, 15.2±0.2, 16.0±0.2, 15.5±0.2, 16.9±0.2, 19.2±0.2, 20.3±0.2, 21.6±0.2, 24.0±0.2, 25.3±0.2, 26.1±0.2 and 26.5±0.2 or (c) 8.2±0.2, 11.3±0.2, 14.4±0.2, 15.7±0.2, 16.4±0.2, 17.4±0.2, 19.6±0.2, 20.2±0.2, 20.7±0.2, 21.4±0.2, 23.6±0.2, 25.1±0.2, 25.7±0.2 and 27.2±0.2. All of the peaks are derived from the powder X-ray diffraction pattern of three propiconazole-D-ribose co-crystals obtained using the methods of Examples 1a (Table 2(a)), 1c (Table 2(b)) and 1d (Table 2(c)). Table 2 also lists the intensity of these peaks (strong (S), medium (M) or weak (W)). The diffractograms from which all of these peak positions are derived are shown in FIGS. 3 (Table 2a) and 4 (Table 2b and 2c).

TABLE 2

| Peak | 2θ (a) | Intensity (a) | 2θ (b) | Intensity (b) | 2θ (c) | Intensity (c) |
|---|---|---|---|---|---|---|
| 1 | 7.7 | W | 9.4 | W | 8.2 | W |
| 2 | 8.6 | W | 13.6 | W | 11.3 | M |
| 3 | 13.9 | W | 14.7 | W | 14.4 | W |

TABLE 2-continued

| Peak | 2θ (a) | Intensity (a) | 2θ (b) | Intensity (b) | 2θ (c) | Intensity (c) |
|---|---|---|---|---|---|---|
| 4 | 14.5 | M | 15.2 | W | 15.7 | M |
| 5 | 15.0 | M | 16.0 | W | 16.4 | M |
| 6 | 15.7 | M | 16.5 | W | 17.4 | W |
| 7 | 18.2 | M | 16.9 | W | 19.6 | M |
| 8 | 19.5 | S | 19.2 | W | 20.2 | M |
| 9 | 20.8 | S | 20.3 | M | 20.7 | W |
| 10 | 22.5 | M | 21.8 | M | 21.4 | M |
| 11 | 22.6 | M | 24.0 | W | 23.6 | W |
| 12 | 23.8 | W | 25.3 | W | 25.1 | W |
| 13 | 25.0 | S | 26.1 | M | 25.7 | M |
| 14 | 27.8 | M | 26.5 | W | 27.2 | W |

Figure 5:
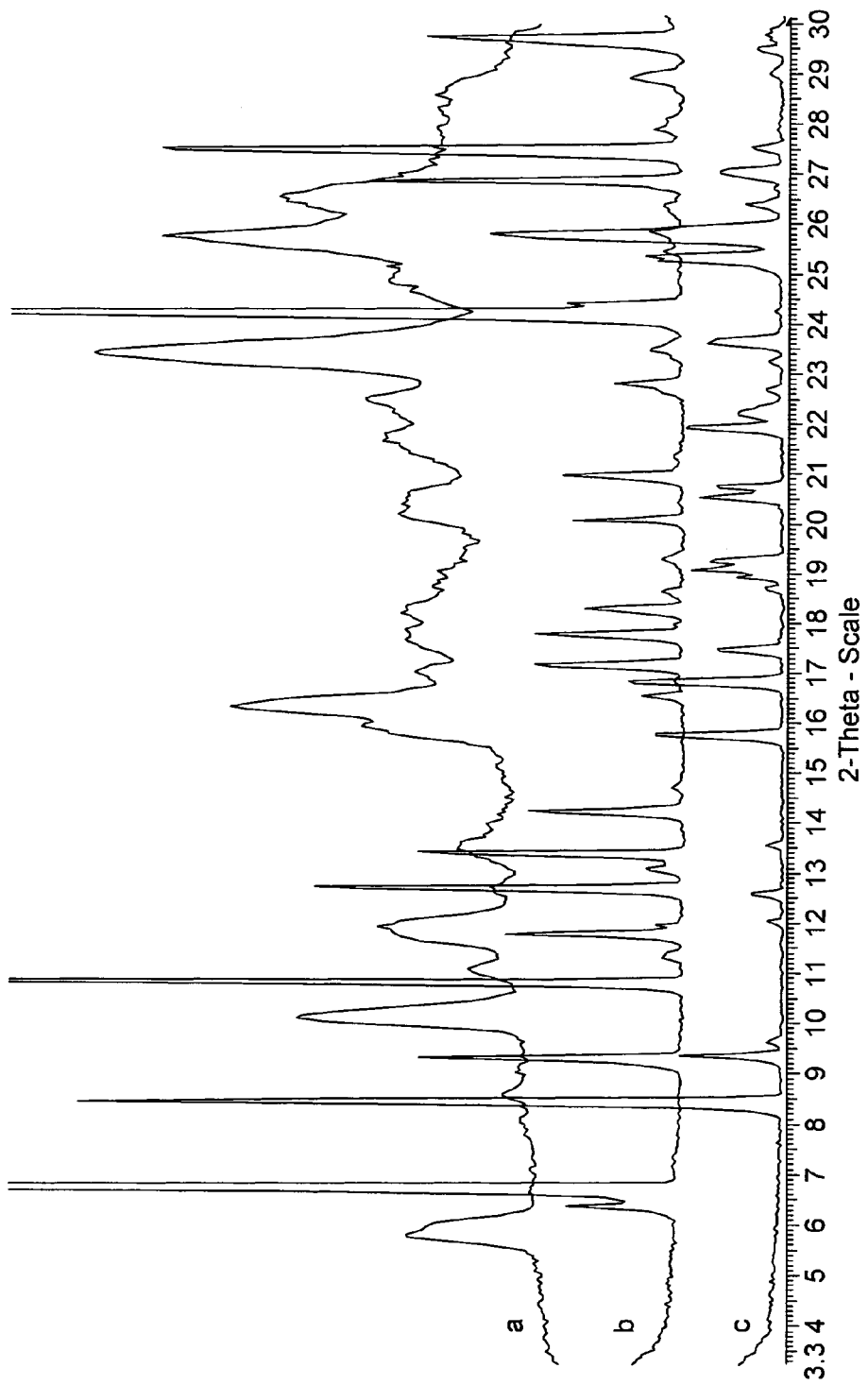
FIG. 5 shows the powder X-Ray diffraction patterns of (a) propiconazole-2,5-dimethyl-2,5-hexanediol co-crystal obtained using the technique described in Example 1a (Batch 1), (b) propiconazole-2,5-dimethyl-2,5-hexanediol co-crystal obtained using the technique described in Example 1a (Batch 2), (c) 2,5-dimethyl-2,5-hexanediol and (d) propiconazole.

In another embodiment of the invention, there is provided a co-crystal form of propiconazole and trimesic acid. In a further embodiment, the co-crystal form of propiconazole and trimesic acid is characterised by a powder X-ray diffraction pattern expressed in terms of 2θ angles, wherein the powder X-ray diffraction pattern comprises the 2θ angle values 5.8±0.2, 10.2±0.2 and 16.3±0.2. These 2θ angle values are derived from those peaks of the powder X-ray diffraction pattern ascribable purely to the co-crystal; Table 3 comprises these 2θ values as well as values of further peaks which appear in the powder X-ray diffraction pattern of propiconazole and/or trimesic acid as well as the co-crystal. In one embodiment, the co-crystal form of propiconazole and trimesic acid is characterised by a powder X-ray diffraction pattern comprising all the 2θ angle values listed in Table 3, that is, the powder X-ray diffraction pattern comprises 2θ angle values 5.8±0.2, 10.2±0.2, 11.1±0.2, 11.9±0.2, 13.5±0.2, 15.9±0.2, 16.3±0.2, 18.1±0.2, 20.1±0.2, 21.7±0.2, 22.6±0.2, 23.4±0.2, 25.7±0.2 and 26.5±0.2. All of the peaks are derived from the powder X-ray diffraction pattern of a propiconazole-trimesic acid co-crystal obtained using the method of Example 1a. Table 3 also lists the intensity of these peaks (strong (S), medium (M) or weak (W)). The diffractogram from which all of these peak positions are derived is shown in FIG. 5.

TABLE 3

| Peak | 2θ | Intensity |
|---|---|---|
| 1 | 5.8 | M |
| 2 | 10.2 | M |
| 3 | 11.1 | W |
| 4 | 11.9 | M |
| 5 | 13.5 | W |
| 6 | 15.9 | W |
| 7 | 16.3 | S |
| 8 | 18.1 | W |
| 9 | 20.1 | W |
| 10 | 21.7 | W |
| 11 | 22.6 | W |
| 12 | 23.4 | S |
| 13 | 25.7 | S |
| 14 | 26.5 | M |

Figure 6:
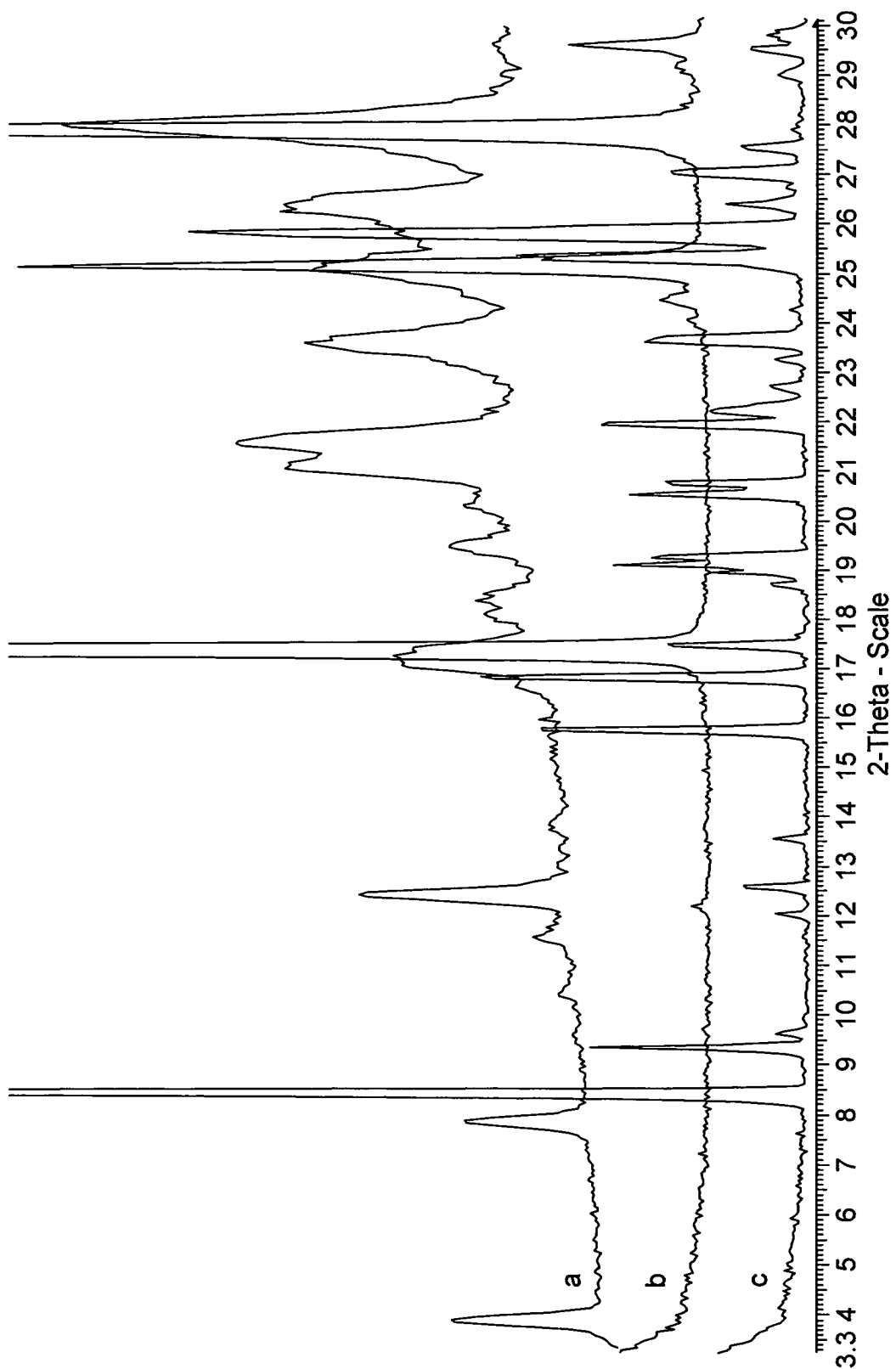
FIG. 6 shows the powder X-Ray diffraction patterns of (a) propiconazole-trimesic acid co-crystal obtained using the technique described in Example 1a, (b) trimesic acid and (c) propiconazole.

In another embodiment of the invention, there is provided a co-crystal form of propiconazole and terephthalic acid. In a further embodiment, the co-crystal form of propiconazole and terephthalic acid is characterised by a powder X-ray diffraction pattern expressed in terms of 2θ angles, wherein the powder X-ray diffraction pattern comprises at least three of the 2θ angle values listed in Table 4A. In one embodiment, the co-crystal form of propiconazole and terephthalic acid is characterised by a powder X-ray diffraction pattern comprising all the 2θ angle values listed in Table 4A. Table 4A shows the 2θ values of selected peak positions of the powder X-ray diffraction pattern of a propiconazole-terephthalic acid co-crystal obtained using the method of Example 1b, as well as the intensity of these peaks (strong (S), medium (M) or weak (W)). The diffractogram from which these peak positions are derived is shown in FIG. 6.

TABLE 4A

| Peak | 2θ | Intensity |
|---|---|---|
| 1 | 3.9 | M |
| 2 | 7.9 | M |
| 3 | 12.4 | M |
| 4 | 17.2 | M |
| 5 | 18.4 | W |
| 6 | 19.5 | W |
| 7 | 21.1 | M |
| 8 | 21.6 | S |
| 9 | 23.6 | M |
| 10 | 25.1 | M |
| 11 | 26.3 | M |
| 12 | 27.9 | S |

In one embodiment of the invention, the co-crystal form of propiconazole and terephthalic acid is characterised by the unit cell parameters of a propiconazole/terephthalic acid single crystal shown in Table 4B. This single crystal was obtained using the method of Example 1g.

TABLE 4B

| Space Group | P -1 |
|---|---|
| Cell Lengths (Å) | a = 5.3661(5) |
| | b = 8.5614(8) |
| | c = 21.997(2) |
| Cell Angles (°) | α = 95.630(3) |
| | β = 91.600(3) |
| | γ = 99.293(3) |
| Z' | 2 |
| R-factor | 0.0257 |

Figure 7:
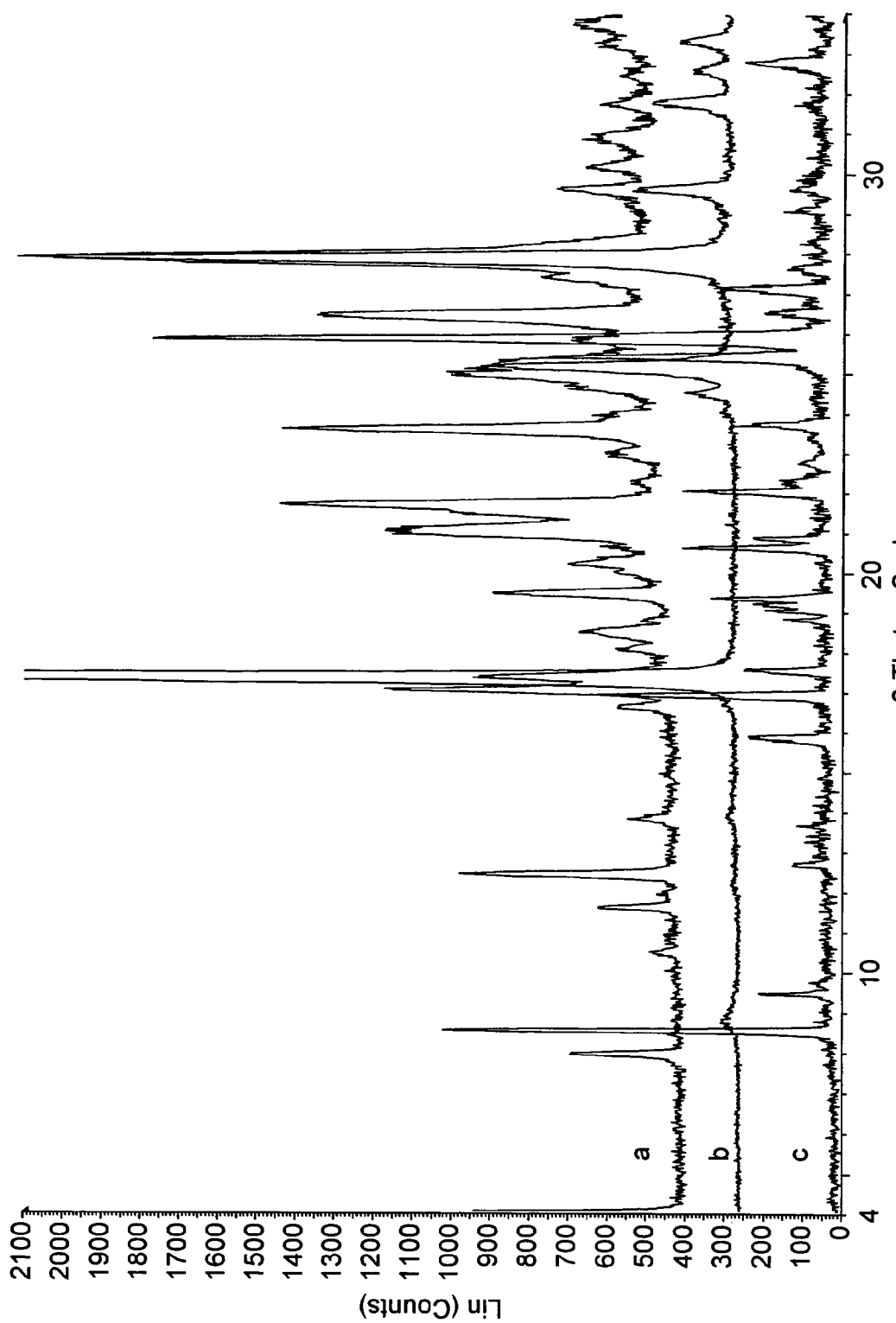
FIG. 7 shows the powder X-Ray diffraction patterns of (a) propiconazole-terephthalic acid co-crystal obtained using the technique described in Example 1b, (b) terephthalic acid and (c) propiconazole.

In a further embodiment, the co-crystal form of propiconazole and terephthalic acid is characterised by a powder X-ray diffraction pattern expressed in terms of 2θ angles, wherein the powder X-ray diffraction pattern comprises at least three 2θ angle values selected from the group comprising 4.1±0.2, 8.0±0.2, 11.8±0.2, 18.6±0.2, 21.0±0.2 and 21.7±0.2. More preferably, the powder X-ray diffraction pattern comprises all of the 2θ angle values listed above. These 2θ angle values are derived from those peaks of the powder X-ray diffraction pattern ascribable purely to the co-crystal; Table 4C comprises these 2θ values as well as values of further peaks which appear in the powder X-ray diffraction pattern of propiconazole and/or terephthalic acid as well as the co-crystal. In one embodiment, the co-crystal form of propiconazole and terephthalic acid is characterised by a powder X-ray diffraction pattern comprising all the 2θ angle values listed in Table 4C, that is, the powder X-ray diffraction pattern comprises 2θ angle values 4.1±0.2, 8.0±0.2, 11.8±0.2, 12.5±0.2, 17.1±0.2, 17.3±0.2, 18.6±0.2, 19.7±0.2, 21.0±0.2, 21.7±0.2, 23.6±0.2, 25.0±0.2, 26.3±0.2 and 27.9±0.2. All of the peaks are derived from the powder X-ray diffraction pattern of a propiconazole-terephthalic acid co-crystal obtained using the method of Example 1g. Table 4C also lists the intensity of these peaks (strong (S), medium (M) or weak (W)). The diffractogram from which all of these peak positions are derived is shown in FIG. 7.

TABLE 4C

| Peak | 2θ | Intensity |
|---|---|---|
| 1 | 4.1 | M |
| 2 | 8.0 | W |
| 3 | 11.8 | W |
| 4 | 12.5 | M |
| 5 | 17.1 | M |
| 6 | 17.3 | M |
| 7 | 18.6 | W |
| 8 | 19.7 | M |
| 9 | 21.0 | M |
| 10 | 21.7 | S |
| 11 | 23.6 | S |
| 12 | 25.0 | M |
| 13 | 26.2 | S |
| 14 | 27.9 | S |

Figure 8:
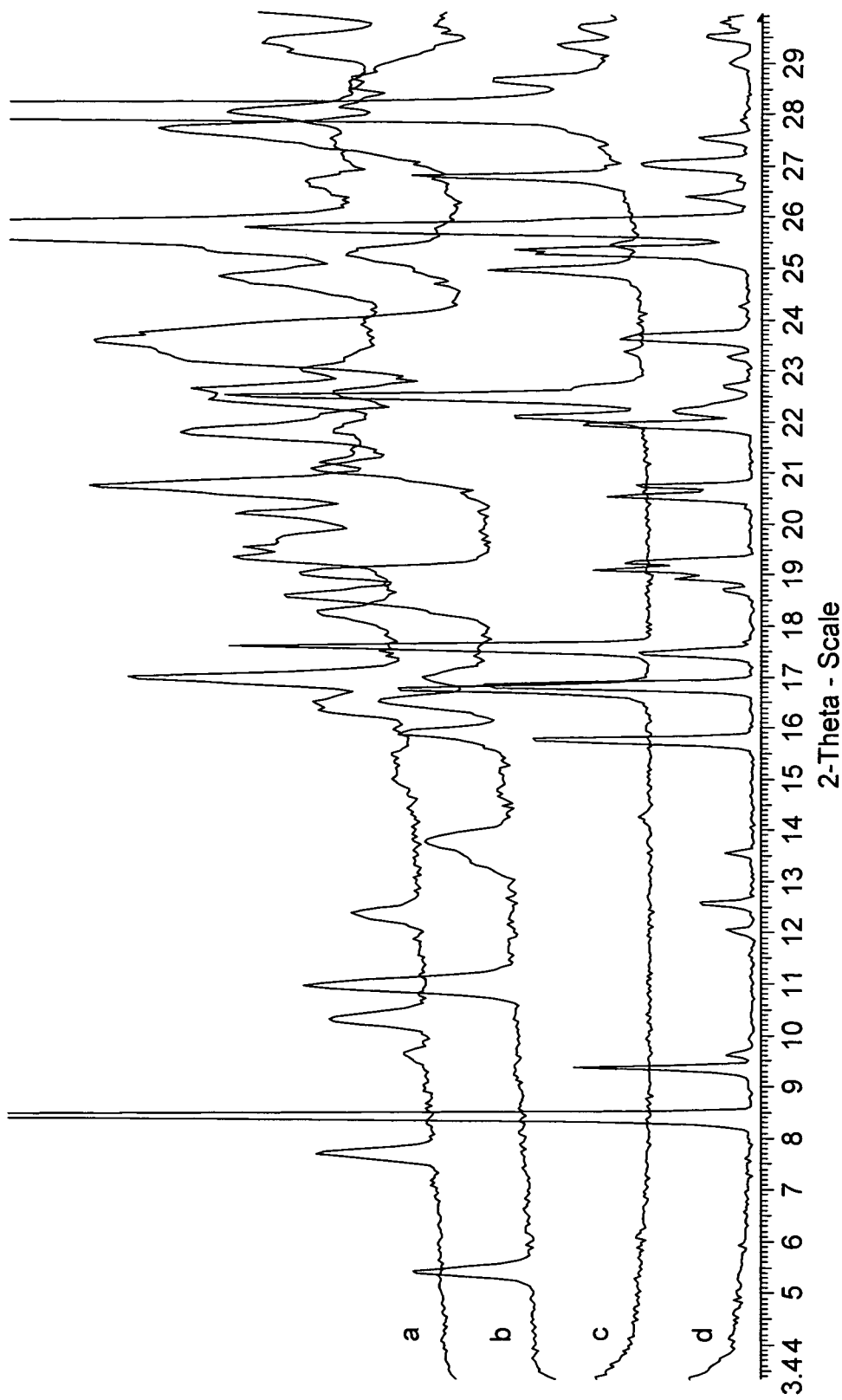
FIG. 8 shows the powder X-Ray diffraction patterns of (a) propiconazole-maleic acid co-crystal obtained using the technique described in Example 1b after subjection to chemical stability analysis, (b) propiconazole-maleic acid co-crystal obtained using the technique described in Example 1b before subjection to chemical stability analysis, (c) maleic acid and (d) propiconazole.

In another embodiment of the invention, there is provided a co-crystal form of propiconazole and maleic acid. In a further embodiment, the co-crystal form of propiconazole and maleic acid is characterised by a powder X-ray diffraction pattern expressed in terms of 2θ angles, wherein the powder X-ray diffraction pattern comprises at least three 2θ angle values selected from the group comprising (a) 7.6±0.2, 10.3±0.2, 16.4±0.2, 18.2±0.2, 19.4±0.2 and 20.2±0.2, (d) 7.6±0.2, 10.4±0.2, 11.8±0.2, 15.4±0.2, 16.1±0.2 and 19.5±0.2 or (e) 5.9±0.2, 7.6±0.2, 10.5±0.2, 15.5 0.2 and 16.2±0.2 or all of the 2θ angle values (b) 5.4±0.2, 10.9±0.2 and 21.1±0.2 or (c) 21.4±0.2 and, 26.1±0.2. More preferably, the powder X-ray diffraction pattern comprises all of the 2θ angle values (a), (b), (c), (d) or (e). These 2θ angle values are derived from those peaks of the powder X-ray diffraction pattern ascribable purely to the co-crystal; Table 5 comprises these 2θ values as well as values of further peaks which appear in the powder X-ray diffraction pattern of propiconazole and/or maleic acid as well as the co-crystal. In one embodiment, the co-crystal form of propiconazole and maleic acid is characterised by a powder X-ray diffraction pattern expressed in terms of 2θ angles, wherein the powder X-ray diffraction pattern comprises all the 2θ angle values listed in Table 5, that is, the powder X-ray diffraction pattern comprises the 2θ angle values (a) 7.6±0.2, 10.3±0.2, 12.4±0.2, 16.4±0.2, 16.9±0.2, 18.2±0.2, 19.4±0.2, 20.2±0.2, 20.7±0.2, 22.6±0.2, 24.8±0.2, 25.8±0.2, 28.0±0.2 and 29.4±0.2, (b) 5.4±0.2, 10.9±0.2, 13.8±0.2, 15.9±0.2, 16.5±0.2, 17.0±0.2, 18.6±0.2, 19.1±0.2, 21.1±0.2, 21.8±0.2, 22.6±0.2, 23.6±0.2, 25.3±0.2 and 27.7±0.2, (c) 11.7±0.2, 12.5±0.2, 17.6±0.2, 18.5±0.2, 19.1±0.2, 20.8±0.2, 21.4±0.2, 22.0±0.2, 22.5±0.2, 23.5±0.2, 25.2±0.2, 26.1±0.2, 27.6±0.2 and 28.4±0.2, (d) 5.7±0.2, 7.6±0.2, 8.6±0.2, 10.4±0.2, 11.8±0.2, 13.5±0.2, 13.8±0.2, 15.4±0.2, 16.1±0.2, 16.5±0.2, 17.4±0.2, 17.7±0.2, 18.6±0.2, 19.5±0.2, 20.5±0.2, 21.8±0.2, 23.5±0.2, 25.4±0.2, 26.3±0.2 and 28.2±0.2 or (e) 5.9±0.2, 7.6±0.2, 10.5±0.2, 11.8±0.2, 13.6±0.2, 15.5±0.2, 16.2±0.2, 16.6±0.2, 17.6±0.2, 18.6±0.2, 19.4±0.2, 20.6±0.2, 21.9±0.2, 25.6±0.2, 26.6±0.2 and 28.1±0.2. All of these peaks are derived from the powder X-ray diffraction patterns of five propiconazole-maleic acid co-crystals obtained using the methods of Examples 1b (Table 5a and 5d) and 1c (Table 5b). The 2θ values shown in Table 5b and 5e are those obtained after the crystals of Table 5a and 5d, respectively, were subject to chemical stability analysis. Table 5 also lists the intensity of these peaks (strong (S), medium (M) or weak (W)). The diffractograms from which all of these peak positions are derived are shown in FIGS. 8 (Table 5a and b), 9 (Table 5c) and 10 (Table 5d and e).

TABLE 5

| Peak | 2θ (a) | Int. (a) | 2θ (b) | Int. (b) | 2θ (c) | Int. (c) | 2θ (d) | Int. (d) | 2θ (e) | Int. (e) |
|---|---|---|---|---|---|---|---|---|---|---|
| 1 | 7.6 | M | 5.4 | M | 11.7 | W | 5.7 | W | 5.9 | W |
| 2 | 10.3 | M | 10.9 | M | 12.5 | W | 7.6 | M | 7.6 | M |
| 3 | 12.4 | M | 13.8 | M | 17.6 | W | 8.6 | W | | |
| 4 | 16.4 | W | 15.9 | M | 18.5 | W | 10.4 | W | 10.5 | W |
| 5 | 16.9 | M | 16.5 | M | 19.1 | W | 11.8 | W | 11.8 | W |
| 6 | 18.2 | W | 17.0 | W | 20.8 | M | 13.5 | W | 13.6 | W |
| 7 | 19.4 | M | 18.6 | M | 21.4 | W | 13.8 | W | | |
| 8 | 20.2 | M | 19.1 | M | 22.0 | S | 15.4 | M | 15.5 | W |
| 9 | 20.7 | S | 21.1 | M | 22.5 | M | 16.1 | W | 16.2 | W |
| 10 | 22.6 | M | 21.8 | S | 23.5 | M | 16.5 | M | 16.6 | W |
| 11 | 24.8 | M | 22.6 | W | 25.2 | M | 17.4 | M | 17.6 | W |
| 12 | 25.8 | S | 23.6 | S | 26.1 | M | 17.7 | M | | |
| 13 | 28.0 | M | 25.3 | M | 27.6 | M | 18.6 | M | 18.6 | W |
| 14 | 29.4 | M | 27.7 | S | 28.4 | W | 19.5 | S | 19.4 | W |
| 15 | | | | | | | 20.5 | S | 20.6 | W |
| 16 | | | | | | | 21.8 | S | 21.9 | M |
| 17 | | | | | | | 23.5 | M | | |
| 18 | | | | | | | 25.4 | S | 25.6 | W |
| 19 | | | | | | | 26.3 | S | 26.6 | W |
| 20 | | | | | | | 28.2 | M | 28.1 | W |

Figure 11:
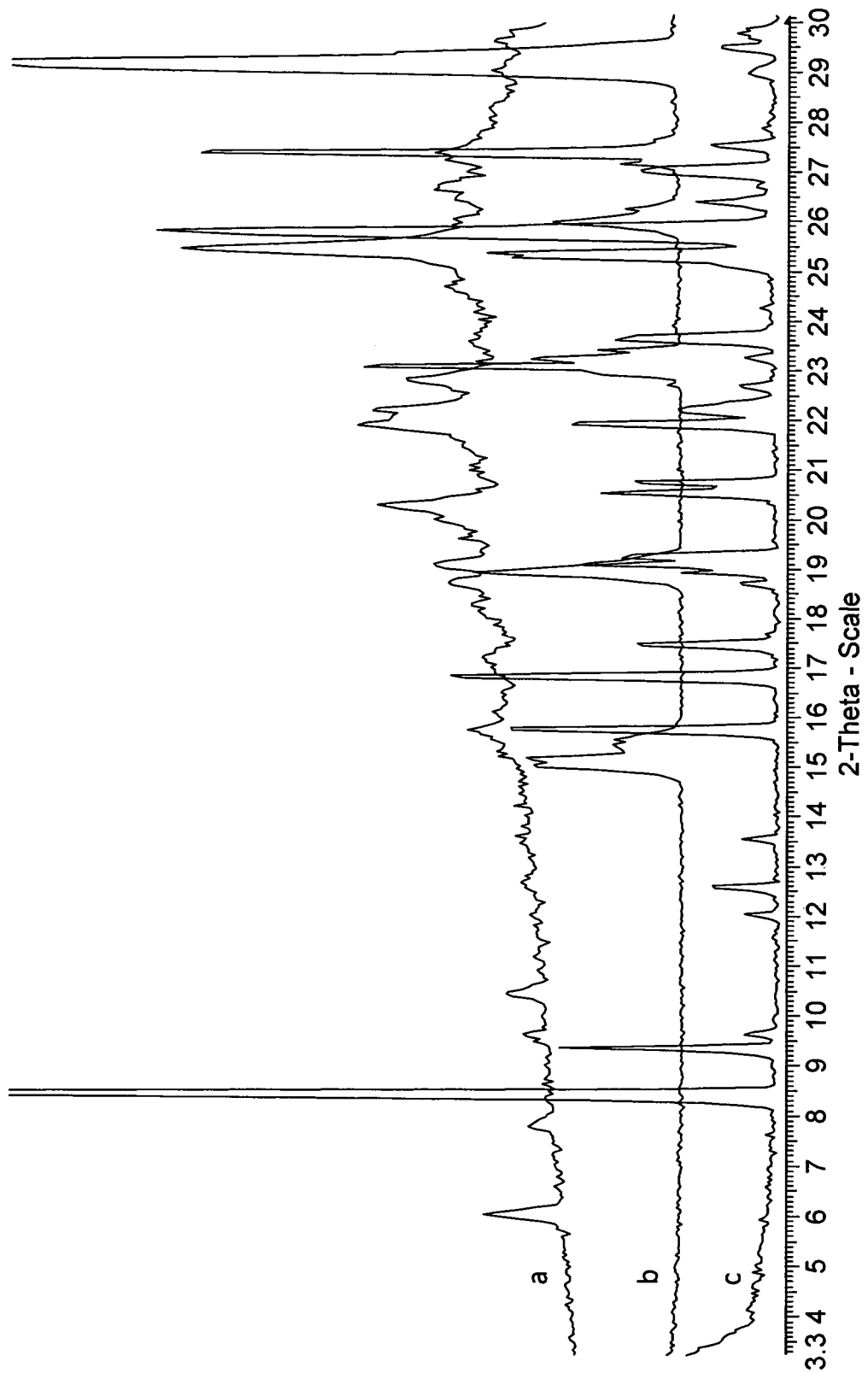
FIG. 11 shows the powder X-Ray diffraction patterns of (a) ammonium acetate, (b) propiconazole-ammonium acetate co-crystal obtained using the technique described in Example 1c and (c) propiconazole.

In another embodiment of the invention, there is provided a co-crystal form of propiconazole and oxalic acid. In a further embodiment, the co-crystal form of propiconazole and oxalic acid is characterised by a powder X-ray diffraction pattern expressed in terms of 2θ angles, wherein the powder X-ray diffraction pattern comprises at least three of the 2θ angle values listed in Table 6A(a), 6A(b), 6A(c) or 6A(d). In one embodiment, the co-crystal form of propiconazole and oxalic acid is characterised by a powder X-ray diffraction pattern comprising all the 2θ angle values listed in Table 6A(a), 6A(b), 6A(c) or 6A(d). Table 6A shows the 2θ values of selected peak positions of the powder X-ray diffraction pattern of four propiconazole-oxalic acid co-crystals obtained using the methods of Examples 1a, b, c and d, respectively, as well as the intensity of these peaks (strong (S), medium (M) or weak (W)). The diffractograms from which these peak positions are derived are shown in FIGS. 11 (Table 6A(a), 12 (Table 6A(b)) and 13 (Table 6A(c) and (d)).

TABLE 6A

| Peak | 2θ (a) | Intensity (a) | 2θ (b) | Intensity (b) | 2θ (c) | Intensity (c) | 2θ (d) | Intensity (d) |
|---|---|---|---|---|---|---|---|---|
| 1 | 6.1 | M | 6.5 | M | 6.5 | W | 6.6 | W |
| 2 | 7.8 | W | 8.4 | M | 10.9 | W | 8.4 | W |
| 3 | 10.4 | W | 10.3 | W | 16.6 | W | 9.2 | W |
| 4 | 15.7 | W | 11.1 | M | 17.4 | W | 11.0 | W |
| 5 | 18.7 | W | 13.3 | W | 19.5 | W | 15.6 | W |
| 6 | 19.1 | W | 16.5 | M | 20.4 | W | 16.3 | M |
| 7 | 20.3 | M | 17.7 | W | 20.7 | W | 17.6 | W |
| 8 | 21.9 | M | 18.8 | M | 22.6 | W | 19.3 | W |
| 9 | 22.2 | M | 19.3 | M | 25.9 | M | 19.7 | W |
| 10 | 22.7 | W | 19.8 | M | | | 20.8 | M |
| 11 | 25.4 | S | 20.9 | S | | | 22.6 | M |
| 12 | 26.6 | W | 22.7 | S | | | 25.7 | M |
| 13 | | | 26.3 | S | | | 26.1 | M |
| 14 | | | 27.2 | W | | | 27.2 | W |
| 15 | | | 29.0 | M | | | 28.7 | W |

Figure 14:
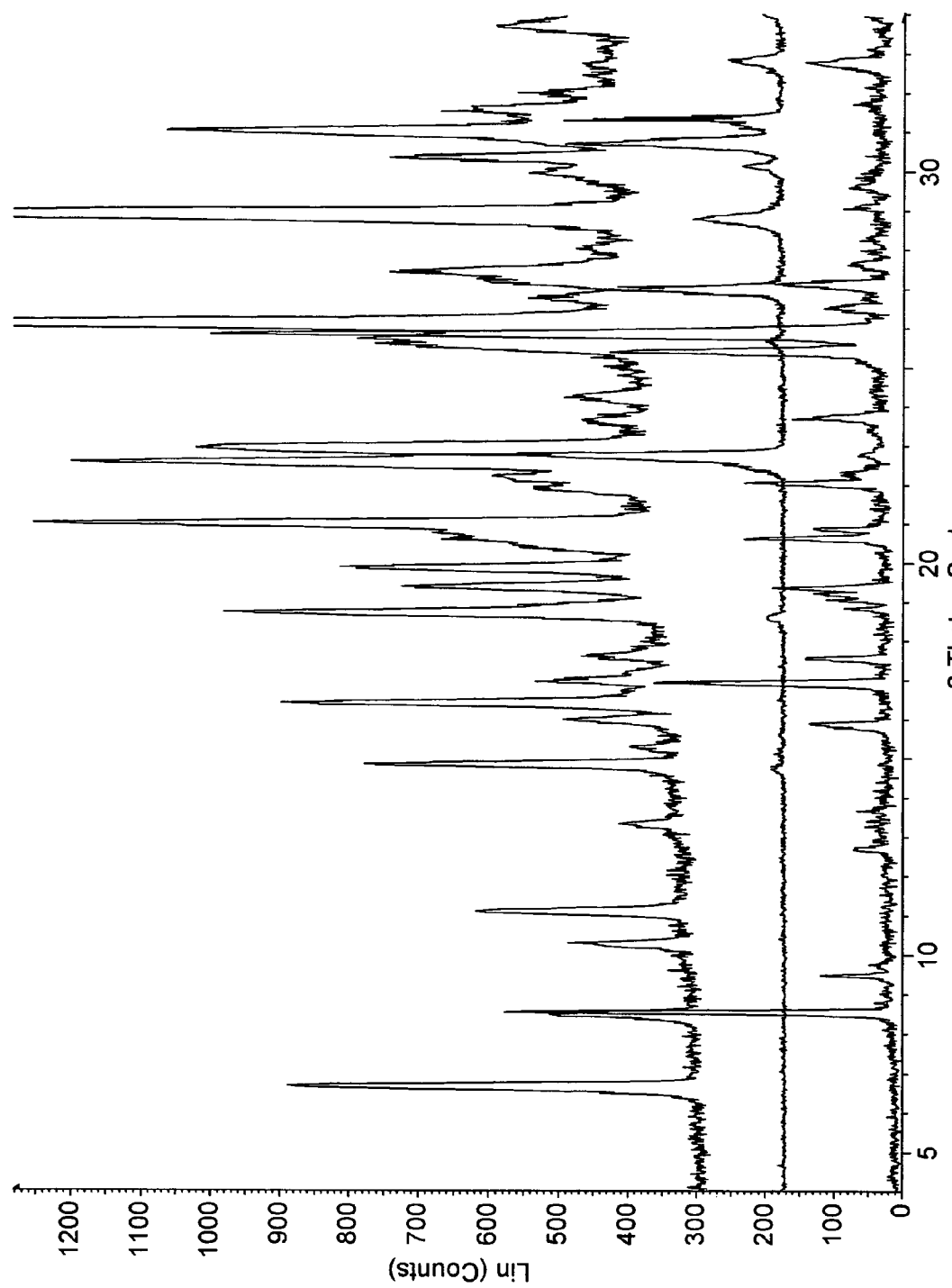
FIG. 14 shows the powder X-Ray diffraction patterns of (a) oxalic acid, (b) propiconazole-oxalic acid co-crystal obtained using the technique described in Example 1c, (c) propiconazole-oxalic acid co-crystal obtained using the technique described in Example 1d and (d) propiconazole.

In a further embodiment, the co-crystal form of propiconazole and oxalic acid is characterised by a powder X-ray diffraction pattern expressed in terms of 2θ angles, wherein the powder X-ray diffraction pattern comprises at least three 2θ angle values selected from the group comprising 6.7±0.2, 10.3±0.2, 11.1±0.2, 14.9±0.2, 16.3±0.2 and 19.7±0.2. More preferably, the powder X-ray diffraction pattern comprises all of the 2θ angle values listed above. These 2θ angle values are derived from those peaks of the powder X-ray diffraction pattern ascribable purely to the co-crystal; Table 6B comprises these 2θ values as well as values of further peaks which appear in the powder X-ray diffraction pattern of propiconazole and/or oxalic acid as well as the co-crystal. In one embodiment, the co-crystal form of propiconazole and oxalic acid is characterised by a powder X-ray diffraction pattern comprising all the 2θ angle values listed in Table 6B, that is, the powder X-ray diffraction pattern comprises 2θ angle values 6.7±0.2, 8.4±0.2, 10.3±0.2, 11.1±0.2, 14.9±0.2, 16.3±0.2, 18.7±0.2, 19.5±0.2, 19.7±0.2, 21.0±0.2, 22.2±0.2, 22.6±0.2, 26.0±0.2, 27.2±0.2, 28.7±0.2 and 28.1±0.2. All of the peaks are derived from the powder X-ray diffraction pattern of a propiconazole-oxalic acid co-crystal obtained using the method of Example 1f. Table 6B also lists the intensity of these peaks (strong (S), medium (M) or weak (W)). The diffractogram from which all of these peak positions are derived is shown in FIG. 14.

TABLE 6B

| Peak | 2θ | Intensity |
|---|---|---|
| 1 | 6.7 | S |
| 2 | 8.4 | M |
| 3 | 10.3 | M |
| 4 | 11.1 | M |
| 5 | 14.9 | M |
| 6 | 16.3 | S |
| 7 | 18.7 | S |
| 8 | 19.5 | M |
| 9 | 19.7 | M |
| 10 | 21.0 | S |
| 11 | 22.2 | S |
| 12 | 22.6 | S |
| 13 | 26.0 | S |
| 14 | 27.2 | M |
| 15 | 28.7 | S |
| 16 | 31.1 | S |

Figure 15:
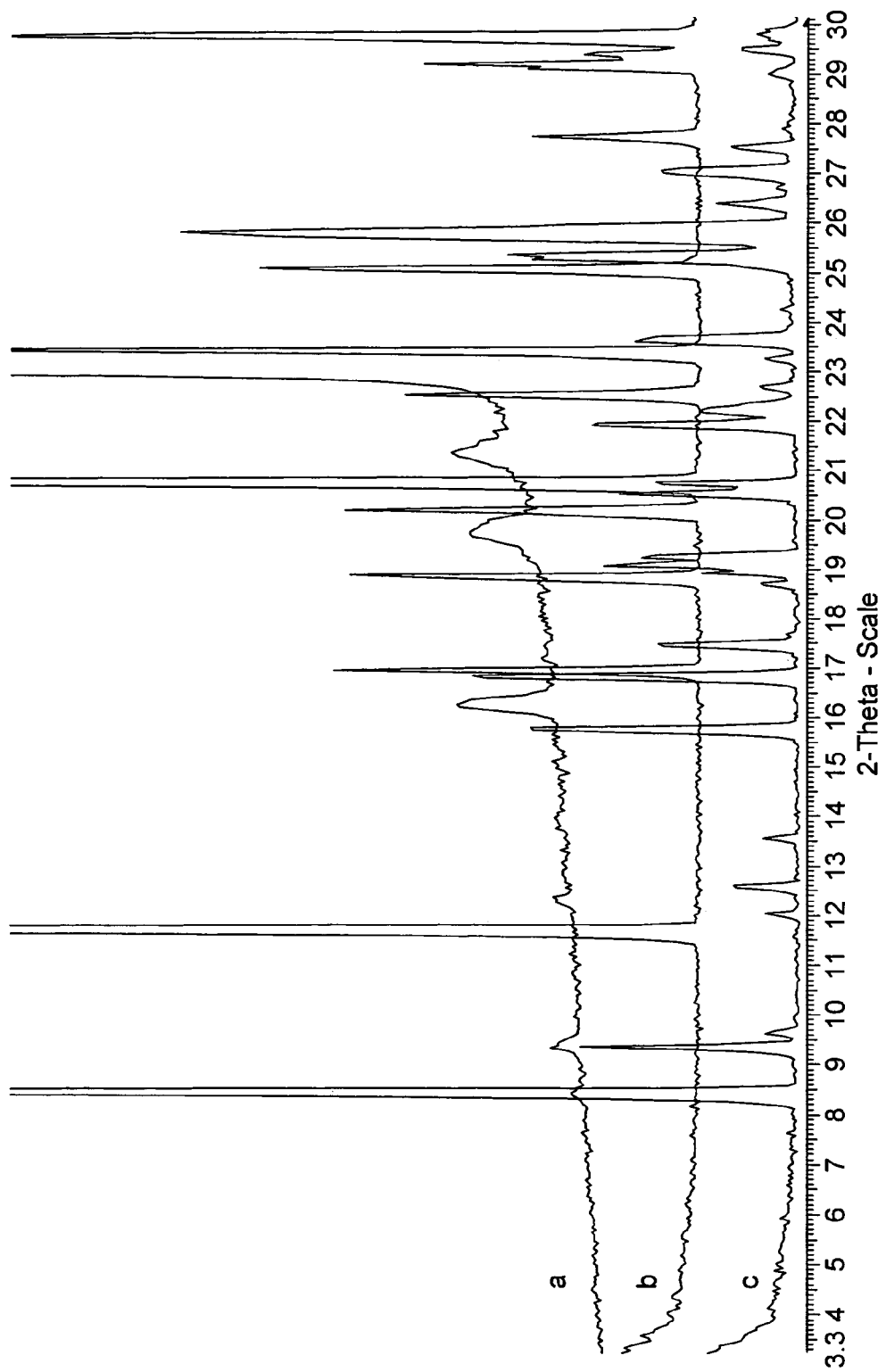
FIG. 15 shows the powder X-Ray diffraction patterns of (a) propiconazole-urea co-crystal obtained using the technique described in Example 1d, (b) urea and (c) propiconazole.
Figure 16:
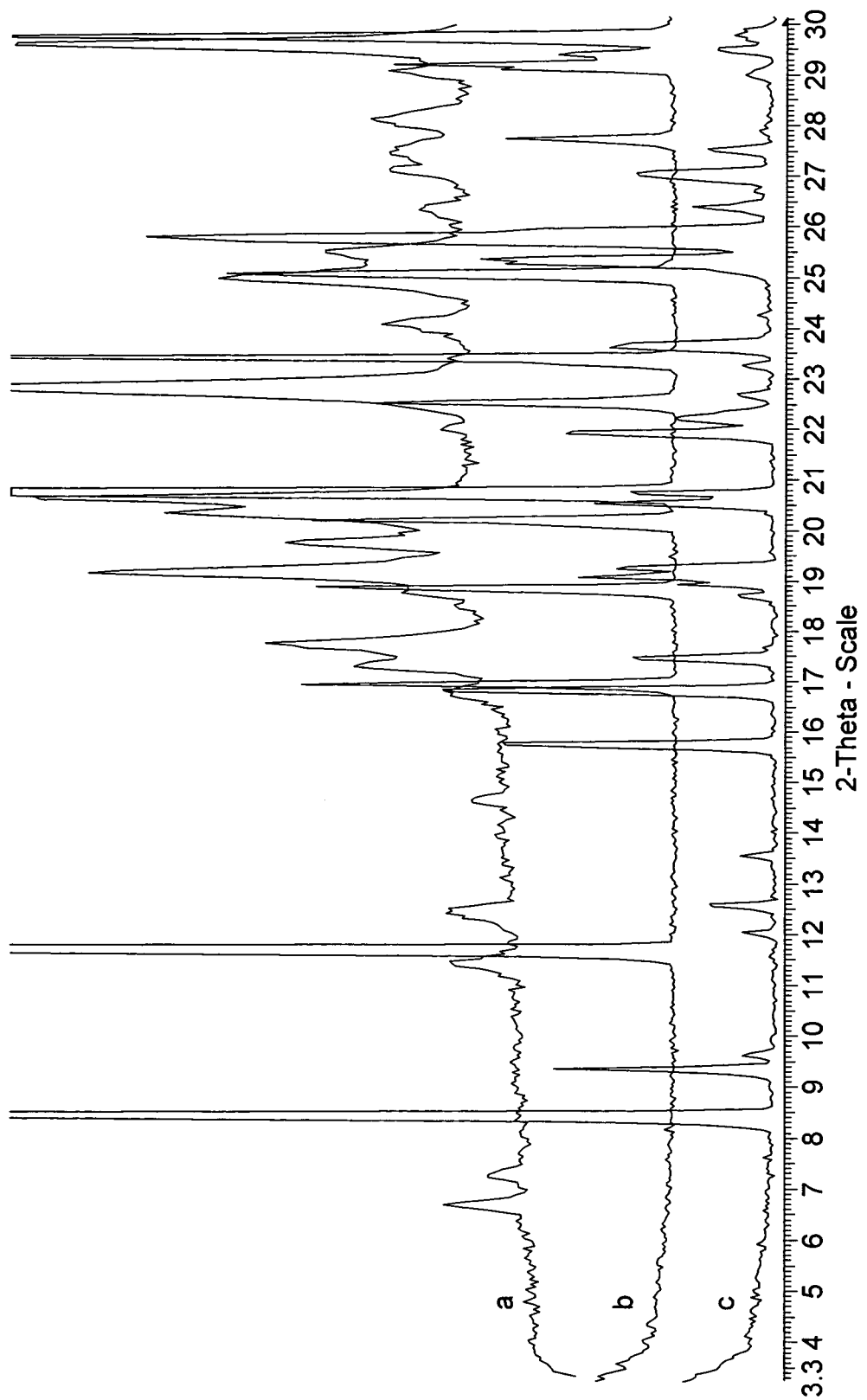
FIG. 16 shows the powder X-Ray diffraction patterns of (a) propiconazole-tartaric acid co-crystal obtained using the technique described in Example 1a, (b) tartaric acid and (c) propiconazole.

In another embodiment of the invention, there is provided a co-crystal form of propiconazole and tartaric acid. In a further embodiment, the co-crystal form of propiconazole and tartaric acid is characterised by a powder X-ray diffraction pattern expressed in terms of 2θ angles, wherein the powder X-ray diffraction pattern comprises at least three of the 2θ angle values listed in Table 7A(a) or Table 7A(b). In one embodiment, the co-crystal form of propiconazole and tartaric acid is characterised by a powder X-ray diffraction pattern comprising all the 2θ angle values listed in Table 7A(a) or Table 7A(b). Table 7A shows the 2θ values of selected peak positions of the powder X-ray diffraction pattern of two propiconazole-tartaric acid co-crystals obtained using the methods of Examples 1a and b, respectively, as well as the intensity of these peaks (strong (S), medium (M) or weak (W)). The diffractograms from which these peak positions are derived are shown in FIGS. 15 and 16, respectively.

TABLE 7A

| Peak | 2θ (a) | Intensity (a) | 2θ (b) | Intensity (b) |
|---|---|---|---|---|
| 1 | 9.4 | W | 6.8 | M |
| 2 | 12.3 | W | 7.4 | W |
| 3 | 16.2 | M | 11.4 | M |
| 4 | 19.8 | W | 12.4 | M |
| 5 | 21.4 | W | 16.8 | W |
| 6 | 23.3 | S | 17.4 | M |
| 7 | 24.6 | W | 17.8 | M |
| 8 | 25.7 | M | 19.4 | S |

TABLE 7A-continued

| Peak | 2θ (a) | Intensity (a) | 2θ (b) | Intensity (b) |
|---|---|---|---|---|
| 9 | 27.0 | W | 19.9 | M |
| 10 | | | 20.5 | M |
| 11 | | | 20.9 | S |
| 12 | | | 22.8 | S |
| 13 | | | 24.2 | M |
| 14 | | | 25.1 | M |
| 15 | | | 29.6 | S |

Figure 17:
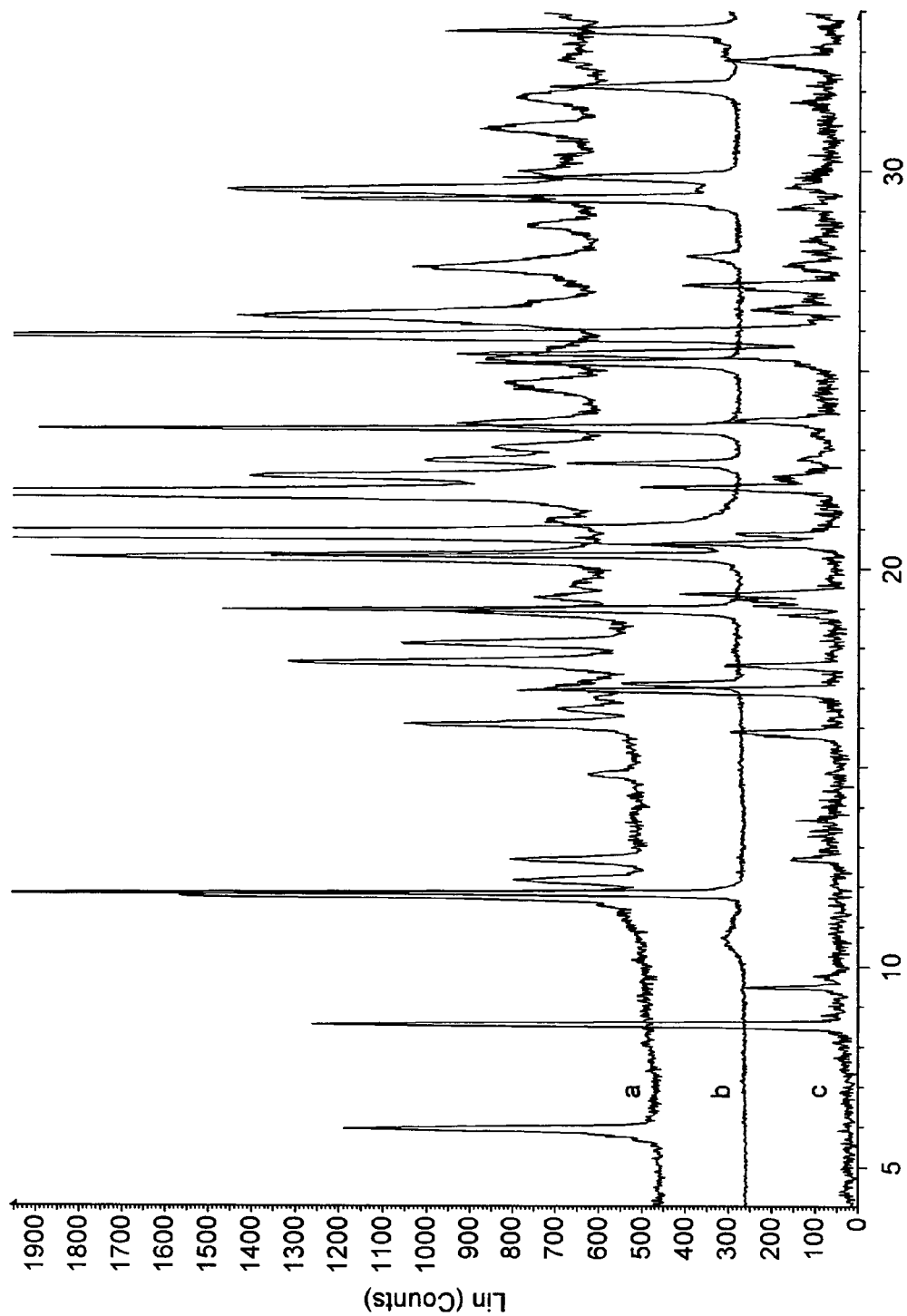
FIG. 17 shows the powder X-Ray diffraction patterns of (a) propiconazole-tartaric acid co-crystal obtained using the technique described in Example 1b, (b) tartaric acid and (c) propiconazole.

In a further embodiment, the co-crystal form of propiconazole and tartaric acid is characterised by a powder X-ray diffraction pattern expressed in terms of 2θ angles, wherein the powder X-ray diffraction pattern comprises at least three 2θ angle values selected from the group comprising 6.0±0.2, 12.0±0.2, 18.0±0.2 and 24.6±0.2. More preferably, the powder X-ray diffraction pattern comprises all of the 2θ angle values listed above. These 2θ angle values are derived from those peaks of the powder X-ray diffraction pattern ascribable purely to the co-crystal; Table 7B comprises these 2θ values as well as values of further peaks which appear in the powder X-ray diffraction pattern of propiconazole and/or tartaric acid as well as the co-crystal. In one embodiment, the co-crystal form of propiconazole and tartaric acid is characterised by a powder X-ray diffraction pattern comprising all the 2θ angle values listed in Table 7B, that is, the powder X-ray diffraction pattern comprises 2θ angle values 6.0±0.2, 11.8±0.2, 12.0±0.2, 12.7±0.2, 16.1±0.2, 17.5±0.2, 18.0±0.2, 19.0±0.2, 20.1±0.2, 21.9±0.2, 22.5±0.2, 24.6±0.2, 26.4±0.2, 27.7±0.2 and 29.6±0.2. All of the peaks are derived from the powder X-ray diffraction pattern of a propiconazole-tartaric acid co-crystal obtained using the method of Example 1e. Table 7B also lists the intensity of these peaks (strong (S), medium (M) or weak (W)). The diffractogram from which all of these peak positions are derived is shown in FIG. 17.

TABLE 7B

| Peak | 2θ | Intensity |
|---|---|---|
| 1 | 6.0 | S |
| 2 | 11.8 | S |
| 3 | 12.0 | M |
| 4 | 12.7 | M |
| 5 | 16.1 | M |
| 6 | 17.5 | S |
| 7 | 18.0 | M |
| 8 | 19.0 | M |
| 9 | 20.1 | S |
| 10 | 21.9 | S |
| 11 | 22.5 | S |
| 12 | 24.6 | W |
| 13 | 26.4 | S |
| 14 | 27.7 | M |
| 15 | 29.6 | S |

It has surprisingly been found that when propiconazole and a co-crystal forming compound are allowed to form co-crystals, the resulting co-crystals give rise to improved properties of the propiconazole as compared to propiconazole in free form. In particular, the co-crystals exhibit a substantially higher melting point than the propiconazole alone (see FIGS. 29 to 41 for the differential scanning calorimetry results for the propiconazole co-crystals of the invention showing these increased melting points). An increased melting point is important as it has benefits during manufacturing, formulation and storage. In particular, these new solid states of propiconazole, which have melting points above the temperature range normally associated with processing and storage, will not undergo melting and recrystallisation events during their formulation and nor will they undergo recrystallisation events during storage of both the technical grade material and the formulated material—the technical material and the formulation will therefore retain their homogeneity. In addition, the higher melting point will allow new solid formulation formats, such as suspension concentrates, suspo-emulsions and wet granulations, to be developed and will lead to potential purity benefits (due to the ability to isolate the solid state rather than a liquid) as well as improved handling characteristics (e.g. reduced toxicity). Finally, mixtures of these new solid states of propiconazole with other active ingredients should show improved stability as potential depression of the melting point by the other active ingredients will not be as crucial.

As used herein 'co-crystal' means a crystalline material which comprises two or more unique components in a stoichiometric ratio each containing distinctive physical characteristics such as structure, melting point and heat of fusion. As used herein, a co-crystal is distinct from a crystalline salt as it consists of neutral components and not charged components as would be found in a salt. The co-crystal can be constructed through several modes of molecular recognition including hydrogen-bonding, Π (pi)-stacking, guest-host complexation and Van-Der-Waals interactions. Of the interactions listed above, hydrogen-bonding is the dominant interaction in the formation of the co-crystal, whereby a non-covalent bond is formed between a hydrogen bond donor of one of the moieties and a hydrogen bond acceptor of the other. Preferred co-crystals of the present invention are those where hydrogen bonding occurs between the co-crystal forming compound and the propiconazole. It is noted that multi-point contacts may be formed in the crystal. For example, two molecules of propiconazole may form contacts with different functional groups on the co-former, or, indeed, there may be multi-point contacts between a single molecule of propiconazole and co-former molecule.

It is noted that hydrogen bonding can result in several different intermolecular assemblies and, as such, the co-crystals of the present invention may exist in one or more polymorphic forms. A polymorphic co-crystal may contain any molar ratio of active ingredient to co-former, but typically will be in the range of 3:1 to 1:3. As the propiconazole exhibits isomerism, a polymorphic form may also contain a different isomeric ratio. This will also be the case when the co-crystal forming compound exhibits isomerism. Each polymorphic form can be defined by one or more solid state analytical techniques including single crystal X-ray diffraction, powder X-ray diffraction, DSC, Raman or Infra-red spectroscopy. In Tables 1, 2, 5, 6 and 7, above, multiple and differing diffraction traces and, consequently, 2θ values, for co-crystals of propiconazole and a specific co-former suggest that these co-crystals may exist in a number of polymorphic forms.

As used herein, the term 'propiconazole' refers to (±)-1-[2-(2,4-dichlorophenyl)-4-propyl-1,3-dioxolan-2-ylmethyl]-1H-1,2,4-triazole, its four sterioisomers (2R, 4S; 2S, 4R; 2R, 4R; 2S, 4S), diastereomeric pairs thereof and mixtures of the diastereomeric pairs. In particular, 'propiconazole' refers to commercially available propiconazole technical material.

Suitably, the molar ratio of propiconazole to co-crystal forming compounds in the co-crystal is in the range of from 3:1 to 1:3. More suitably, the molar ratio of propiconazole to co-crystal forming compounds in the co-crystal is in the range of from 2:1 to 1:1.

The co-crystals of the present invention are formed by contacting the propiconazole with a co-crystal forming compound. This may be done by (i) grinding two solids together, (ii) melting, or partially melting, one or both components and allowing them to recrystallise, (iii) solubilising, or partially solubilising, the propiconazole and adding the co-crystal forming compound or (iv) solubilising, or partially solubilising, the co-crystal forming compound and adding the propiconazole. It may also be possible to solubilise, or partially solubilise, the propiconazole in the co-crystal forming compound and vice versa. Crystallisation is then allowed to occur under suitable conditions. For example, crystallisation may require alteration of a property of the solutions, such as pH or temperature and may require concentration of solute, usually by removal of the solvent and typically by drying the solution. Solvent removal results in the concentration of propiconazole increasing over time so as to facilitate crystallisation. In some cases, microwave irradiation and/or sonication may be used to facilitate crystallisation. Once the solid phase comprising any crystals is formed, this may be tested as described herein.

Accordingly, the present invention provides a process for the production of a co-crystal of propiconazole and a co-crystal forming compound comprising
 (a) grinding, heating or contacting in solution propiconazole with the co-crystal forming compound, under crystallisation conditions so as to form a solid phase;
 (b) isolating co-crystals comprising propiconazole and the co-crystal forming compound.

The co-crystal forming compound for use in the process of the invention is as defined above. In one embodiment of the process, the co-crystal forming compound is selected from the group consisting of 2,2'-dihydroxy-1,1'-dinaphthalene, D-ribose, maleic acid, oxalic acid, tartaric acid, terephthalic acid and trimesic acid.

In a further embodiment of the process, the co-crystal forming compound is selected from the group consisting of terephthalic acid, oxalic acid and trimesic acid.

Assaying the solid phase for the presence of co-crystals of propiconazole and the co-crystal forming compound may be carried out by conventional methods known in the art. For example, it is convenient and routine to use powder X-ray diffraction techniques to assess the presence of the co-crystals. This may be effected by comparing the spectra of the propiconazole, co-crystal forming compound and putative co-crystals in order to establish whether or not true co-crystals have been formed. Other techniques used in an analogous fashion, include differential scanning calorimetry (DSC), thermogravimetric analysis (TGA), Raman and IR spectroscopy, NMR, gas chromatography and HPLC. Single crystal X-ray diffraction is especially useful in identifying co-crystal structures.

The co-crystals of the invention may be readily incorporated into fungicidal compositions (including agrochemical compositions and compositions for use in the protection of industrial materials) by conventional means. Accordingly, the invention also provides a fungicidal composition comprising a co-crystal of propiconazole and the co-crystal forming compound, wherein the co-crystal forming compound is as defined above. In a further embodiment, the fungicidal composition is an agrochemical composition.

The agrochemical compositions comprising the co-crystals of the present invention can be used for the control of plant pathogenic fungi on a number of plant species. Accordingly, the invention also provides a method of preventing/controlling fungal infection on plants or plant propagation material comprising treating the plant or plant propagation material with a fungicidally effective amount of an agricultural composition of the invention. By 'plant propagation material' is meant seeds of all kinds (fruit, tubers, bulbs, grains etc), cuttings, cut shoots and the like.

In particular, the agrochemical compositions of the invention can be used to control, for example, *Cochliobolus sativus, Erysiphe graminis, Leptosphaeria nodorum, Puccinia* spp., *Pyrenophora teres, Pyrenophora tritici-repentis, Rhynchosporium secalis, Septoria* spp, *Mycosphaerella musicola, Mycosphaerella lifiensis* var. *difformis, Sclerotinia homoeocarpa, Rhizoctonia solani, Puccinia* spp., *Erysiphe gramini, Rhizoctonia solani, Helminthosporium oryzae,* dirty panicle complex, *Hemileia vastatrix, Cercospora* spp., *Monilinia* spp., *Podosphaera* spp., *Sphaerotheca* spp., *Tranzschelia* spp. and *Helminthosporium* spp.

The agrochemical compositions of the present invention are suitable for controlling such disease on a number of plants and their propagation material including, but not limited to the following target crops: cereals (wheat, barley, rye, oats, maize (including field corn, pop corn and sweet corn), rice, sorghum and related crops); beet (sugar beet and fodder beet); leguminous plants (beans, lentils, peas, soybeans); oil plants (rape, mustard, sunflowers); cucumber plants (marrows, cucumbers, melons); fibre plants (cotton, flax, hemp, jute); vegetables (spinach, lettuce, asparagus, cabbages, carrots, eggplants, onions, pepper, tomatoes, potatoes, paprika, okra); plantation crops (bananas, fruit trees, rubber trees, tree nurseries), ornamentals (flowers, shrubs, broad-leaved trees and evergreens, such as conifers); as well as other plants such as vines, bushberries (such as blueberries), caneberries, cranberries, peppermint, rhubarb, spearmint, sugar cane and turf grasses including, but not limited to, cool-season turf grasses (for example, bluegrasses (*Poa* L.), such as Kentucky bluegrass (*Poa pratensis* L.), rough bluegrass (*Poa trivialis* L.), Canada bluegrass (*Poa compressa* L.) and annual bluegrass (*Poa annua* L.); bentgrasses (*Agrostis* L.), such as creeping bentgrass (*Agrostis palustris* Huds.), colonial bentgrass (*Agrostis tenius* Sibth.), velvet bentgrass (*Agrostis canina* L.) and redtop (*Agrostis alba* L.); fescues (Festuca L.), such as tall fescue (*Festuca arundinacea* Schreb.), meadow fescue (*Festuca elatior* L.) and fine fescues such as creeping red fescue (*Festuca rubra* L.), chewings fescue (*Festuca rubra* var. *commutata* Gaud.), sheep fescue (*Festuca ovina* L.) and hard fescue (*Festuca longifolia*); and ryegrasses (Lolium L.), such as perennial ryegrass (*Lolium perenne* L.) and annual (Italian) ryegrass (*Lolium multiflorum* Lam.)) and warm-season turf grasses (for example, Bermudagrasses (*Cynodon* L. C. Rich), including hybrid and common Bermudagrass; Zoysiagrasses (*Zoysia Willd.*), St. Augustinegrass (*Stenotaphrum secundatum* (Walt.) Kuntze); and centipedegrass (*Eremochloa ophiuroides* (Munro.) Hack.)).

In addition 'crops' are to be understood to include those crops that have been made tolerant to pests and pesticides, including herbicides or classes of herbicides, as a result of conventional methods of breeding or genetic engineering. Tolerance to e.g. herbicides means a reduced susceptibility to damage caused by a particular herbicide compared to conventional crop breeds. Crops can be modified or bred so as to be tolerant, for example, to HPPD inhibitors such as mesotrione or EPSPS inhibitors such as glyphosate.

The rate at which the agrochemical composition of the invention is applied will depend upon the particular type of fungus to be controlled, the degree of control required and the timing and method of application. In general, the compositions of the invention can be applied at an application rate of between 0.005 kilograms/hectare (kg/ha) and about 5.0 kg/ha, based on the total amount of active propiconazole in the composition. An application rate of between about 0.1 kg/ha and about 3.0 kg/ha is preferred, with an application rate of between about 0.2 kg/ha and 1 kg/ha being especially preferred.

In practice, the agrochemical compositions comprising the co-crystals of the invention are applied as a formulation containing the various adjuvants and carriers known to or used in the industry. They may thus be formulated as granules, as wettable powders; as emulsifiable concentrates, as suspension concentrates, as powders or dusts, as flowables, as solutions, as suspensions or emulsions or suspo-emulsions, or as controlled release forms such as microcapsules. Suitably, the agrochemical composition of the invention may be formulated as a suspension concentrate, a suspo-emulsion or a wet granulation. These formulations are described in more detail below and may contain as little as about 0.5% to as much as about 95% or more by weight of the active ingredient in the form of the co-crystal. The optimum amount will depend on formulation, application equipment and nature of the plant pathogenic fungi to be controlled.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Suspension concentrates are formulations in which finely divided solid particles of the active compound are stably suspended. The solid particles may be suspended in an aqueous solution or in an oil (as an oil dispersion). Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from about 0.5% to about 95% of the concentrate.

Granular formulations include both extrudates and relatively coarse particles and may be applied without dilution to the area in which control of plant pathogenic fungi is required or dispersed in a spray tank before application, for example. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations for use without dilution normally contain about 5% to about 25% active ingredients which may include surface-active agents such as heavy aromatic naphthas, kerosene and other petroleum fractions, or vegetable oils; and/or stickers such as dextrins, glue or synthetic resins. When the granules are to be dispersed in a spray tank before application, the active ingredient content may be increased up to 80%.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimeter to 1 centimeter and preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Many of the formulations described above include wetting, dispersing or emulsifying agents. Examples are alkyl and alkylaryl sulphonates and sulphates and their salts, polyhydric alcohols; polyethoxylated alcohols, esters and fatty amines. These agents, when used, normally comprise from 0.1% to 15% by weight of the formulation.

Suitable agricultural adjuvants and carriers that are useful in formulating the compositions of the invention in the formulation types described above are well known to those skilled in the art. Suitable examples of the different classes are found in the non-limiting list below.

Liquid carriers that can be employed include water and any solvents in which the co-crystal has no or limited solubility e.g. toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaceous earth, lime, calcium carbonate, bentonite clay, fuller's earth, cotton seed hulls, wheat flour, soybean flour, pumice, wood flour, walnut shell flour, lignin and the like.

A broad range of surface-active agents are advantageously employed in both said liquid and solid compositions, especially those designed to be diluted with carrier before application. The surface-active agents can be anionic, cationic, non-ionic or polymeric in character and can be employed as emulsifying agents, wetting agents, suspending agents or for other purposes. Typical surface active agents include salts of alkyl sulphates, such as diethanolammonium lauryl sulphate; alkylarylsulphonate salts, such as calcium dodecylbenzenesulphonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulphonate salts, such as sodium dibutylnaphthalenesulphonate; dialkyl esters of sulphosuccinate salts, such as sodium di(2-ethylhexyl) sulphosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants, sticking agents, and the like.

In addition, further, other biocidally active ingredients or compositions may be combined with the agrochemical composition of this invention. For example, the compositions may contain other fungicides, herbicides, insecticides, bactericides, acaricides, nematicides and/or plant growth regulators, in order to broaden the spectrum of activity or in order to reduce the risk of resistance developing.

Each of the above formulations can be prepared as a package containing the fungicides together with other ingredients of the formulation (diluents, emulsifiers, surfactants, etc.). The formulations can also be prepared by a tank mix method, in which the ingredients are obtained separately and combined at the grower site.

These formulations can be applied to the areas where control is desired by conventional methods. Dust and liquid compositions, for example, can be applied by the use of power-dusters, broom and hand sprayers and spray dusters. The formulations can also be applied from airplanes as a dust or a spray or by rope wick applications. Both solid and liquid formulations may also be applied to the soil in the locus of the plant to be treated allowing the active ingredient to penetrate the plant through the roots. The formulations of the invention may also be used for dressing applications on plant propagation material to provide protection against fungus infections on the plant propagation material as well as against phytopathogenic fungi occurring in the soil. Suitably, the active ingredient may be applied to plant propagation material to be protected by impregnating the plant propagation material, in particular, seeds, either with a liquid formulation of the fungicide or coating it with a solid formulation. In special cases, other types of application are also possible, for example, the specific treatment of plant cuttings or twigs serving propagation.

Suitably, the agrochemical compositions and formulations of the present invention are applied prior to disease development. Rates and frequency of use of the formulations are those conventionally used in the art and will depend on the risk of infestation by the fungal pathogen.

The compositions of the invention can also be used for the protection of industrial materials. In a still further aspect of the invention there is thus provided a method for the protection of industrial material from fungal attack comprising treating the industrial material with a composition comprising the co-crystal of the invention. In a further aspect, the present invention provides the use of a composition which comprises the co-crystal of the invention for the protection of industrial materials. In a particular embodiment said industrial material is selected from the group consisting of: wood; plastic; wood plastic composite; paint; paper; and wallboards.

"Industrial material" includes, but is not limited to, those materials used in construction and the like. For example, industrial material may be structural timber, doors, cupboards, storage units, carpets, particularly natural fibre carpets such as wool and hessian, plastics, wood (including engineered wood) and wood plastic composite.

In a particular embodiment the industrial material is a coating. "Coating" includes, but is not limited to, compositions applied to a substrate, for example, paints, stains, varnishes, lacquers, primers, semi gloss coatings, gloss coatings, flat coatings, topcoats, stain-blocking coatings, penetrating sealers for porous substrates, concrete, and marble, elastomeric coatings, mastics, caulks, and sealants, board and panelling coatings, transportation coatings, furniture coatings, and coil coatings, bridge and tank coatings and surface marking paints, leather coatings and treatments, floor care coatings, paper coatings, personal care coatings such as for hair, skin, nails, woven and nonwoven fabric coatings and pigment printing pastes, and adhesive coatings such as, for example, pressure sensitive adhesives and wet- and dry-laminating adhesives and plaster.

In particular embodiment coating means paint; varnish; stain, lacquer or plaster. In a further embodiment said coating is a lacquer. In a specific embodiment coating means paint. Paint can comprise, for example, a film former and a carrier (which carrier can be water and/or an organic solvent) and optionally a pigment.

In addition to this, industrial material includes adhesives, sealants, joining materials and joints and insulation material. In a particular embodiment "industrial material" means structural timber. In a further embodiment "industrial material" means engineered wood. In a further embodiment "industrial material" means plastic.

Plastics includes plastic polymers and copolymers, including: acrylonitrile butadiene styrene, butyl rubber, epoxies, fluoropolymers, isoprene, nylons, polyethylene, polyurethane, polypropylene, polyvinyl chloride, polystyrene, polycarbonate, polyvinylidene fluoride, polyacrylate, polymethyl methacrylate, polyurethane, polybutylene, polybutylene terephthalate, polyether sulphone, polyphenyllenoxide, polyphenylene ether, polyphenylene sulphide, polyphtata-mide, polysulphene, polyester, silicone, styrene butadiene rubber and combinations of polymers. In a further embodiment "industrial material" means polyvinyl chloride (PVC). In a further embodiment "industrial material" means polyurethane (PU). In a further embodiment "industrial material" means wood plastic composite (WPC). Wood plastic composite is a material that is well known in the art. A review of WPCs can be found in the following publication—Craig Clemons—Forrest Products Journal. June 2002 Vol 52. No. 6. pp 10-18.

"Wood" is to be understood as meaning wood and wood products, for example: derived timber products, lumber, plywood, chipboard, flakeboard, laminated beams, oriented strandboard, hardboard, and particleboard, tropical wood, structural timber, wooden beams, railway sleepers, components of bridges, jetties, vehicles made of wood, boxes, pallets, containers, telegraph-poles, wooden fences, wooden lagging, windows and doors made of wood, plywood, chipboard, joinery, or wooden products which are used, quite generally, for building houses or decks, in building joinery or wood products that are generally used in house-building including engineered wood, construction and carpentry.

"Industrial material" also includes cooling lubricants and cooling and heating systems, ventilation and air conditioning systems and parts of production plants, for example cooling-water circuits.

"Industrial material" also includes wallboards such as gypsum based wallboards.

In a still further aspect of the invention there is provided an industrial material comprising a composition which comprises a co-crystal of the invention. In a particular embodiment said industrial materials are selected from the group consisting of wood, plastic, wood plastic composite, paint, paper and wallboards. In a particular embodiment said industrial materials comprise wood.

The industrial material can be treated with a composition according to the invention in a number of ways, including, but not limited to, by including the composition in the industrial material itself, absorbing, impregnating, treating (in closed pressure or vacuum systems) said material with said composition, dipping or soaking the building material, or coating the building material for example by curtain coating, roller, brush, spray, atomisation, dusting, scattering or pouring application. The composition of the invention can be formulated for use in treatment of industrial materials by using techniques well known to the person skilled in the art. Such formulations may utilise, for example, the formulation materials listed above in relation to agrochemical formulations.

The present invention will now be described by way of the following non-limiting examples and figures, wherein:

FIG. 1 shows the powder X-Ray diffraction patterns of (a) propiconazole-2,2'-dihydroxy-1,1'-dinaphthalene co-crystal obtained using the technique described in Example 1b, (b) 2,2'-dihydroxy-1,1'-dinaphthalene and (c) propiconazole.

Figure 2:
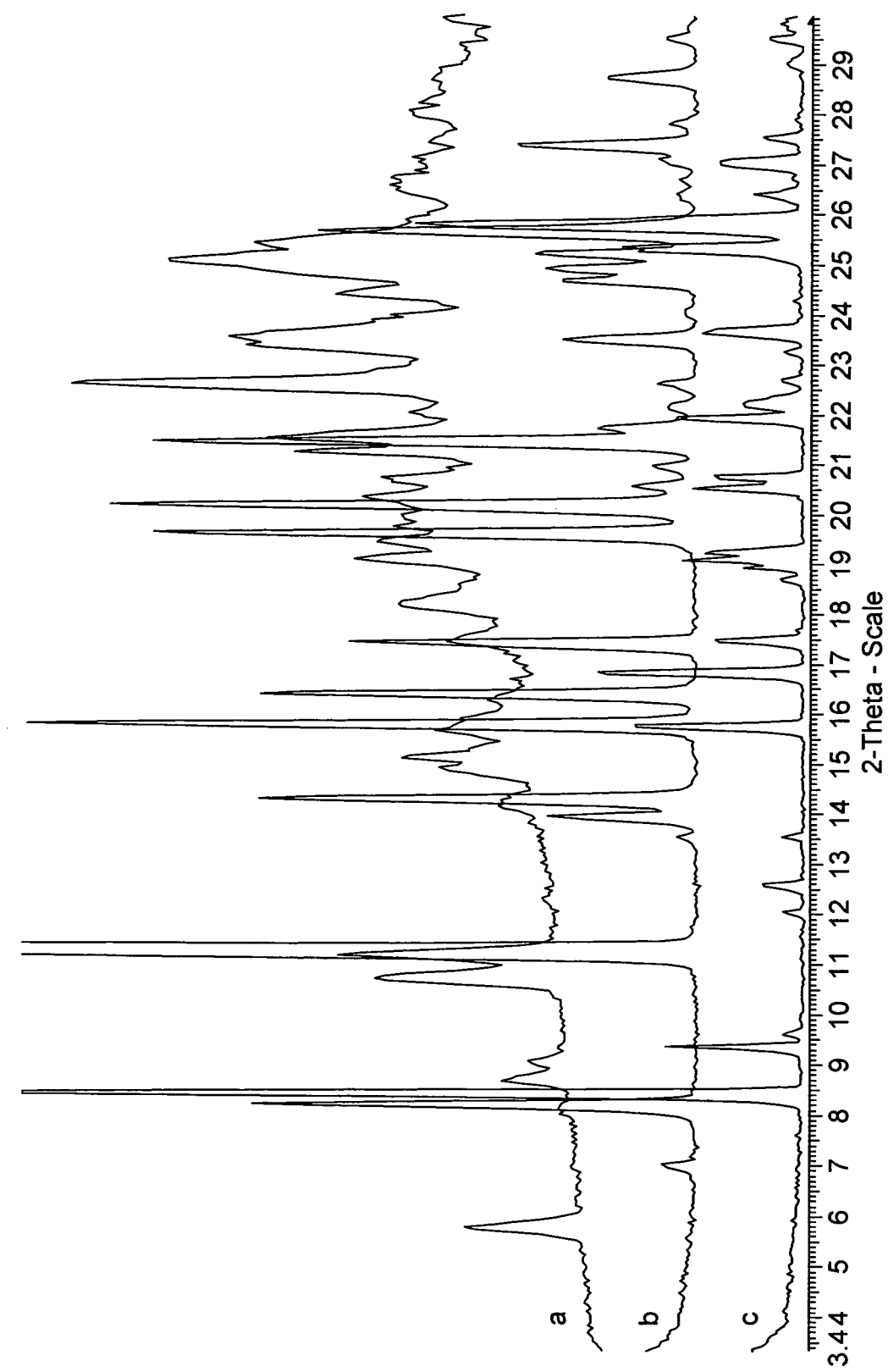
FIG. 2 shows the powder X-Ray diffraction patterns of (a) propiconazole-2,2'-dihydroxy-1,1'-dinaphthalene co-crystal obtained using the technique described in Example 1c, (b) 2,2'-dihydroxy-1,1'-dinaphthalene and (c) propiconazole.

FIG. 2 shows the powder X-Ray diffraction patterns of (a) propiconazole-2,2'-dihydroxy-1,1'-dinaphthalene co-crystal obtained using the technique described in Example 1c, (b) 2,2'-dihydroxy-1,1'-dinaphthalene and (c) propiconazole.

FIG. 3 shows the powder X-Ray diffraction patterns of (a) propiconazole-D-ribose co-crystal obtained using the technique described in Example 1a, (b) D-ribose and (c) propiconazole.

Figure 4:
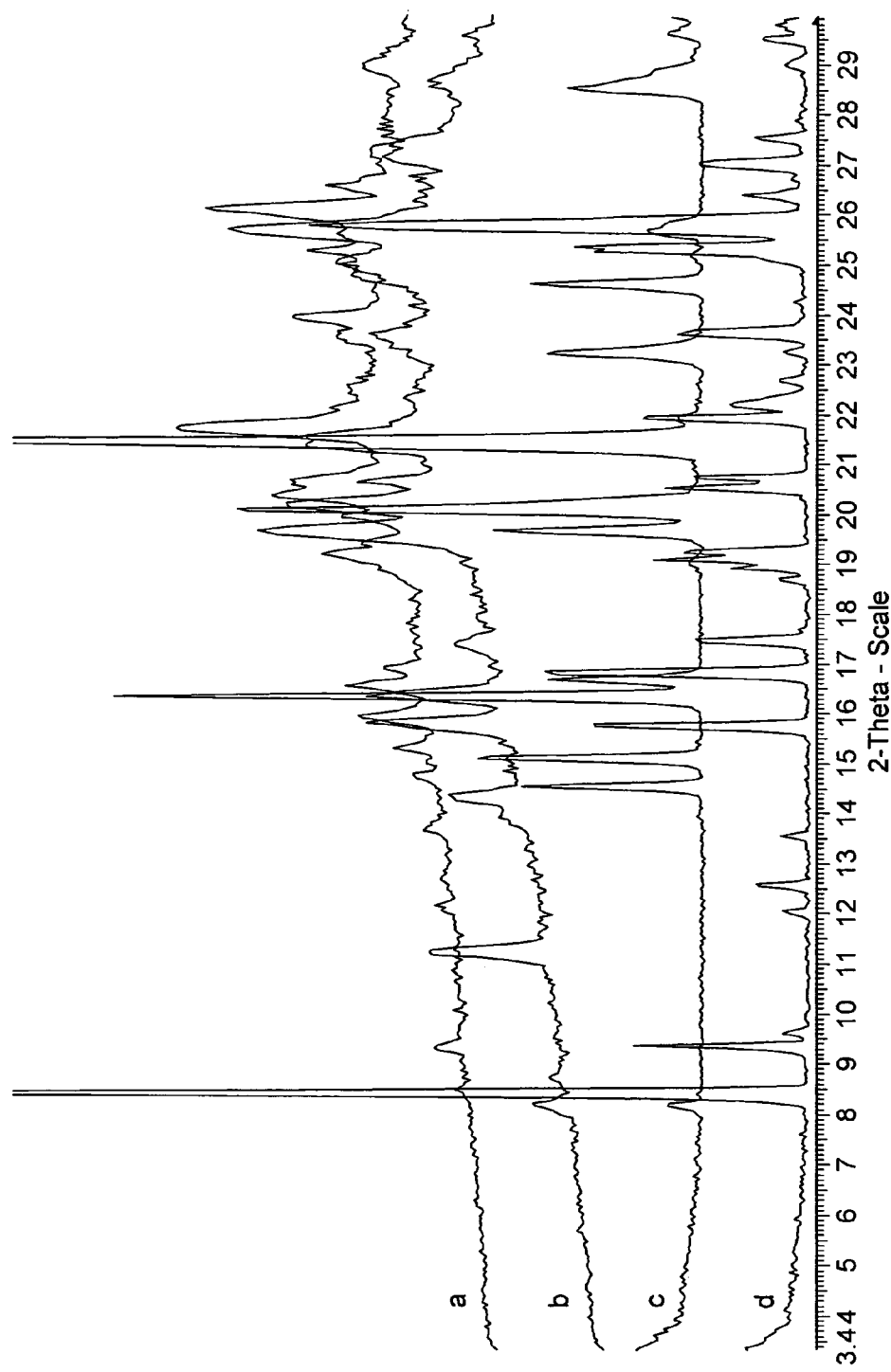
FIG. 4 shows the powder X-Ray diffraction patterns of (a) propiconazole-D-ribose co-crystal obtained using the technique described in Example 1c, (b) propiconazole-D-ribose co-crystal obtained using the technique described in Example 1d, (c) D-ribose and (d) propiconazole.

FIG. 4 shows the powder X-Ray diffraction patterns of (a) propiconazole-D-ribose co-crystal obtained using the technique described in Example 1c, (b) propiconazole-D-ribose co-crystal obtained using the technique described in Example 1d, (c) D-ribose and (d) propiconazole.

FIG. 5 shows the powder X-Ray diffraction patterns of (a) propiconazole-trimesic acid co-crystal obtained using the technique described in Example 1a, (b) trimesic acid and (c) propiconazole.

FIG. 6 shows the powder X-Ray diffraction patterns of (a) propiconazole-terephthalic acid co-crystal obtained using the technique described in Example 1b, (b) terephthalic acid and (c) propiconazole.

FIG. 7 shows the powder X-Ray diffraction patterns of (a) propiconazole-terephthalic acid co-crystal obtained using the technique described in Example 1g, (b) terephthalic acid and (c) propiconazole.

FIG. 8 shows the powder X-Ray diffraction patterns of (a) propiconazole-maleic acid co-crystal obtained using the technique described in Example 1b after subjection to chemical stability analysis, (b) propiconazole-maleic acid co-crystal obtained using the technique described in Example 1b before subjection to chemical stability analysis, (c) maleic acid and (d) propiconazole.

Figure 9:
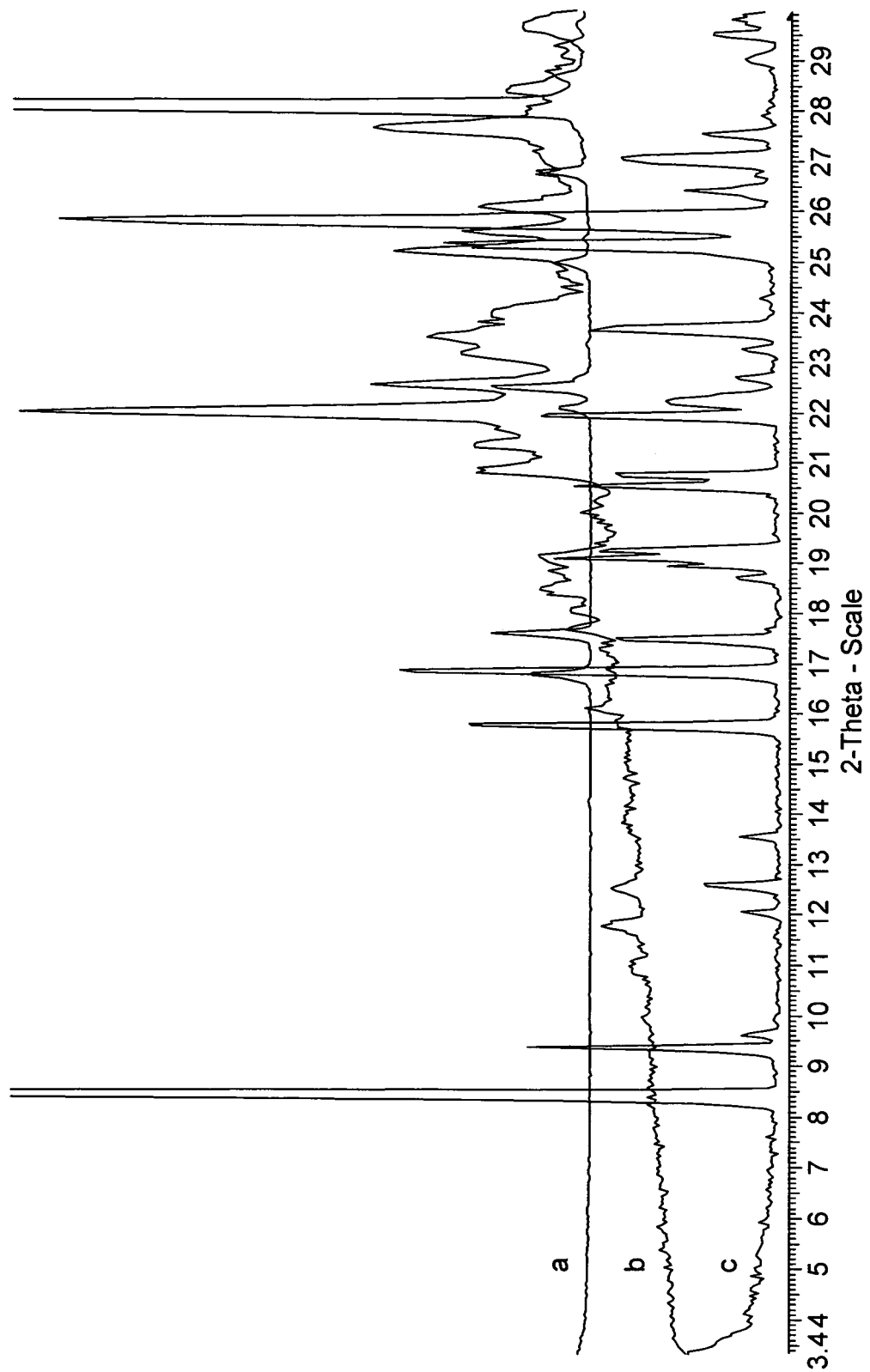
FIG. 9 shows the powder X-Ray diffraction patterns of (a) propiconazole-maleic acid co-crystal obtained using the technique described in Example 1c, (b) maleic acid and (c) propiconazole.

FIG. 9 shows the powder X-Ray diffraction patterns of (a) propiconazole-maleic acid co-crystal obtained using the technique described in Example 1c, (b) maleic acid and (c) propiconazole.

Figure 10:
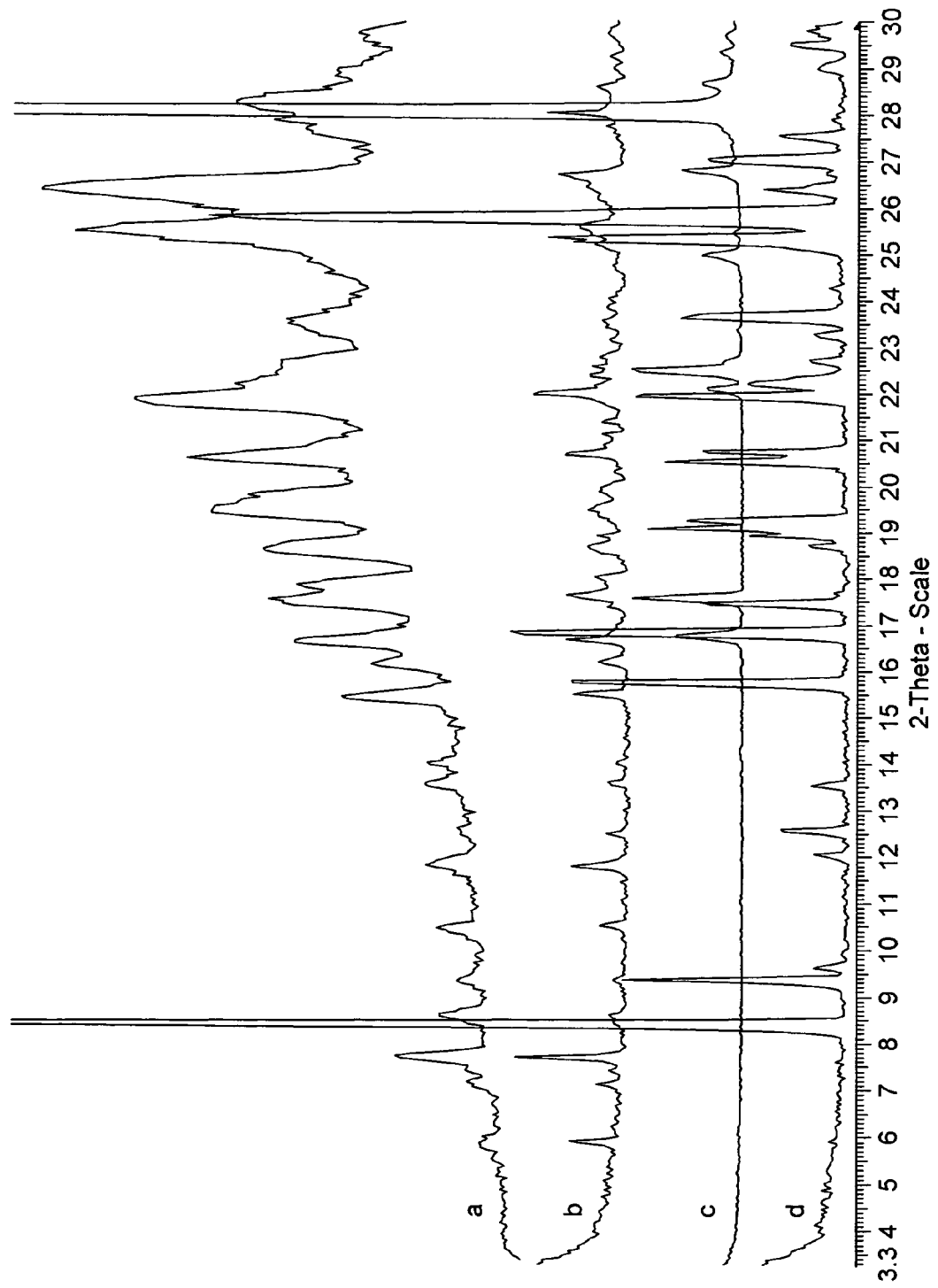
FIG. 10 shows the powder X-Ray diffraction patterns of (a) propiconazole-maleic acid co-crystal obtained using the technique described in Example 1b after subjection to chemical stability analysis, (b) propiconazole-maleic acid co-crystal obtained using the technique described in Example 1b before subjection to chemical stability analysis, (c) maleic acid and (d) propiconazole.

FIG. 10 shows the powder X-Ray diffraction patterns of (a) propiconazole-maleic acid co-crystal obtained using the technique described in Example 1b after subjection to chemical stability analysis, (b) propiconazole-maleic acid co-crystal obtained using the technique described in Example 1b before subjection to chemical stability analysis, (c) maleic acid and (d) propiconazole.

FIG. 11 shows the powder X-Ray diffraction patterns of (a) propiconazole-oxalic acid co-crystal obtained using the technique described in Example 1a, (b) oxalic acid and (c) propiconazole.

Figure 12:
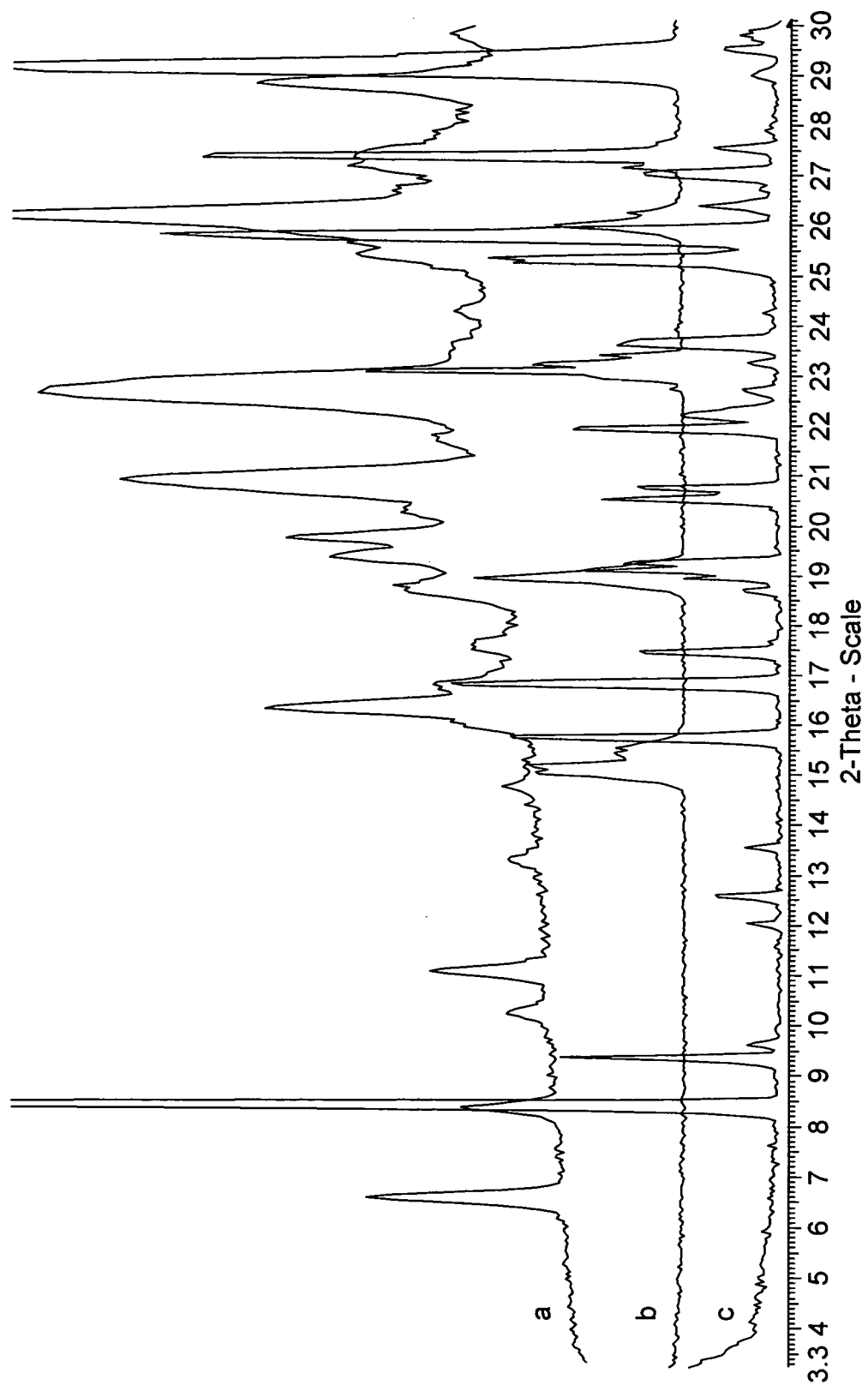
FIG. 12 shows the powder X-Ray diffraction patterns of (a) propiconazole-oxalic acid co-crystal obtained using the technique described in Example 1a, (b) oxalic acid and (c) propiconazole.

FIG. 12 shows the powder X-Ray diffraction patterns of (a) propiconazole-oxalic acid co-crystal obtained using the technique described in Example 1b, (b) oxalic acid and (c) propiconazole.

Figure 13:
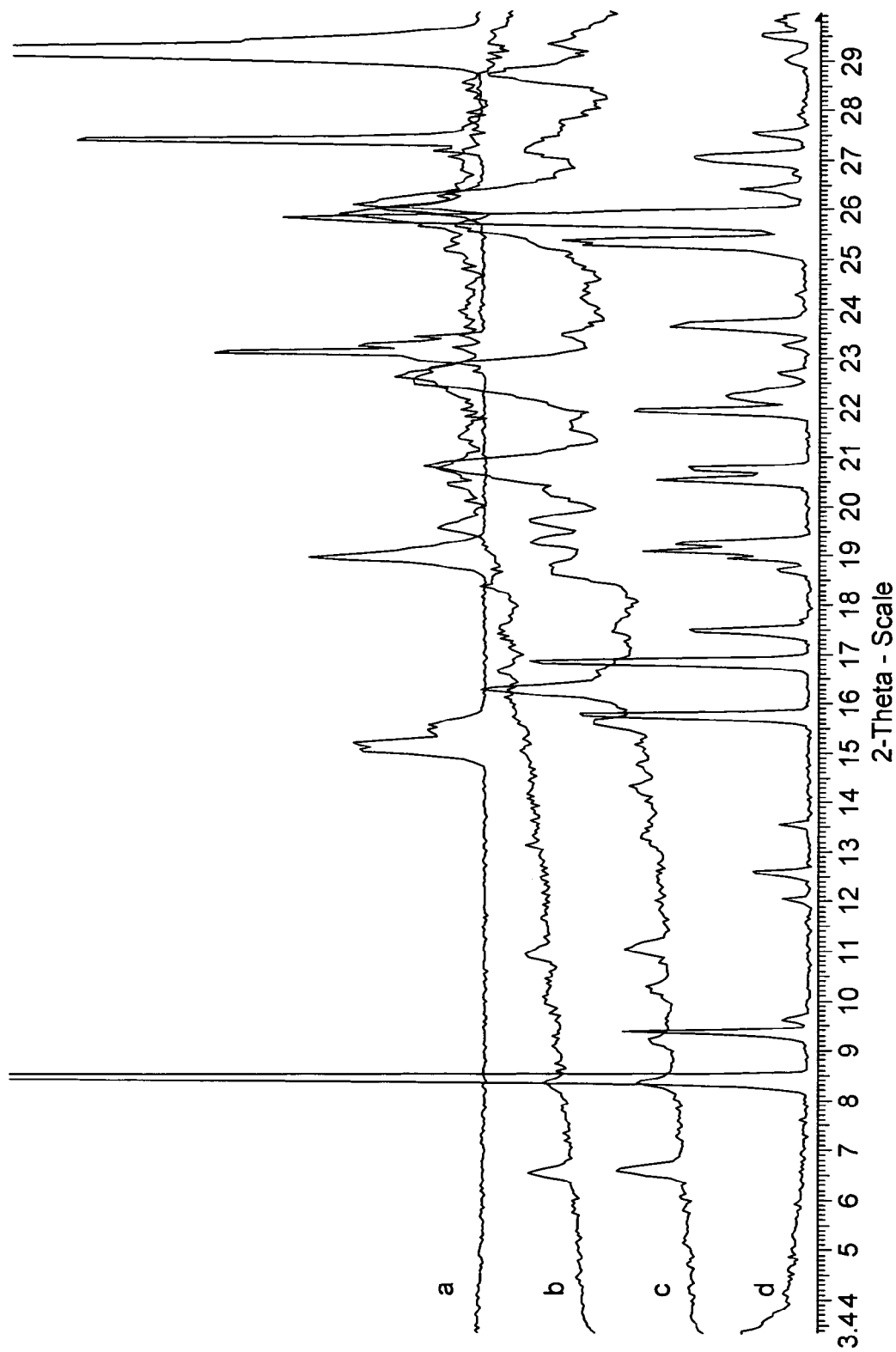
FIG. 13 shows the powder X-Ray diffraction patterns of (a) propiconazole-oxalic acid co-crystal obtained using the technique described in Example 1b, (b) oxalic acid and (c) propiconazole.

FIG. 13 shows the powder X-Ray diffraction patterns of (a) oxalic acid, (b) propiconazole-oxalic acid co-crystal obtained using the technique described in Example 1c, (c) propiconazole-oxalic acid co-crystal obtained using the technique described in Example 1d and (d) propiconazole.

FIG. 14 shows the powder X-Ray diffraction patterns of (a) propiconazole-oxalic acid co-crystals obtained using the technique described in Example 1f, (b) oxalic acid and (c) propiconazole.

FIG. 15 shows the powder X-Ray diffraction patterns of (a) propiconazole-tartaric acid co-crystal obtained using the technique described in Example 1a, (b) tartaric acid and (c) propiconazole.

FIG. 16 shows the powder X-Ray diffraction patterns of (a) propiconazole-tartaric acid co-crystal obtained using the technique described in Example 1b, (b) tartaric acid and (c) propiconazole.

FIG. 17 shows the powder X-Ray diffraction patterns of (a) propiconazole-tartaric acid co-crystal obtained using the technique described in Example 1e, (b) tartaric acid and (c) propiconazole.

Figure 18:
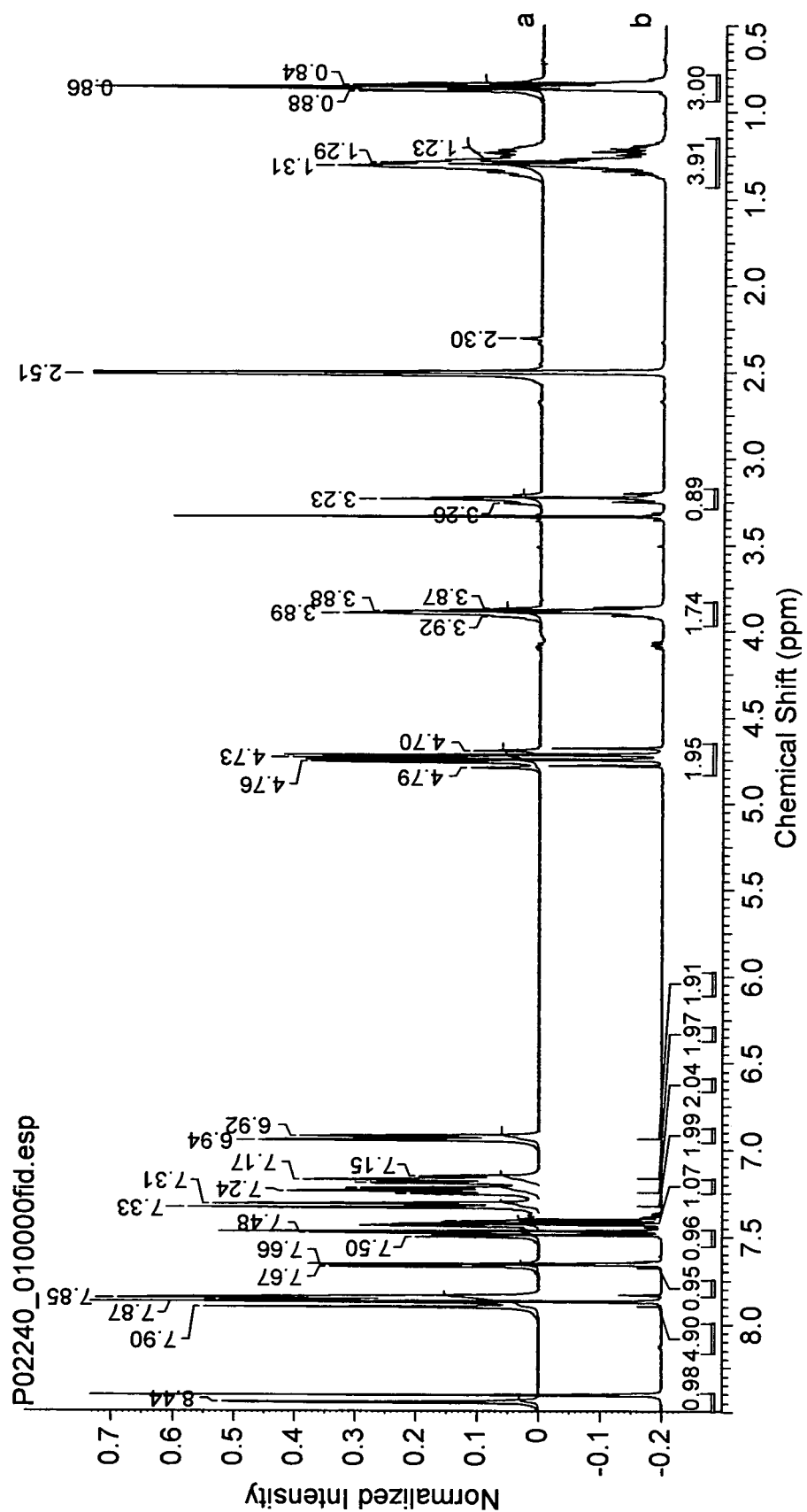
FIG. 18 shows the powder X-Ray diffraction patterns of (a) propiconazole-sucrose co-crystal obtained using the technique described in Example 1a, (b) sucrose and (c) propiconazole.

FIG. 18 shows NMR analysis of (a) propiconazole-2,2'-dihydroxy-1,1'-dinaphthalene co-crystal obtained using the technique described in Example 1b and (b) propiconazole.

Figure 19:
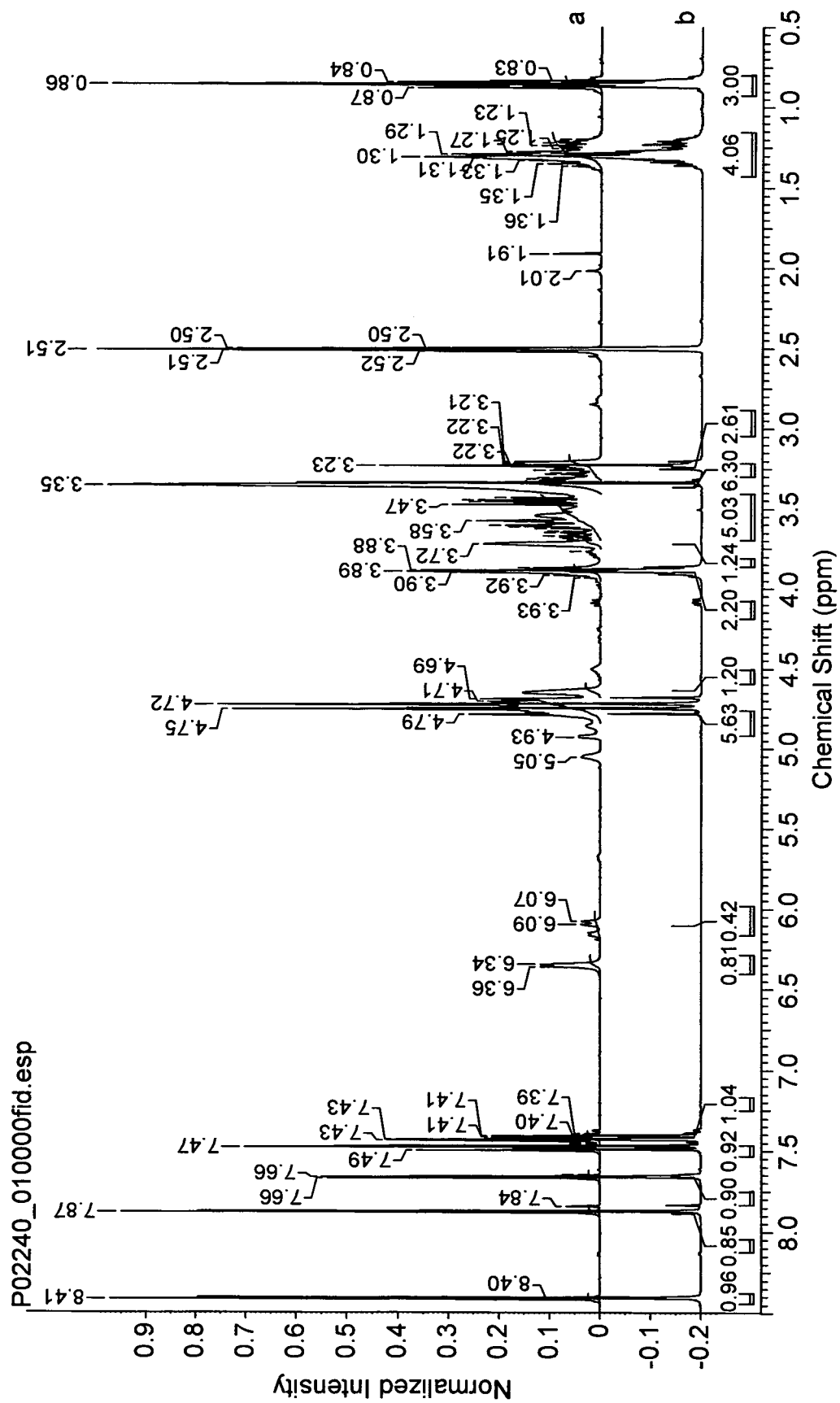
FIG. 19 shows the powder X-Ray diffraction patterns of (a) propiconazole-trehalose co-crystal obtained using the technique described in Example 1a (Batch 1), (b) propiconazole-trehalose co-crystal obtained using the technique described in Example 1a (Batch 2), (c) trehalose and (d) propiconazole.

FIG. 19 shows NMR analysis of (a) propiconazole-D-ribose co-crystal obtained using the technique described in Example 1a and (b) propiconazole.

Figure 20:
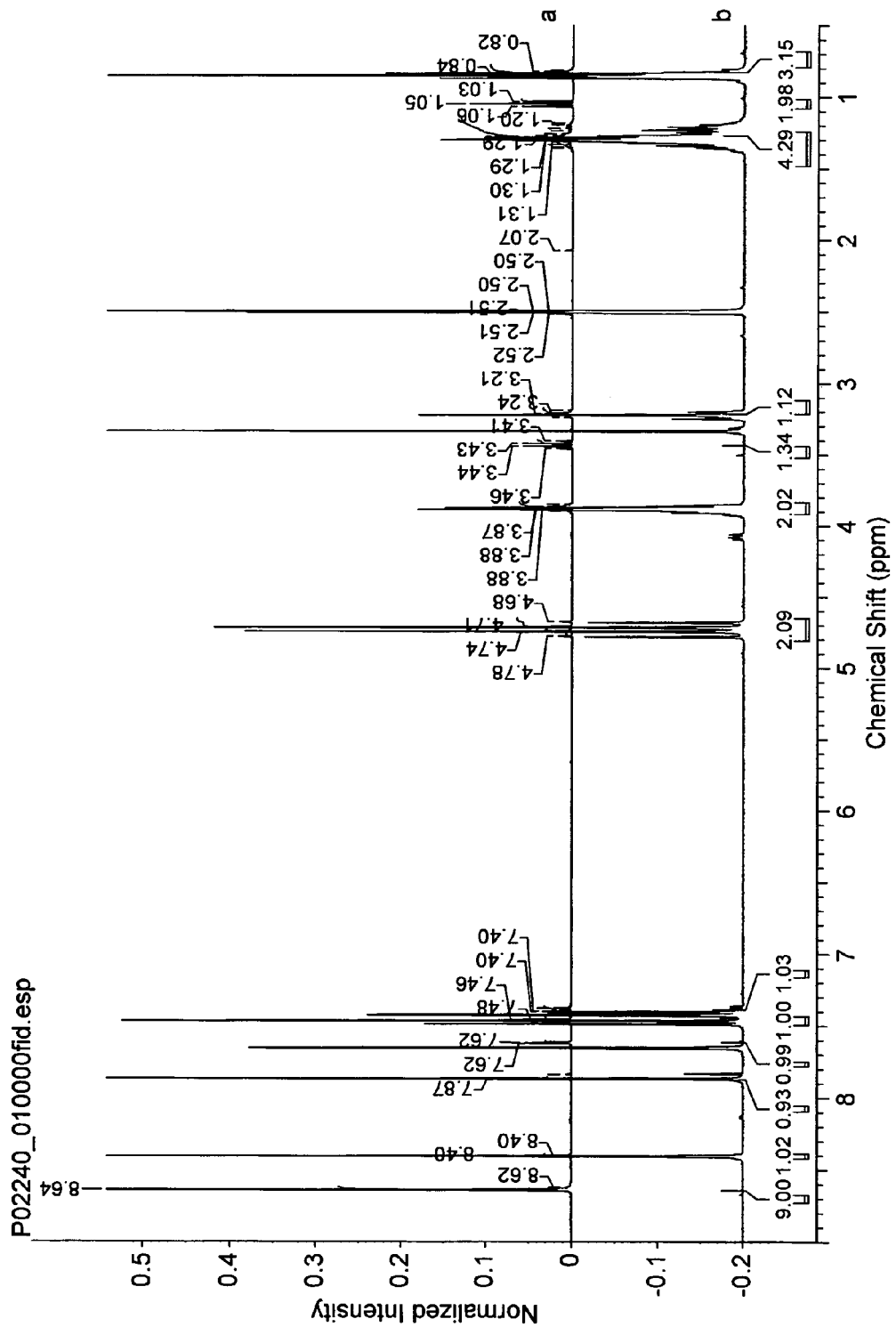
FIG. 20 shows the powder X-Ray diffraction patterns of (a) propiconazole-sorbic acid co-crystal obtained using the technique described in Example 1c, (b) propiconazole-sorbic acid co-crystal obtained using the technique described in Example 1d, (c) sorbic acid and (d) propiconazole.

FIG. 20 shows NMR analysis of (a) propiconazole-trimesic acid co-crystal obtained using the technique described in Example 1a and (b) propiconazole.

Figure 21:
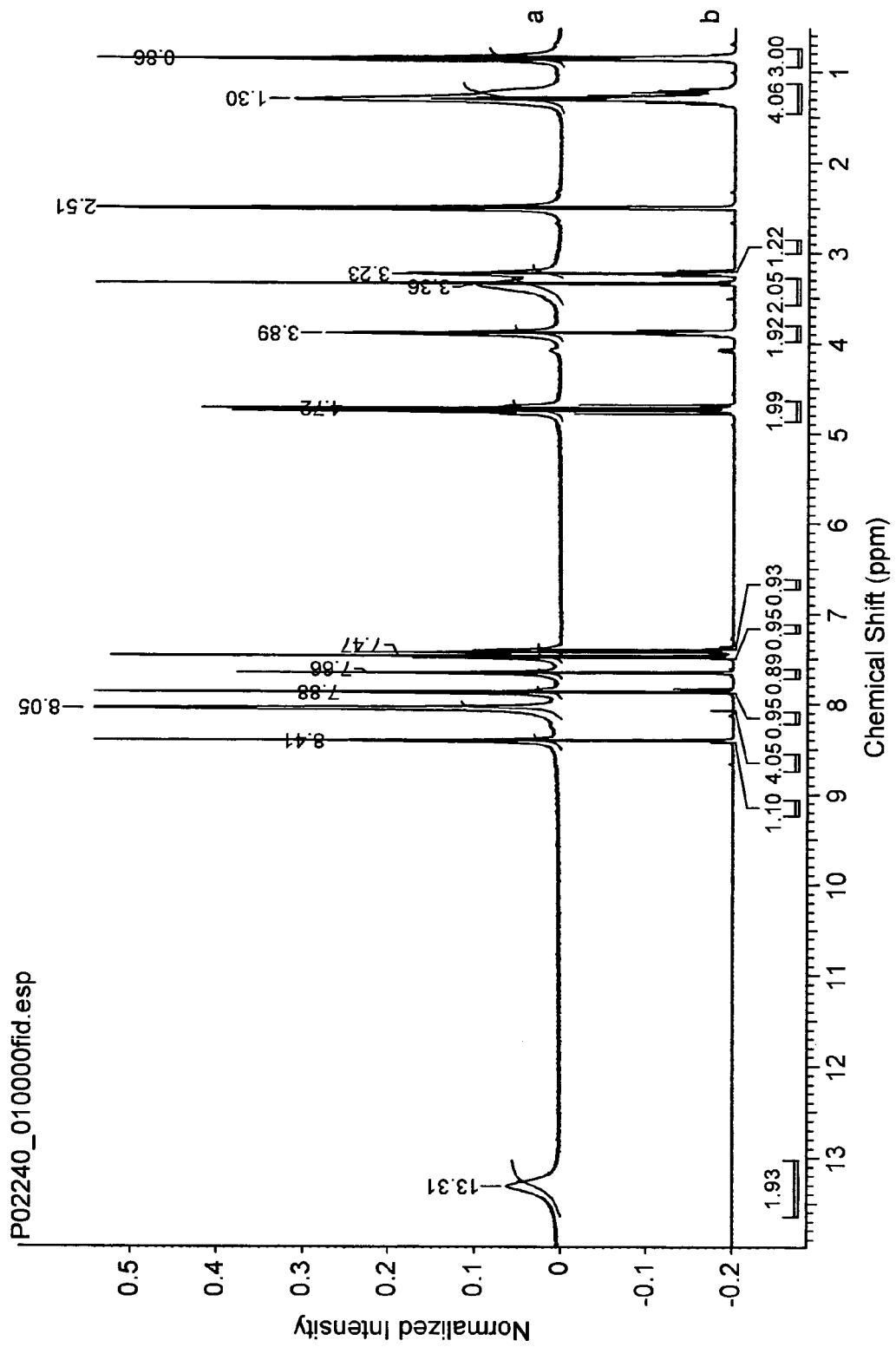
FIG. 21 shows the powder X-Ray diffraction patterns of (a) propiconazole-1,3,5-cyclohexanetriol co-crystal obtained using the technique described in Example 1c, (b) propiconazole-1,3,5-cyclohexanetriol co-crystal obtained using the technique described in Example 1d, (c) 1,3,5-cyclohexanetriol and (d) propiconazole.

FIG. 21 shows NMR analysis of (a) propiconazole-terephthalic acid co-crystal obtained using the technique described in Example 1b and (b) propiconazole.

Figure 22:
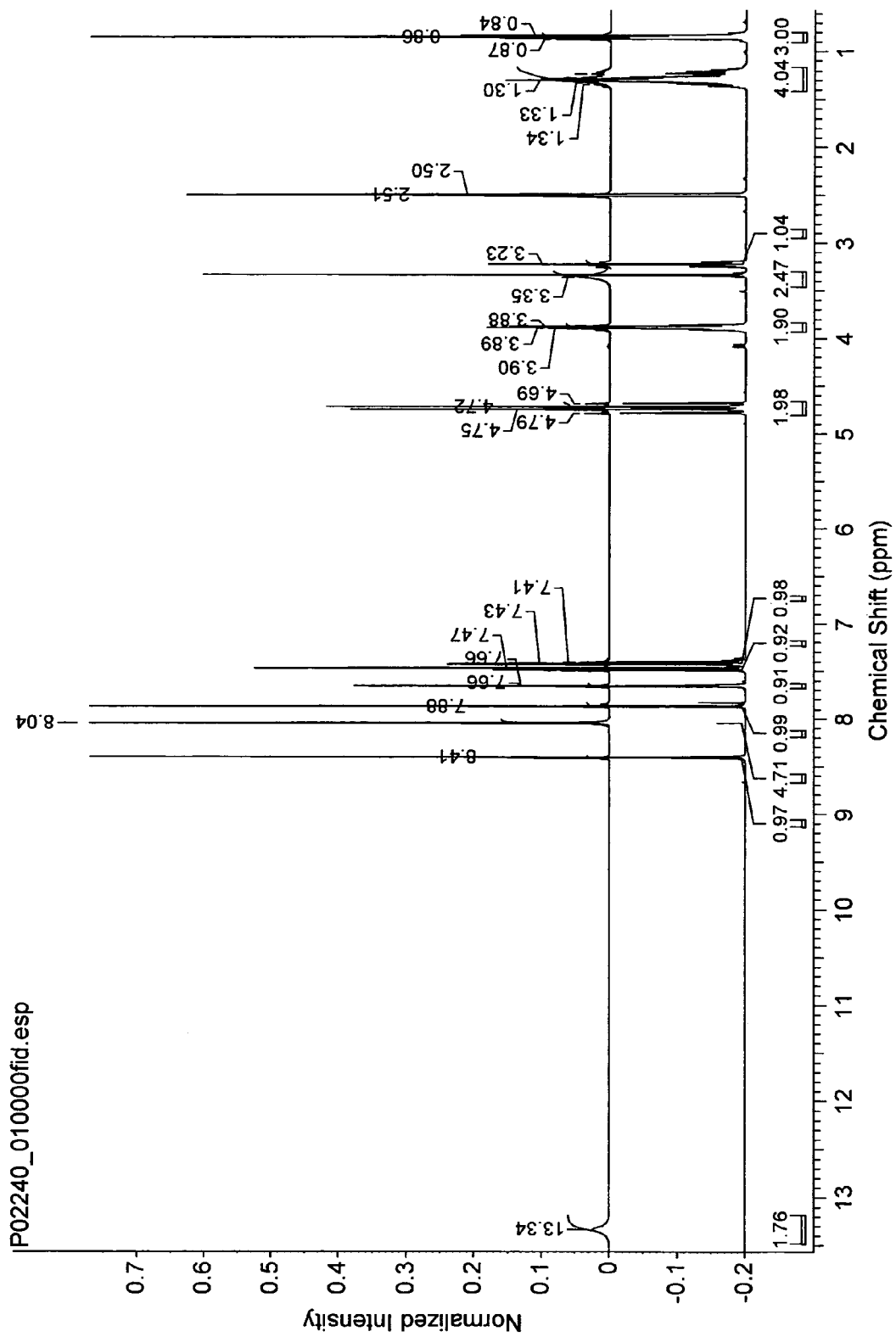
FIG. 22 shows the powder X-Ray diffraction patterns of (a) propiconazole-trans-1,4-diaminocyclohexane co-crystal obtained using the technique described in Example 1d, (b) trans-1,4-diaminocyclohexane and (c) propiconazole.

FIG. 22 shows NMR analysis of (a) propiconazole-terephthalic acid co-crystal obtained using the technique described in Example 1g and (b) propiconazole.

Figure 23:
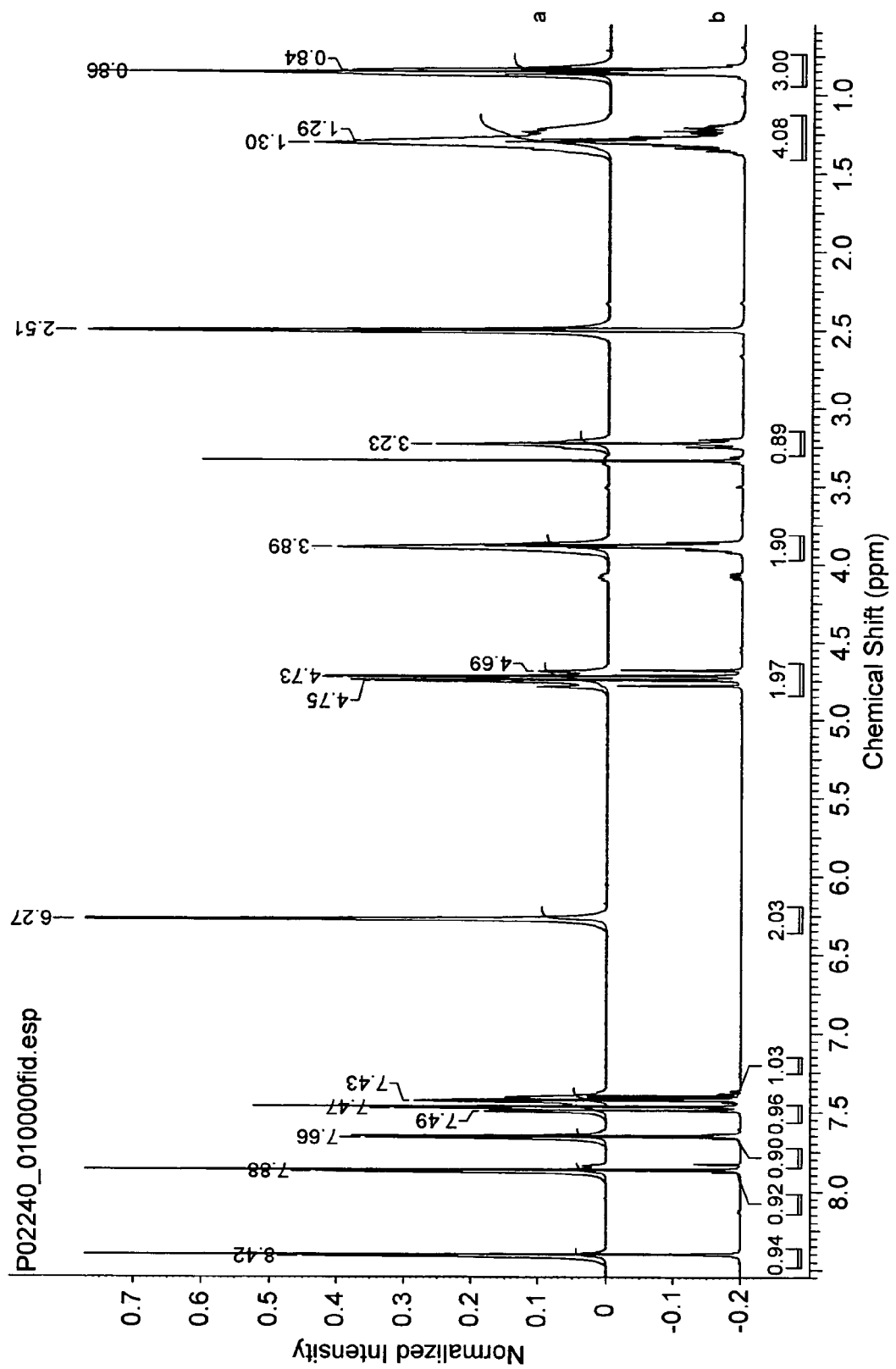
FIG. 23 shows the powder X-Ray diffraction patterns of (a) propiconazole-proline co-crystal obtained using the technique described in Example 1c, (b) proline and (c) propiconazole.

FIG. 23 shows NMR analysis of (a) propiconazole-maleic acid co-crystal obtained using the technique described in Example 1b and (b) propiconazole.

Figure 24:
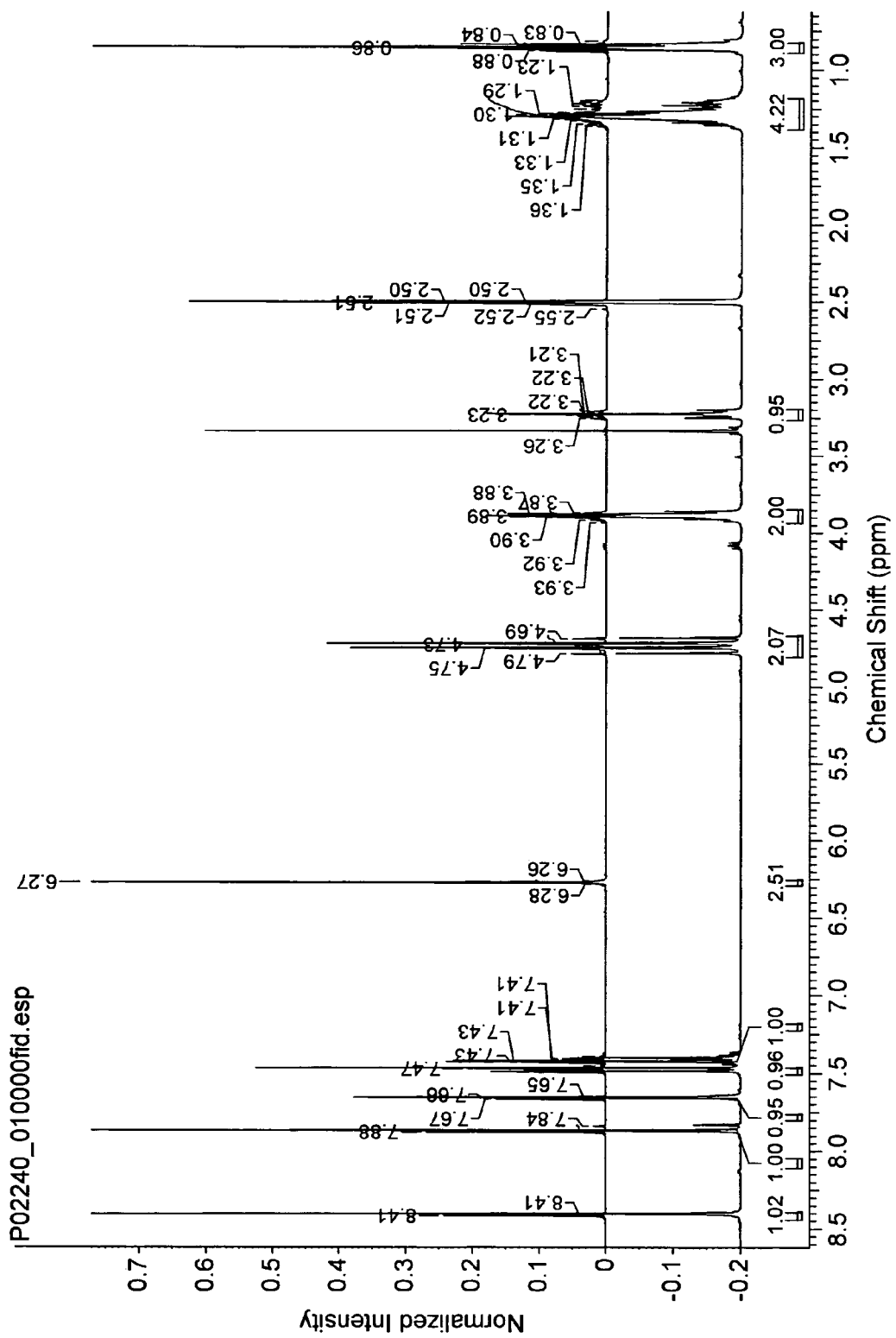
FIG. 24 shows the powder X-Ray diffraction patterns of (a) propiconazole-phenylalanine co-crystal obtained using the technique described in Example 1c, (b) phenylalanine and (c) propiconazole.

FIG. 24 shows NMR analysis of (a) propiconazole-maleic acid co-crystal obtained using the technique described in Example 1b and (b) propiconazole.

Figure 25:
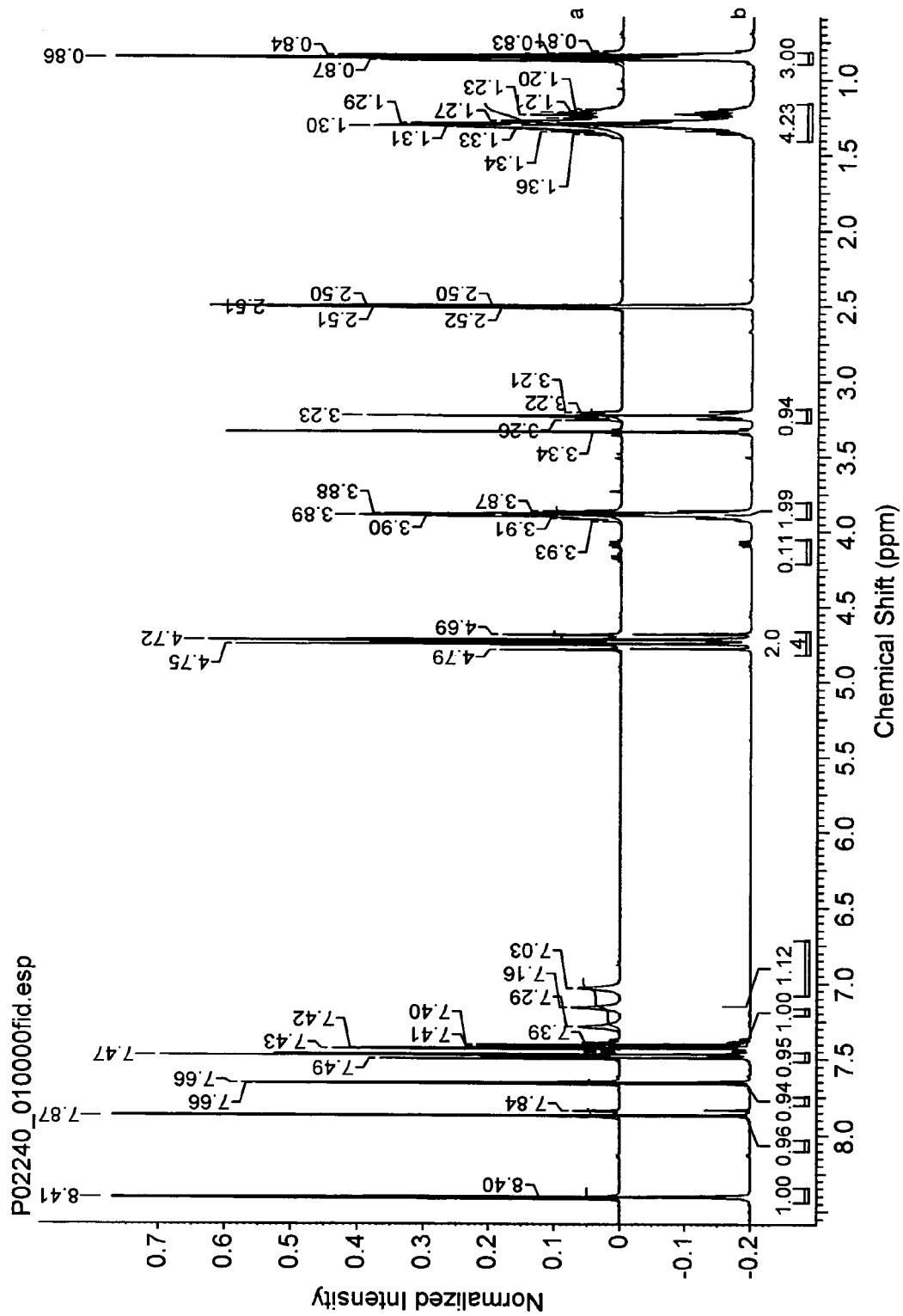
FIG. 25 shows NMR analysis of (a) propiconazole-2,2'-dihydroxy-1,1'-dinaphthalene co-crystal obtained using the technique described in Example 1b and (b) propiconazole.

FIG. 25 shows NMR analysis of (a) propiconazole-oxalic acid co-crystal obtained using the technique described in Example 1a and (b) propiconazole.

Figure 26:
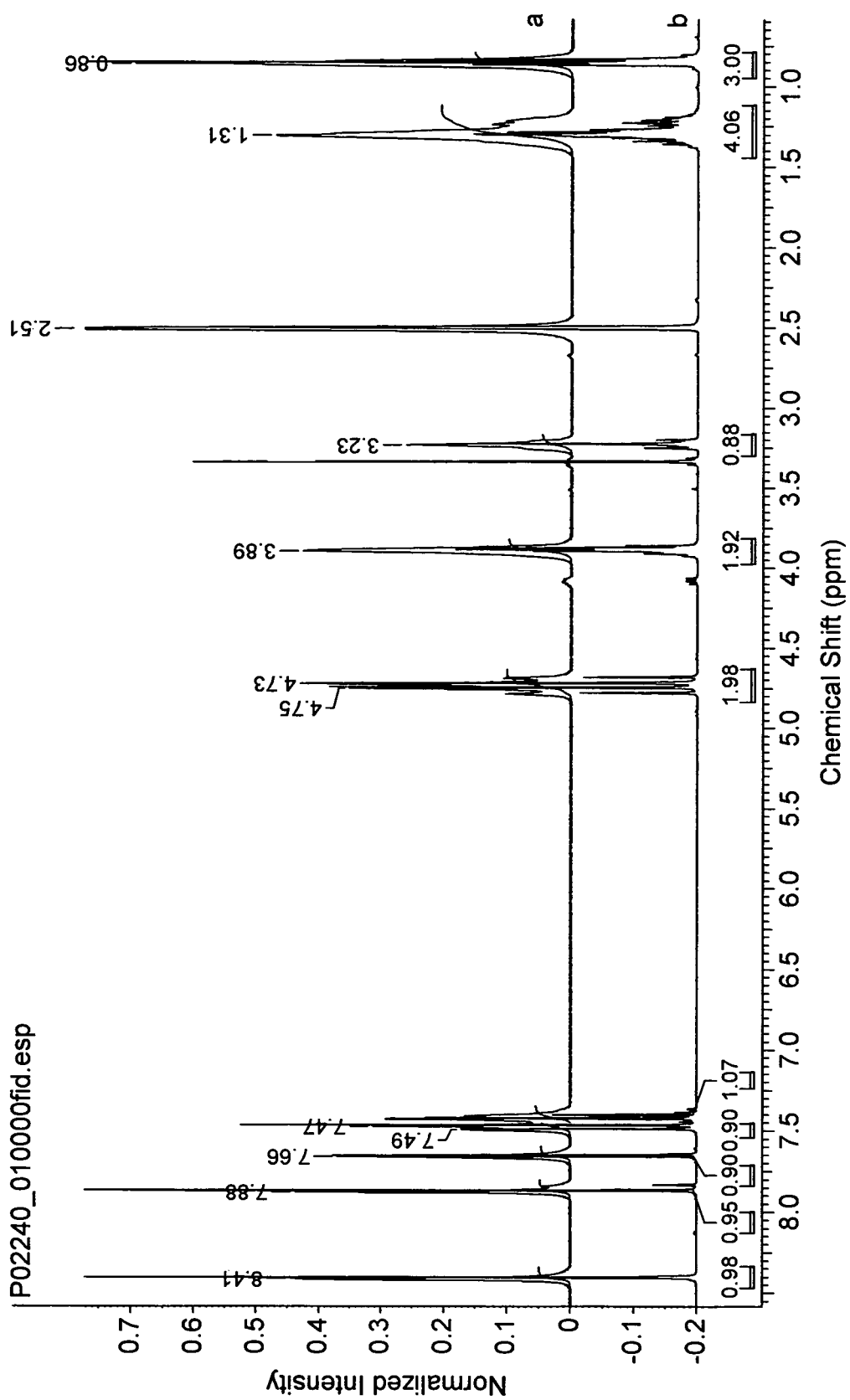
FIG. 26 shows NMR analysis of (a) propiconazole-D-ribose co-crystal obtained using the technique described in Example 1a and (b) propiconazole.

FIG. 26 shows NMR analysis of (a) propiconazole-oxalic acid co-crystal obtained using the technique described in Example 1b and (b) propiconazole.

Figure 27:
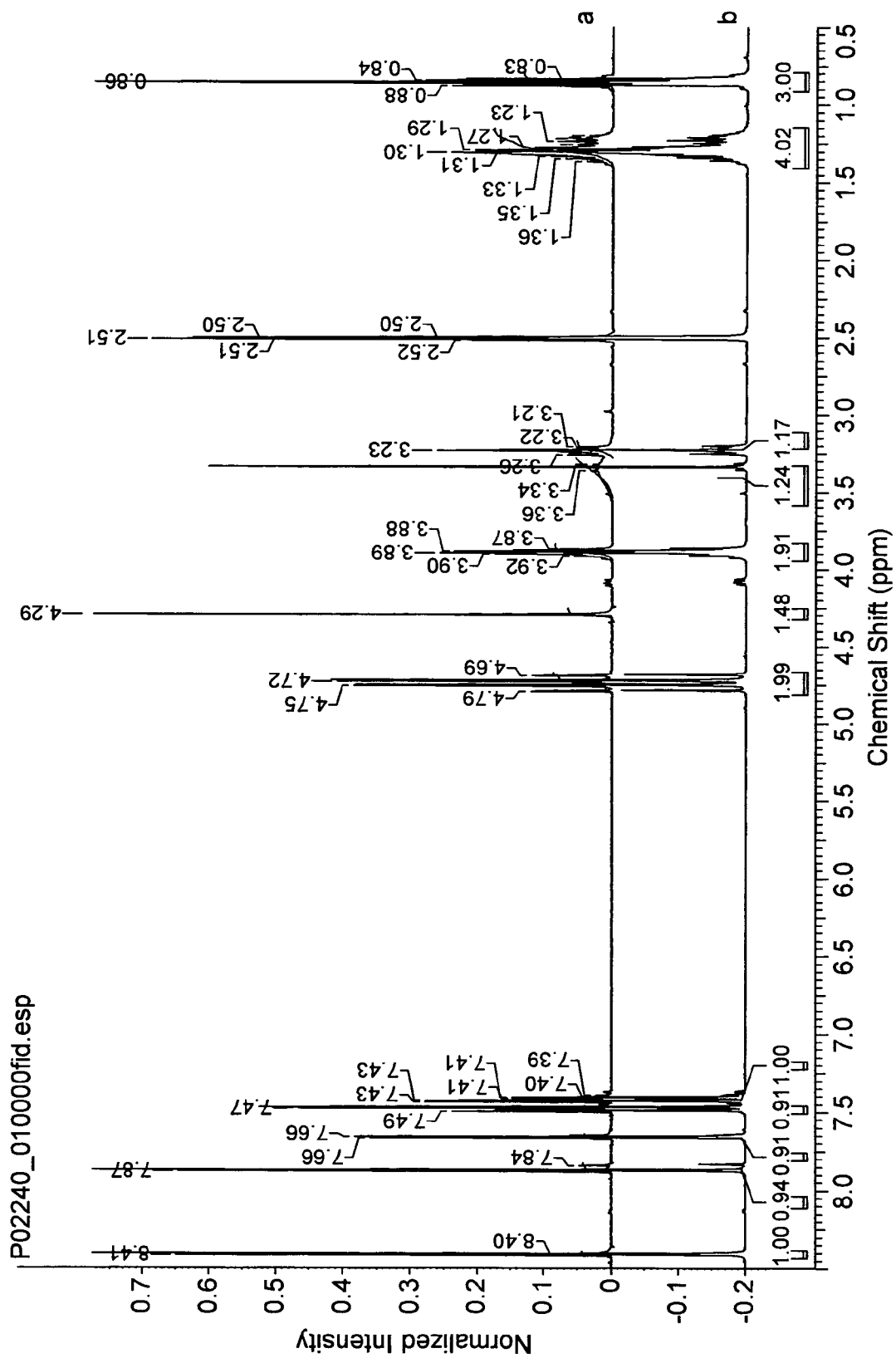
FIG. 27 shows NMR analysis of (a) propiconazole-2,5-dimethyl-2,5-hexanediol co-crystal obtained using the technique described in Example 1a (Batch 1) and (b) propiconazole.

FIG. 27 shows NMR analysis of (a) propiconazole-tartaric acid co-crystal obtained using the technique described in Example 1a and (b) propiconazole.

Figure 28:
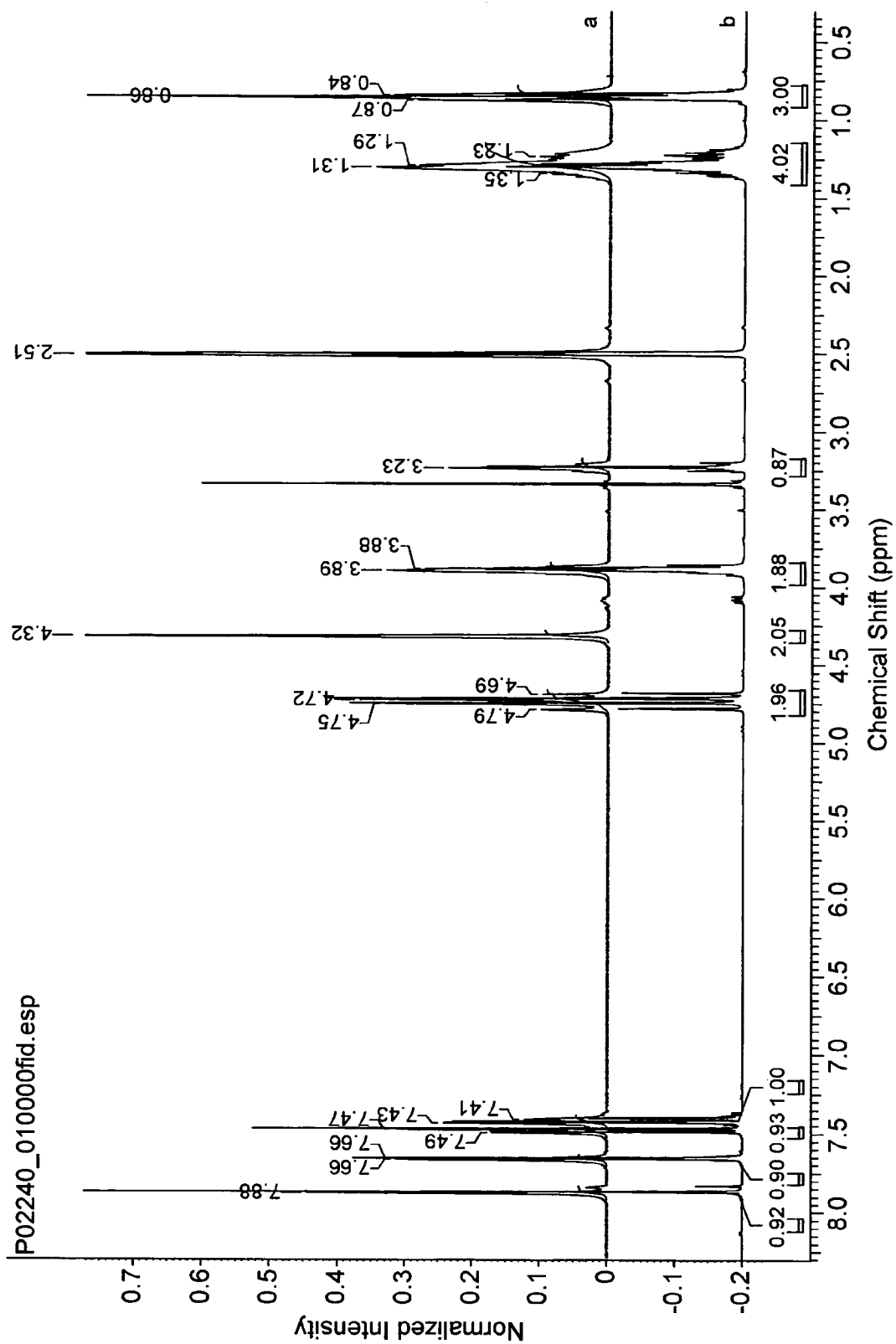
FIG. 28 shows NMR analysis of (a) propiconazole-2,5-dimethyl-2,5-hexanediol co-crystal obtained using the technique described in Example 1a (Batch 2) and (b) propiconazole.

FIG. 28 shows NMR analysis of (a) propiconazole-tartaric acid co-crystal obtained using the technique described in Example 1b and (b) propiconazole.

Figure 29:
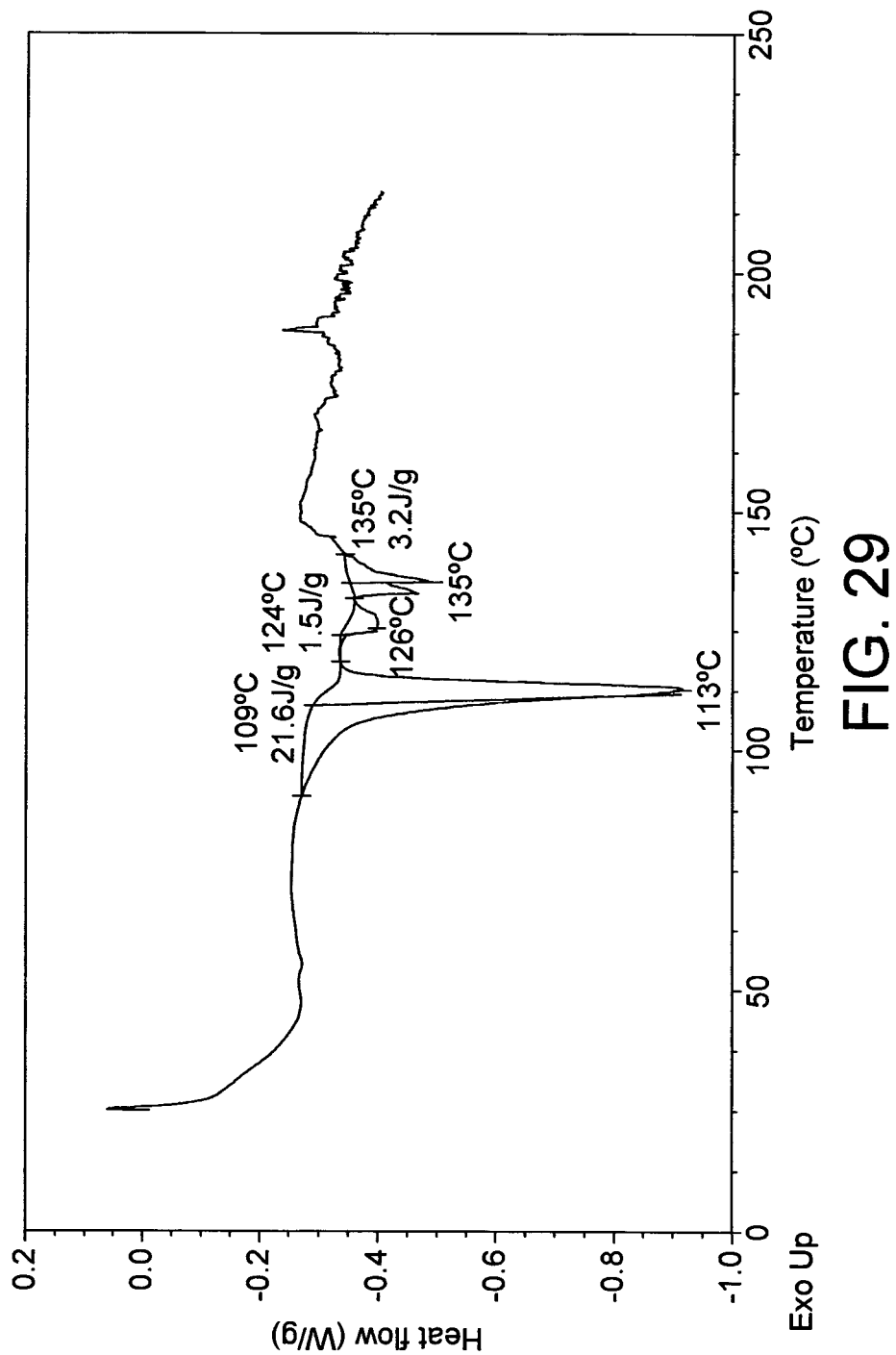
FIG. 29 shows NMR analysis of (a) propiconazole-trimesic acid co-crystal obtained using the technique described in Example 1a and (b) propiconazole.

FIG. 29 shows a DSC trace of propiconazole-2,2'-dihydroxy-1,1'-dinaphthalene co-crystal obtained using the technique described in Example 1b.

Figure 30:
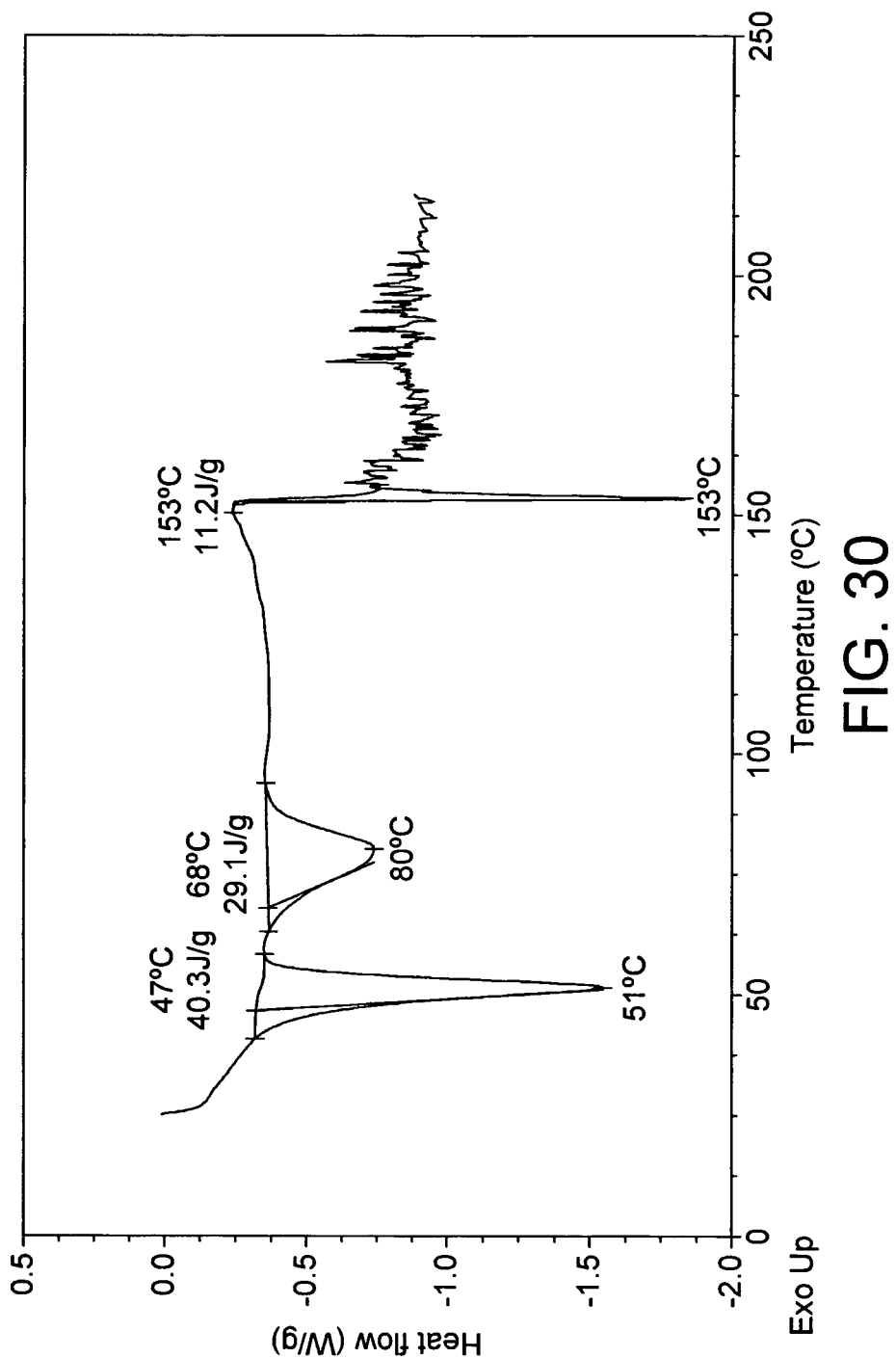
FIG. 30 shows NMR analysis of (a) propiconazole-terephthalic acid co-crystal obtained using the technique described in Example 1b and (b) propiconazole.

FIG. 30 shows a DSC trace of propiconazole-D-ribose co-crystal obtained using the technique described in Example 1a.

Figure 31:
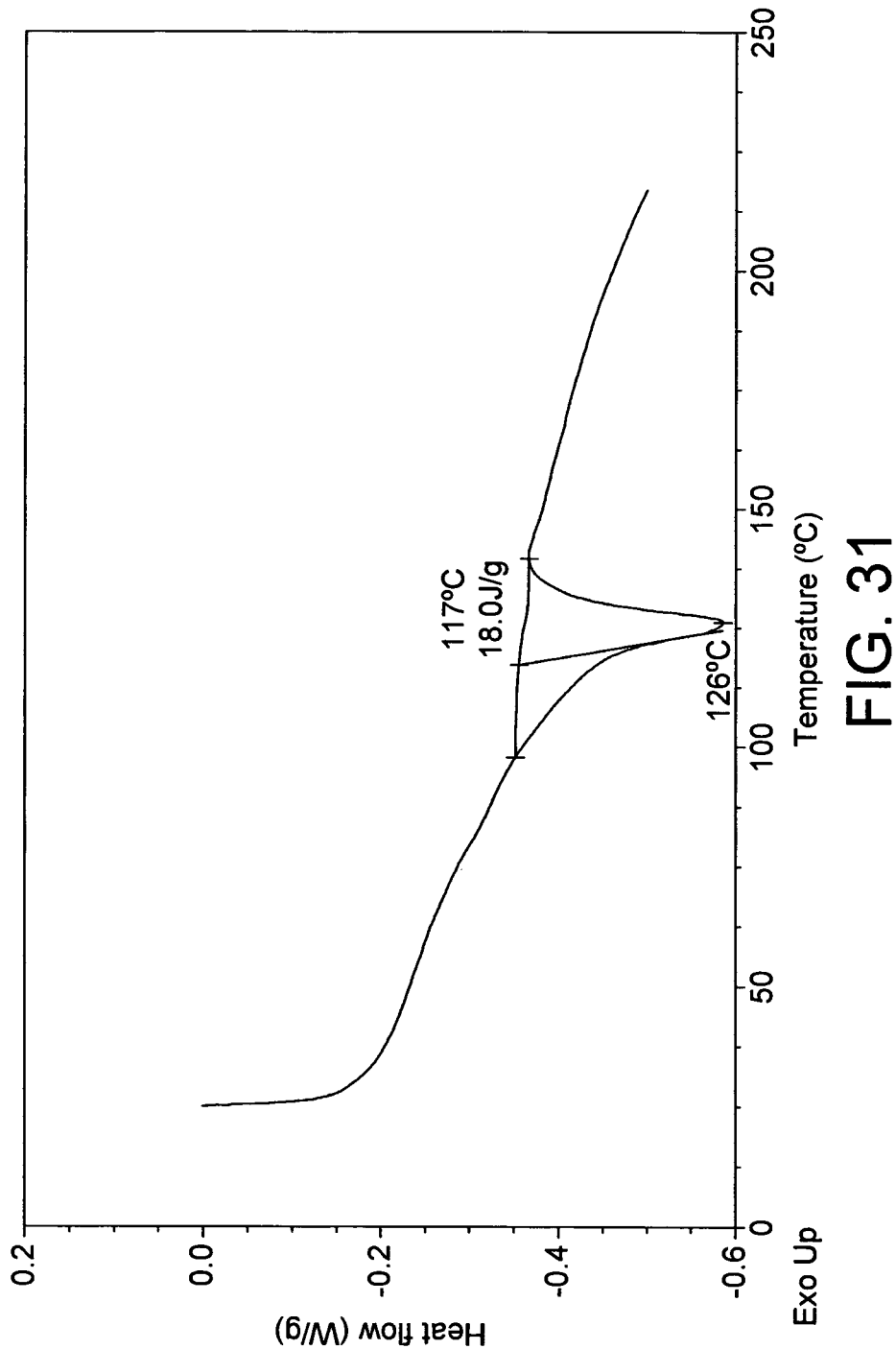
FIG. 31 shows NMR analysis of (a) propiconazole-maleic acid co-crystal obtained using the technique described in Example 1b and (b) propiconazole.

FIG. 31 shows a DSC trace of propiconazole-trimesic acid co-crystal obtained using the technique described in Example 1a.

Figure 32:
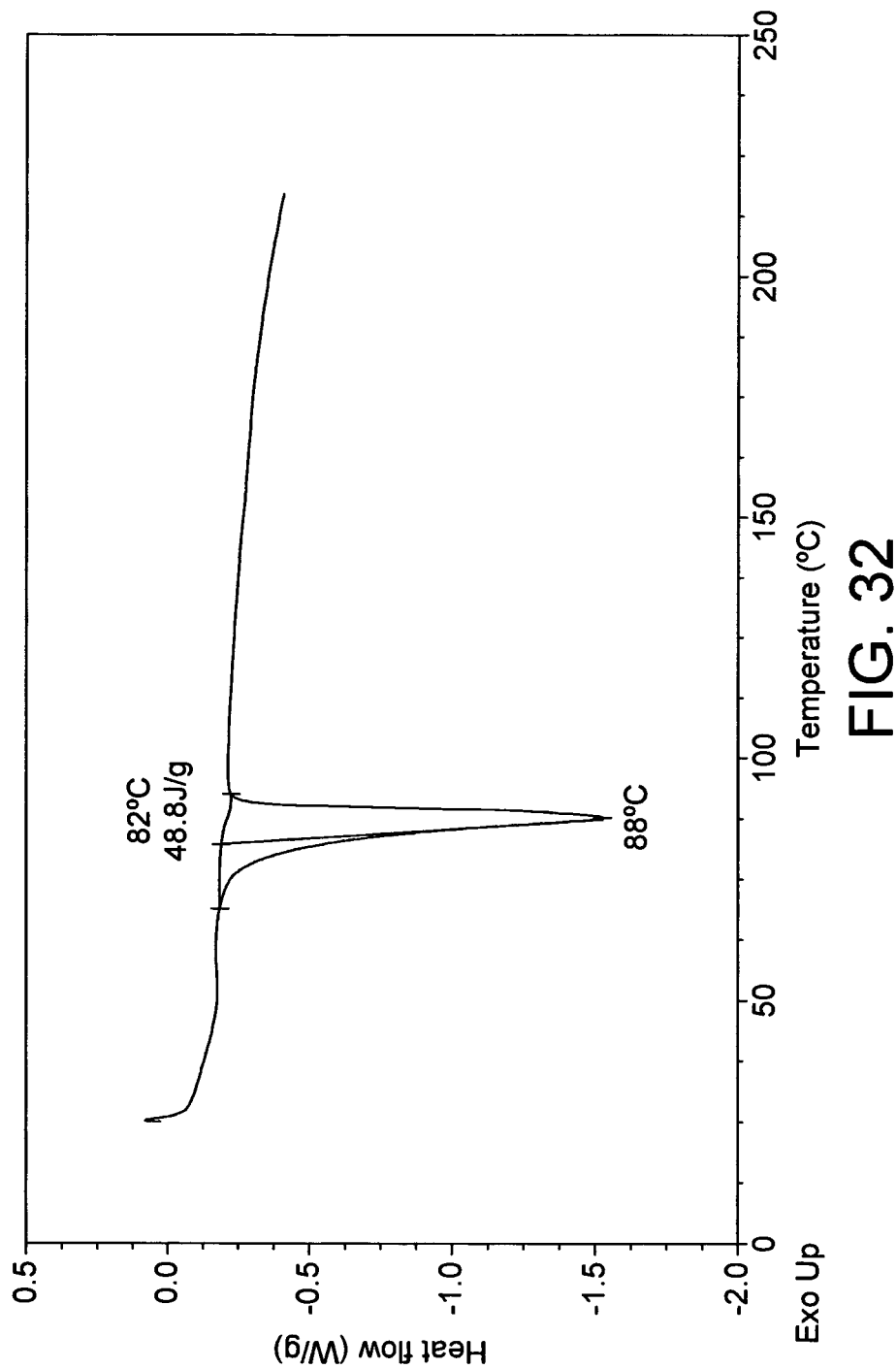
FIG. 32 shows NMR analysis of (a) propiconazole-maleic acid co-crystal obtained using the technique described in Example 1b and (b) propiconazole.

FIG. 32 shows a DSC trace of propiconazole-terephthalic acid co-crystal obtained using the technique described in Example 1b.

Figure 33:
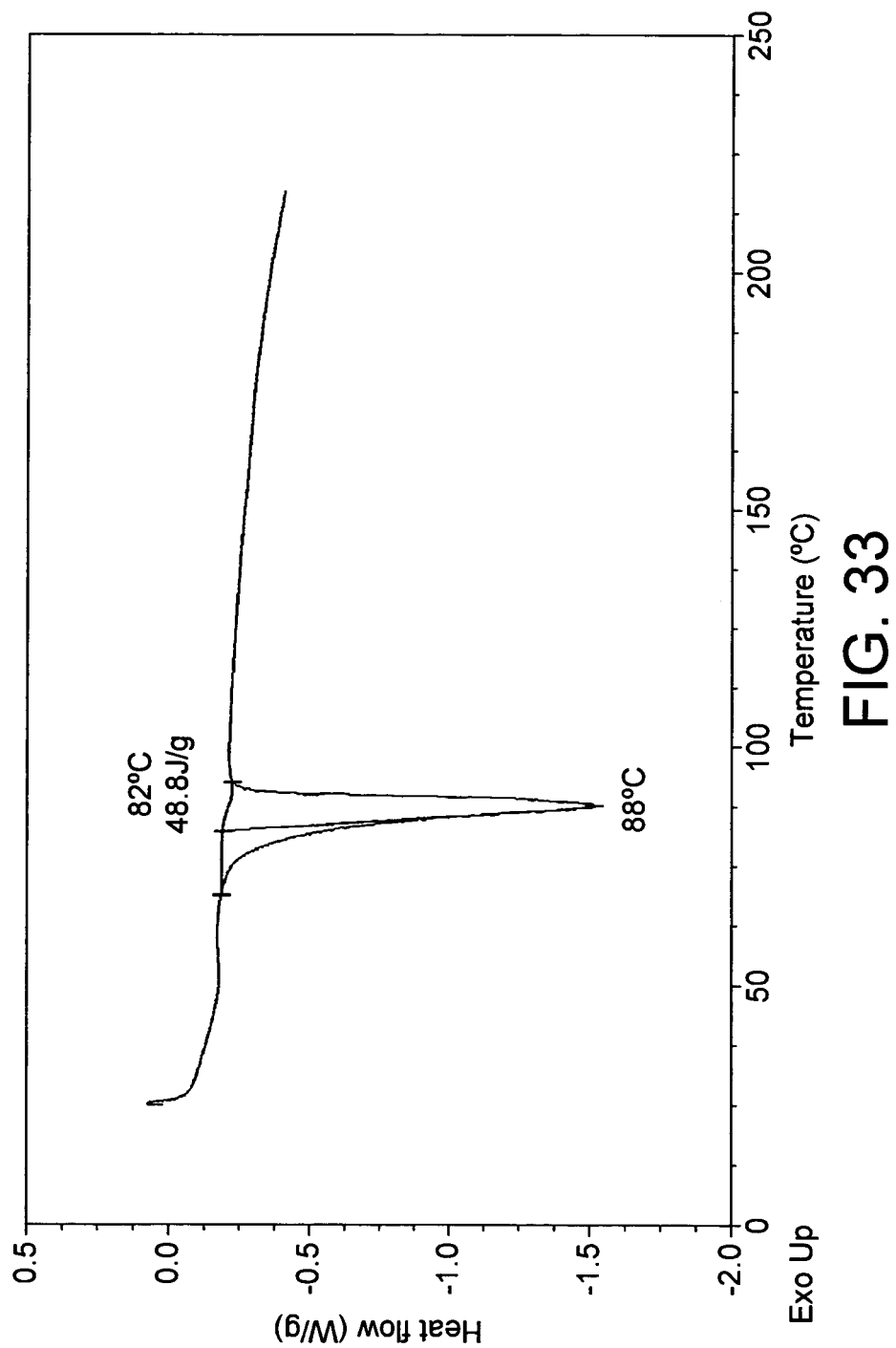
FIG. 33 shows NMR analysis of (a) propiconazole-oxalic acid co-crystal obtained using the technique described in Example 1a and (b) propiconazole.

FIG. 33 shows a DSC trace of propiconazole-terephthalic acid co-crystal obtained using the technique described in Example 1g.

Figure 34:
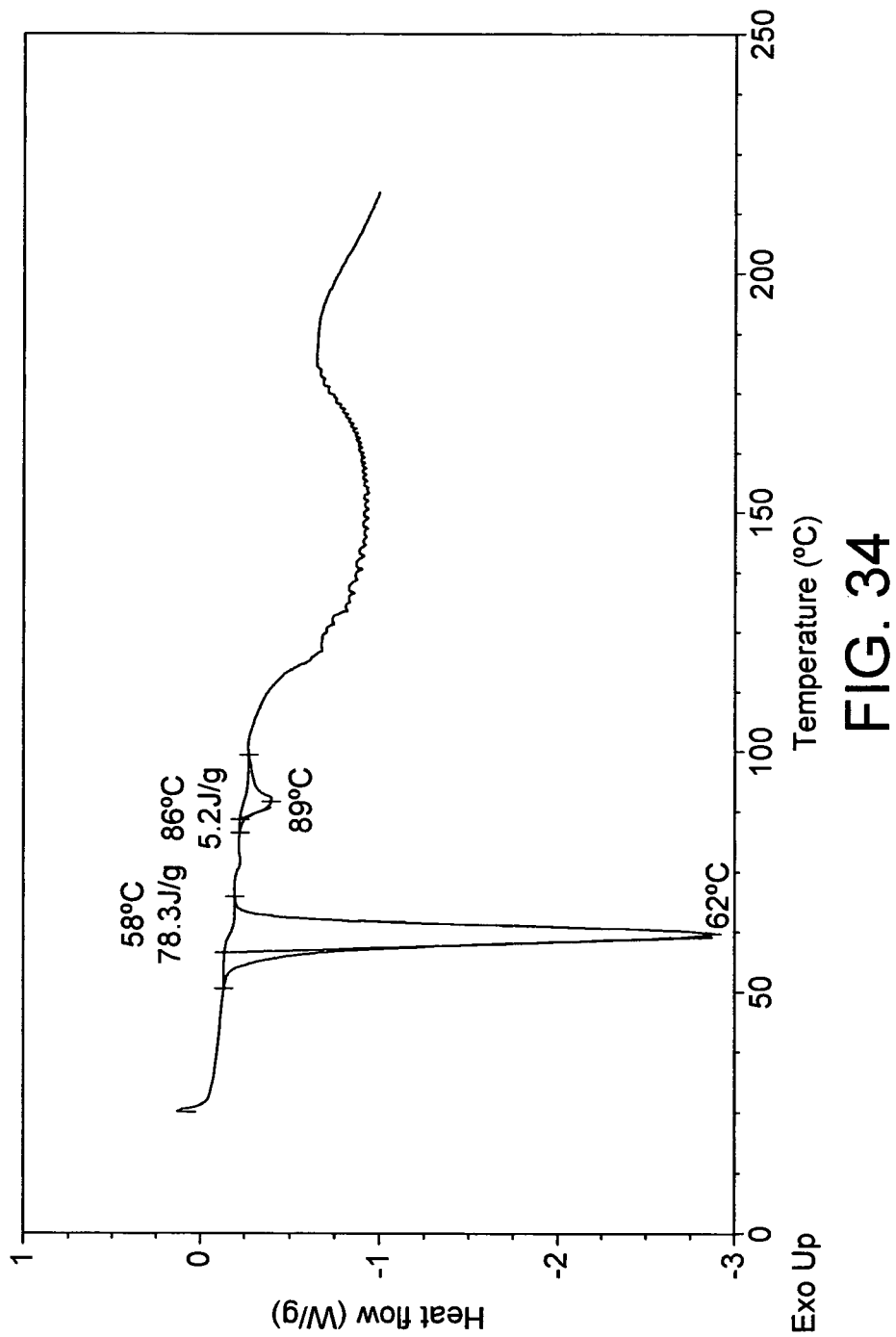
FIG. 34 shows NMR analysis of (a) propiconazole-oxalic acid co-crystal obtained using the technique described in Example 1b and (b) propiconazole.

FIG. 34 shows a DSC trace of propiconazole-maleic acid co-crystal obtained using the technique described in Example 1b.

Figure 35:
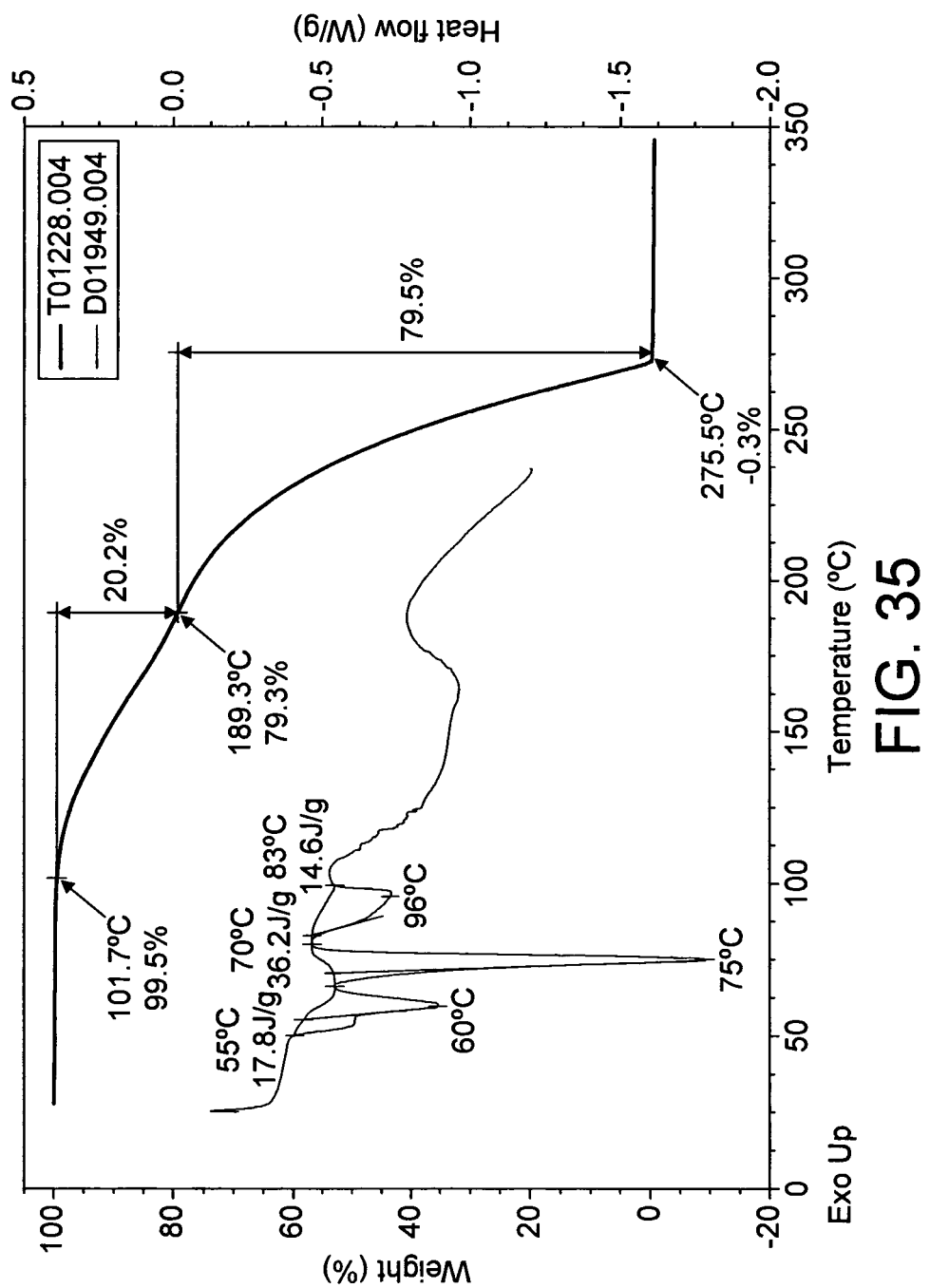
FIG. 35 shows NMR analysis of (a) propiconazole-tartaric acid co-crystal obtained using the technique described in Example 1a and (b) propiconazole.

FIG. 35 shows a DSC and TGA trace of propiconazole-maleic acid co-crystal obtained using the technique described in Example 1b.

Figure 36:
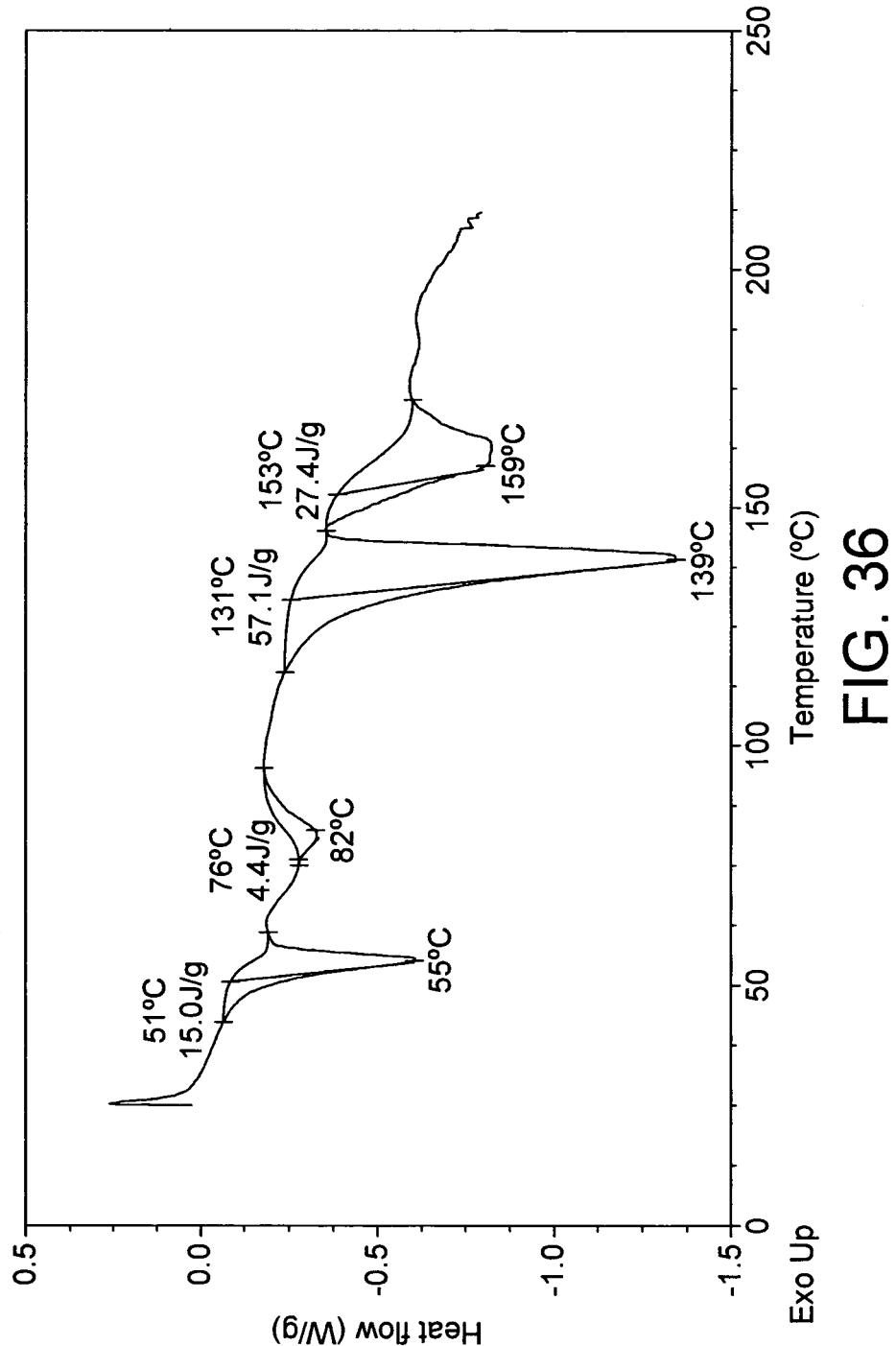
FIG. 36 shows NMR analysis of (a) propiconazole-tartaric acid co-crystal obtained using the technique described in Example 1b and (b) propiconazole.

FIG. 36 shows a DSC trace of propiconazole-oxalic acid co-crystal obtained using the technique described in Example 1a.

Figure 37:
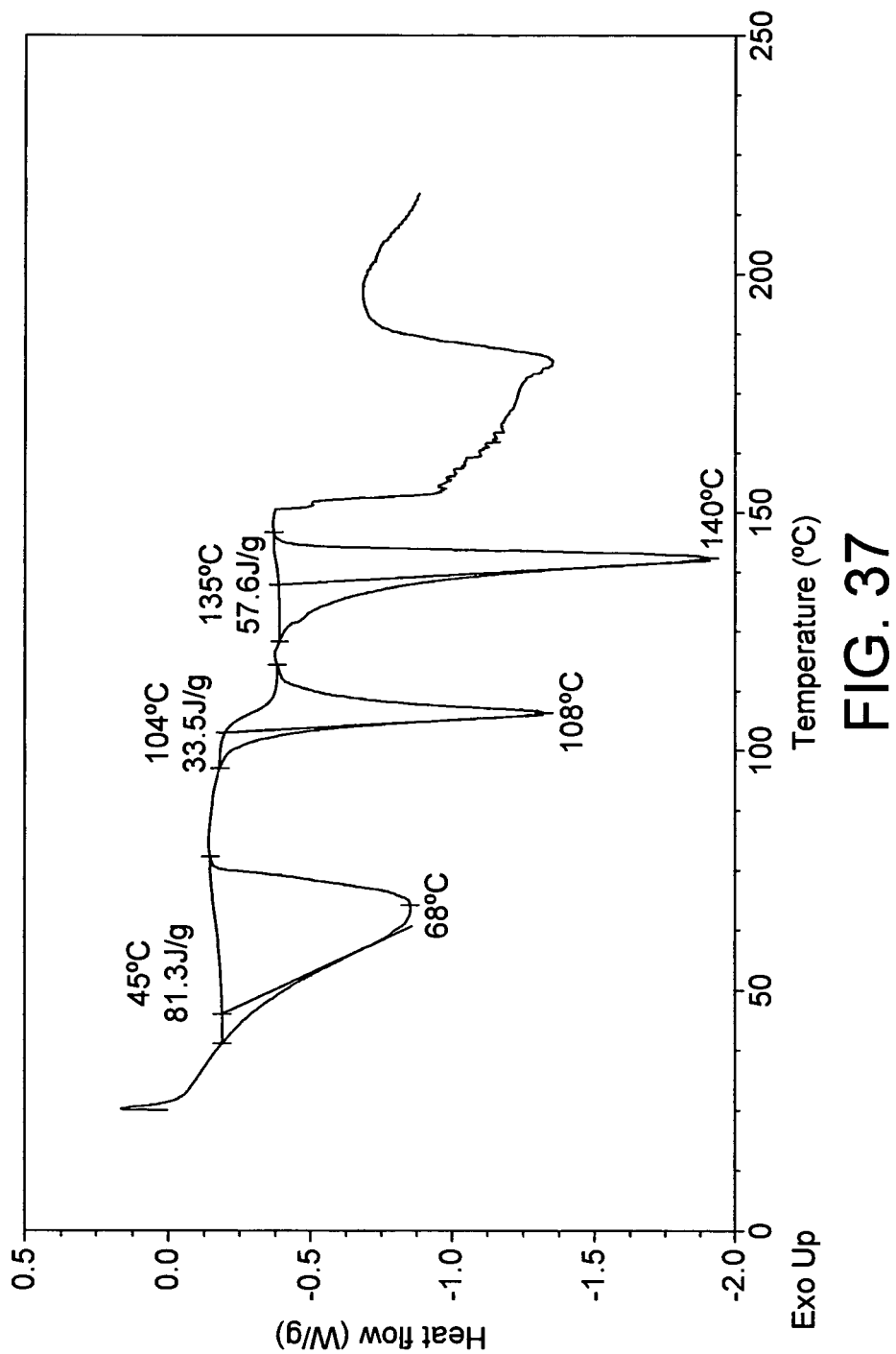
FIG. 37 shows NMR analysis of (a) propiconazole-sucrose co-crystal obtained using the technique described in Example 1a and (b) propiconazole.

FIG. 37 shows a DSC trace of propiconazole-oxalic acid co-crystal obtained using the technique described in Example 1b.

Figure 38:
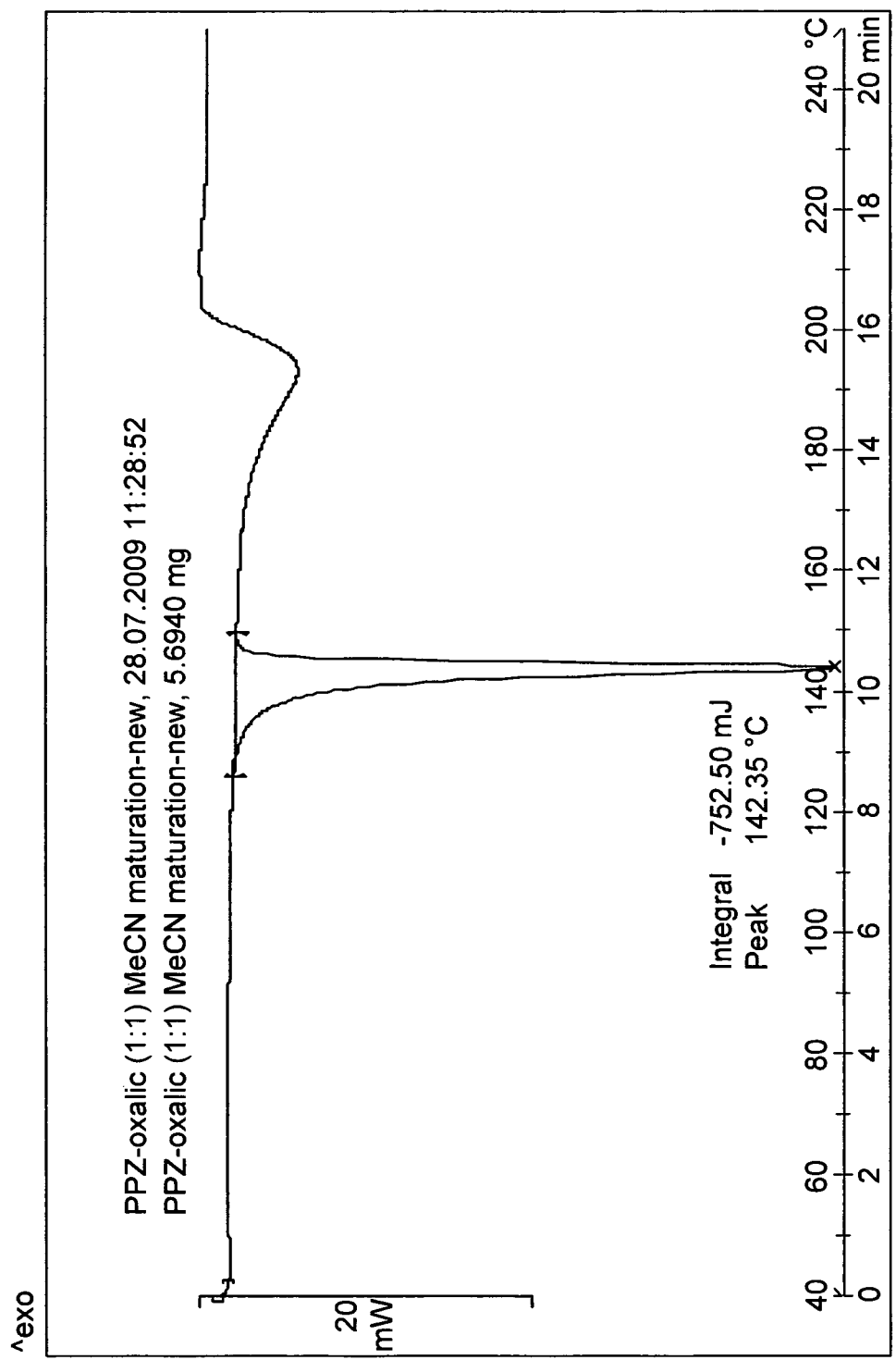
FIG. 38 shows NMR analysis of (a) propiconazole-trehalose co-crystal obtained using the technique described in Example 1a (Batch 1) and (b) propiconazole.

FIG. 38 shows a DSC trace of propiconazole-oxalic acid co-crystal obtained using the technique described in Example 1f.

Figure 39:
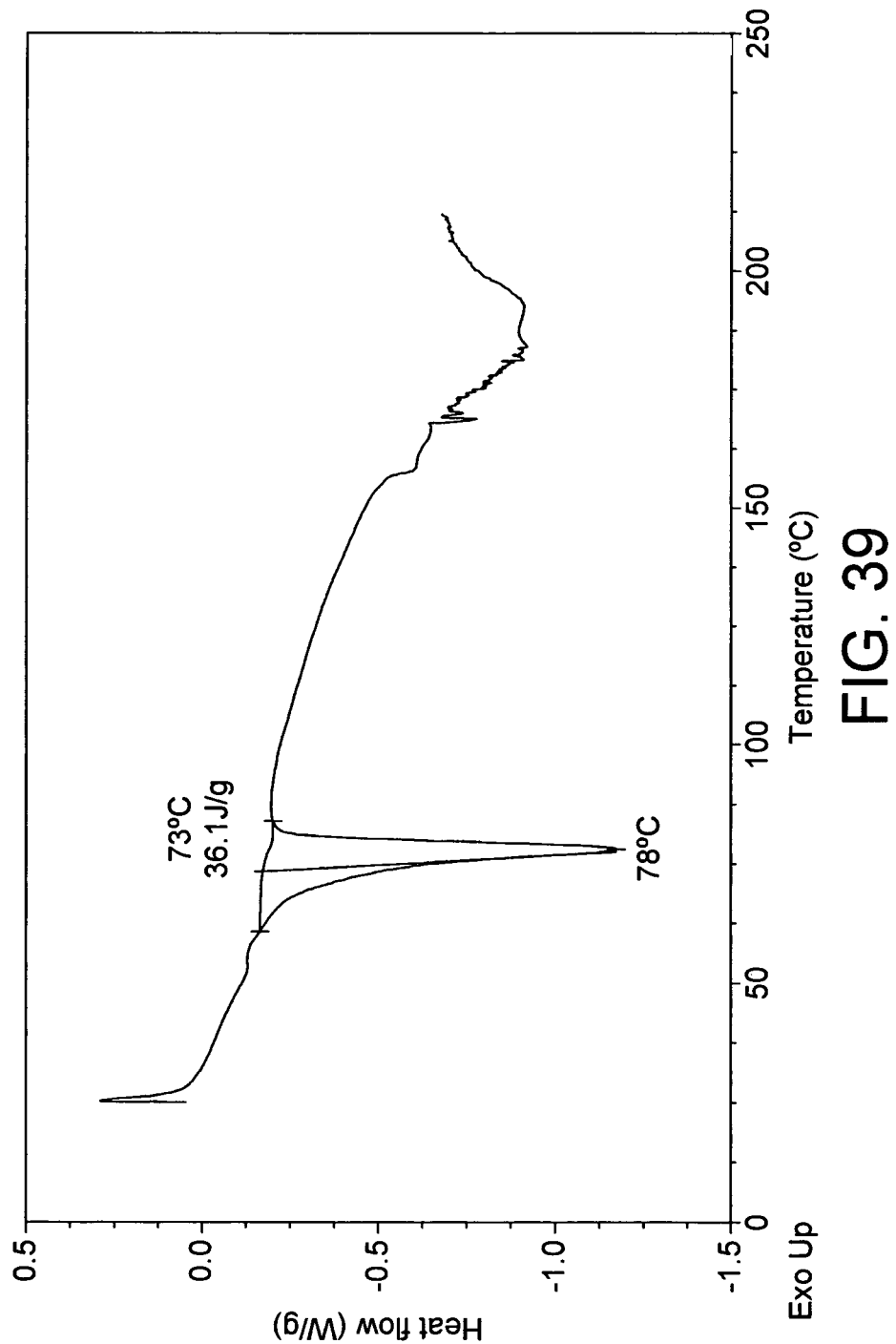
FIG. 39 shows NMR analysis of (a) propiconazole-trehalose co-crystal obtained using the technique described in Example 1a (Batch 2) and (b) propiconazole.

FIG. 39 shows a DSC trace of propiconazole-tartaric acid co-crystal obtained using the technique described in Example 1a.

Figure 40:
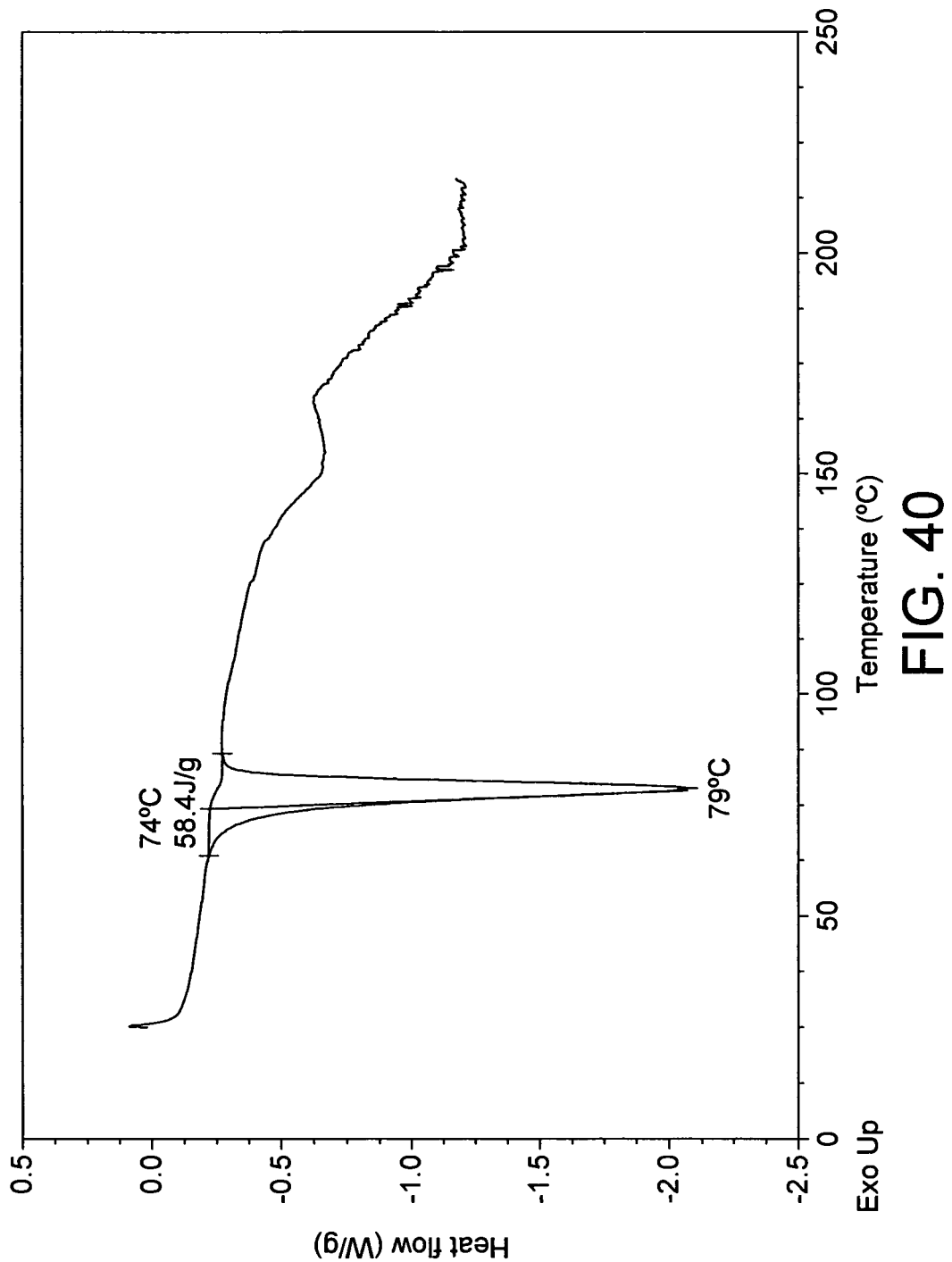
FIG. 40 shows a DSC trace of propiconazole-2,2'-dihydroxy-1,1'-dinaphthalene co-crystal obtained using the technique described in Example 1b.

FIG. 40 shows a DSC trace of propiconazole-tartaric acid co-crystal obtained using the technique described in Example 1b.

Figure 41:
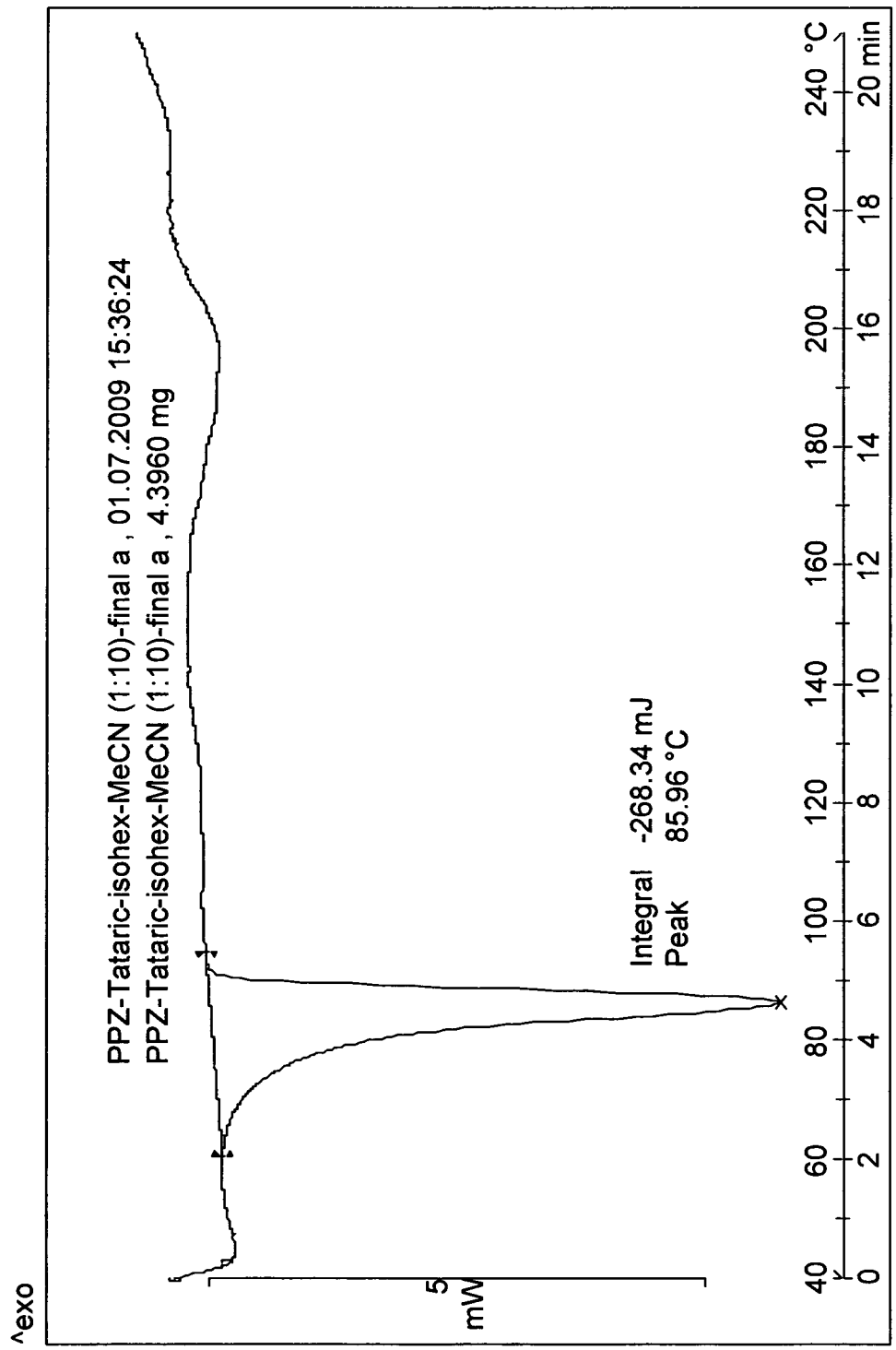

FIG. 41 shows a DSC trace of propiconazole-tartaric acid co-crystal obtained using the technique described in Example 1e.

EXAMPLES

1a. Preparation of Co-Crystals by Maturation

Approximately 20 mg of propriconazole was weighed into a 1.5 ml vial. Approximately 1 equivalent (by mass) of co-former was added to the propiconazole. 100 µl ethanol, methyl cyanate, ethyl acetate, tetrahydrofuran or toluene was added and the resulting slurrys were matured for 7 days on an 8 hour temperature cycle (heating from room temperature to 50° C. for 4 hours and then cooling back to room temperature over the next four hours). The sample was then dried overnight in a vacuum oven at room temperature.

1b. Preparation of Co-Crystals by Grinding

Grinding was performed using a modified Copley ball mill capable of high throughput screening Approximately 100 mg of propiconazole was weighed into a stainless steel ball mill prior to the addition of 1 equivalent (by mass) of co-former, a stainless steel ball and 100 µl of hexane. The sample was shaken at a frequency of 20 Hz for 60 minutes. The sample was then dried overnight in a vacuum oven at room temperature.

1c. Preparation of Co-Crystals by Microwave Irradiation

Approximately 50 mg of propiconazole was weighed into a 10 ml microwave tube to which 1 equivalent (by mass) of co-former and 100 µl of hexane were added. The sample was irradiated using an S-class discover CEM microwave for 10 minutes (maximum temperature of 150° C.; 300 W microwave power).

1d. Preparation of Co-Crystals by Sonication

Approximately 50 mg of propiconazole was weighed into 1.5 ml HPLC vials to which 1 equivalent (by mass) of co-former and 100 µl of hexane were added. The sample was then subjected to a series of indirect sonication pulses (3 seconds on and 5 seconds off) using a S-4000 Misonix sonicator for a period of 10 minutes at 100% of the instrument power (600 W).

1e. Additional Preparation Method for Propioconazole-Tartaric Acid Co-Crystals 6.16 g of tartaric acid was added to a 100 ml jacketed vessel; 77 ml of a isohexane:MeCN (1:10 v/v) mixture was then also added to the vessel. The solution was stirred at 25° C. using high shear stirring for 20 minutes, after which the high shear stirrer was replaced with a glass agitator. 28 g of propiconazole was added gradually to the solution to give a final molar ratio of 2:1 (propiconazole:tartaric acid). The vessel was then stirred for 12 h at 25° C. The final product was filtered by vacuum filtration and then dried in a vacuum oven.

1f. Additional Preparation Method for Propioconazole-Oxalic Acid Co-Crystals 30 ml of acetonitrile was added to a jacketed vessel; 1.315 g of oxalic acid was then also added to the vessel. The solution was stirred with a glass agitation at 50° C. for 20 minutes to dissolve the oxalic acid, after which 5 g of propioconazole was added gradually to the solution to give a final molar ratio of 1:1 (propiconazole:oxalic acid). The vessel was then stirred for 20 minutes at 50° C. It was then allowed to cool naturally to room temperature and held for 12 h with stirring. The final product was filtered by vacuum filtration and then dried in a vacuum oven.

1g. Additional Preparation Method for Propioconazole-Terephthalic Axid Co-Crystals 20 ml of DMSO was added to a 100 ml beaker; 1.21 g of terephthalic acid was then also added, followed by gradual addition of 5 g of propioconazole to give a final molar ratio of 1:1 (propiconazole:terephthalic acid). The resulting solution was agitated using a magnetic stirrer at room temperature until the propioconazole and terephathalic acid were dissolved. The solution was then transferred into a crystallization dish and left to evaporate at room temperature; the resulting crystals were isolated once the DMSO had completely evaporated.

2. Analysis of Co-Crystals

After preparation by one of the methods detailed above, any resultant oils and gums were discarded. All other samples were subject to analysis by powder X-ray diffraction. Powder X-ray diffraction patterns for each of the resultant crystals are shown in FIGS. 1 to 17 as described above. These powder X-ray diffraction traces clearly show that the product co-crystals bear no resemblance to either of their constituent phases suggesting that a new solid state has been formed. The 2θ values of selected peak positions of the powder X-ray diffraction patterns of these crystals are shown in Tables 1 to 7 above.

Using the maturation method (1a), co-crystals were obtained for propiconazole with D-ribose, 2,5-dimethyl-2,5-hexanediol, trimesic acid, oxalic acid and tartaric acid.

Using the grinding method (1b), co-crystals were obtained for propiconazole with 2,2'-dihydroxy-1,1'-dinaphthalene, terephthalic acid, maleic acid, oxalic acid and tartaric acid.

Using the microwave irradiation method (1c), co-crystals were obtained for propiconazole with 2,2'-dihydroxy-1,1'-dinaphthalene, D-ribose, maleic acid and oxalic acid.

Using the sonication method (1d), co-crystals were obtained for propiconazole with D-ribose and oxalic acid.

Where possible, those samples showing novel diffractograms were further analysed by DSC and $^1$H NMR and, in addition, their chemical stability was assessed (7 days at 40° C. and 75% relative humidity). In one example, thermogravimetric analysis (TGA) was carried out (the trace is shown in FIG. 35).

NMR traces are shown in FIGS. 18 to 28 as described above.

DSC traces are shown in FIGS. 29 to 41 as described above.

Propiconazole-tartaric acid crystals obtained from Example 1e were analysed by GC and LNMR and displayed a 2:1 stoichiometric ratio of propiconazole and tartaric acid.

Propiconazole-oxalic acid crystals obtained from Example 1f were analysed by GC and LNMR and displayed a 1:1 stoichiometric ratio of propiconazole and oxalic acid.

It is noted that some peaks in the powder X-ray diffraction traces disappear after chemical stability analysis and/or the trace may change more dramatically. Whilst not wishing to be bound by hypothesis, it is postulated that the former is due to the presence of unreacted propiconazole and/or co-former in the sample which then crystallises during the stablility trials. The latter is likely due to the change from one polymorphic form of the co-crystal to a more stable polymorphic form during the stability trials.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A co-crystal of propiconazole with a co-crystal forming compound, wherein said co-forming compound is selected from the group consisting of 2,2'-dihydroxy-1,1'-dinaphthalene, D-ribose, maleic acid, oxalic acid, tartaric acid, terephthalic acid and trimesic acid, and wherein, when the co-crystal forming compound is 2,2'-dihydroxy-1,1'-dinaphthalene, the co-crystal has a powder X-ray diffraction pattern expressed in terms of 2θ angle values, said powder X-ray diffraction pattern comprising at least three 2θ angle values selected from the group comprising (a) 5.9±0.2, 10.2±0.2, 15.2±0.2 and 18.4±0.2 or (b) 5.8±0.2, 8.7±0.2, 10.7±0.2, 15.1±0.2 and 18.1±0.2;

when the co-crystal forming compound is D-ribose, the co-crystal has a powder X-ray diffraction pattern expressed in terms of 2θ angle values, said powder X-ray diffraction pattern comprising at least three 2θ angle values selected from the group comprising (a) 7.7±0.2, 8.6±0.2, 13.9±0.2, 18.2±0.2 and 25.0±0.2 or all of the 2θ angles (b) 21.8±0.2, 24.0±0.2 and 26.1±0.2 or (c) 11.3±0.2;

when the co-crystal forming compound is maleic acid, the co-crystal has a powder X-ray diffraction pattern expressed in terms of 2θ angle values, said powder X-ray diffraction pattern comprising at least three 2θ angle values selected from the group comprising (a) 7.6±0.2, 10.3±0.2, 16.4±0.2, 18.2±0.2, 19.4±0.2 and 20.2±0.2, (d) 7.6±0.2, 10.4±0.2, 11.8±0.2, 15.4±0.2, 16.1±0.2 and 19.5±0.2 or (e) 5.9±0.2, 7.6±0.2, 10.5±0.2, 15.5±0.2 and 16.2±0.2 or all of the 2θ angle values (b) 5.4±0.2, 10.9±0.2 and 21.1±0.2 or (c) 21.4±0.2 and, 26.1±0.2;

when the co-crystal forming compound is oxalic acid, the co-crystal has a powder X-ray diffraction pattern expressed in terms of 2θ angle values, said powder X-ray diffraction pattern comprising at least three 2θ angle values selected from the group comprising 6.7±0.2, 10.3±0.2, 11.1±0.2, 14.9±0.2, 16.3±0.2 and 19.7±0.2;

when the co-crystal forming compound is tartaric acid, the co-crystal has a powder X-ray diffraction pattern expressed in terms of 2θ angle values, said powder X-ray diffraction pattern comprising at least three 2θ angle values selected from the group comprising 6.0±0.2, 12.0±0.2, 18.0±0.2 and 24.6±0.2;

when the co-crystal forming compound is terephthalic acid, the unit cell parameters are as shown in Table 4B; and when the co-crystal forming compound is trimesic acid, the co-crystal has a powder X-ray diffraction pattern expressed in terms of 2θ angle values, said powder X-ray diffraction pattern comprising 2θ angle values 5.8±0.2, 10.2±0.2 and 16.3±0.2.

2. A method for the protection of industrial material from fungal attack comprising treating the industrial material with a composition of claim 1.

3. The co-crystal of claim 1, wherein the co-crystal forming compound is 2,2'-dihydroxy-1,1'-dinaphthalene.

4. The co-crystal of claim 1, wherein the co-crystal forming compound is D-ribose.

5. The co-crystal of claim 1, wherein the co-crystal forming compound is trimesic acid.

6. The co-crystal of claim 1, wherein the co-crystal forming compound is maleic acid.

7. A process of preparing a co-crystal of claim 1 comprising a) grinding, heating or contacting in solution propiconazole with the co-crystal forming compound, under crystallisation conditions so as to form a solid phase; b) isolating co-crystals comprising propiconazole and the co-crystal forming compound.

8. A fungicidal composition comprising the co-crystal of claim 1.

9. The composition of claim 8 which is an agrochemical composition.

10. A method of preventing/controlling fungal infection on plants comprising treating the plant with a fungicidally effective amount of an agricultural composition of claim 9.

11. An agrochemical formulation comprising the composition of claim 9 which is a suspension concentrate.

12. A method for the protection of industrial material from fungal attack comprising treating the industrial material with a composition of claim 8.

13. The co-crystal of claim 1, wherein the melting point of the co-crystal is in the range of 50° C. to 350° C.

14. The co-crystal of claim 1, wherein the melting point of the co-crystal is in the range of 80° C. and 150° C.

15. The co-crystal of claim 1, wherein the co-crystal forming compound is tartaric acid.

16. The co-crystal of claim 1, wherein the co-crystal forming compound is oxalic acid.

17. The co-crystal of claim 1, wherein the co-crystal forming compound is terephthalic acid.

18. The co-crystal of claim 1, wherein the melting point of the co-crystal is above 45° C.

19. The co-crystal of claim 1, wherein hydrogen bonding occurs between the co-crystal forming compound and the propiconazole.

* * * * *